(12) United States Patent
Angros et al.

(10) Patent No.: US 8,298,485 B2
(45) Date of Patent: Oct. 30, 2012

(54) IN SITU HEAT INDUCED ANTIGEN RECOVERY AND STAINING APPARATUS AND METHOD

(75) Inventors: Lee Angros, Bethany, OK (US); Thomas Lee Byers, Mustang, OK (US)

(73) Assignee: Lee H. Angros, Bethany, OK (US)

( * ) Notice: Subject to any disclaimer, the term of this patent is extended or adjusted under 35 U.S.C. 154(b) by 1519 days.

(21) Appl. No.: 11/440,312

(22) Filed: May 24, 2006

(65) Prior Publication Data
US 2006/0281116 A1    Dec. 14, 2006

Related U.S. Application Data

(60) Provisional application No. 60/684,047, filed on May 24, 2005, provisional application No. 60/689,386, filed on Jun. 10, 2005, provisional application No. 60/730,744, filed on Oct. 27, 2005.

(51) Int. Cl.
*G01N 21/00*    (2006.01)
*G01N 33/53*    (2006.01)

(52) U.S. Cl. ......... 422/71; 422/101; 422/102; 422/104; 436/518

(58) Field of Classification Search .......... 422/71, 422/101, 102, 104; 436/518
See application file for complete search history.

(56) References Cited

U.S. PATENT DOCUMENTS

| | | |
|---|---|---|
| 3,645,690 A | 2/1972 | Rochte et al. |
| 4,296,070 A | 10/1981 | Montalto et al. |
| 4,510,119 A * | 4/1985 | Hevey ............... 422/71 |
| 4,847,208 A | 7/1989 | Bogen |
| 4,855,109 A | 8/1989 | Muraishi et al. |
| 4,857,272 A | 8/1989 | Sugaya |
| 5,073,504 A | 12/1991 | Bogen |
| 5,154,889 A | 10/1992 | Muraishi |
| 5,225,325 A | 7/1993 | Miller et al. |
| 5,232,664 A | 8/1993 | Krawzak et al. |

(Continued)

FOREIGN PATENT DOCUMENTS
EP    402994 A2    12/1990
(Continued)

OTHER PUBLICATIONS
U.S. Appl. No. 60/076,198, filed Feb. 27, 1998, Ford et al.
(Continued)

*Primary Examiner* — Mark Shibuya
*Assistant Examiner* — Pensee Do
(74) *Attorney, Agent, or Firm* — Dunlap Codding, P.C.

(57) ABSTRACT

Contemplated herein is an automated microscope slide antigen recovery and staining apparatus and method that features a plurality of individually operable miniaturized pressurizable reaction compartments for individually and independently processing a plurality of individual microscope slides. The apparatus preferably features independently movable slide support elements each having an individually heatable heating plate. Each slide support element preferably supports a single microscope slide. Each microscope slide can be enclosed within an individual pressurizable reaction compartment. Pressures exceeding 1 atm or below 1 atm can be created and maintained in the reaction compartment prior to, during or after heating of the slide begins. Because of the ability to pressurize and regulate pressure within the reaction compartment, and to individually heat each slide, each slide and a liquid solution or reagent thereon can be heated to temperatures that could not be obtained without the enclosed pressurized environment of the reaction compartment. A reagent dispensing strip having a plurality of reconfigurable reagent modules may also be used.

12 Claims, 24 Drawing Sheets

U.S. PATENT DOCUMENTS

| | | |
|---|---|---|
| 5,244,787 A | 9/1993 | Key et al. |
| 5,250,262 A | 10/1993 | Heidt et al. |
| 5,273,905 A | 12/1993 | Muller et al. |
| 5,316,452 A | 5/1994 | Bogen et al. |
| 5,355,439 A | 10/1994 | Bernstein et al. |
| 5,356,595 A | 10/1994 | Kanamori et al. |
| 5,425,918 A | 6/1995 | Healey et al. |
| 5,439,649 A | 8/1995 | Tseung et al. |
| 5,525,514 A | 6/1996 | Jacobs et al. |
| 5,551,487 A | 9/1996 | Gordon et al. |
| 5,578,452 A | 11/1996 | Shi et al. |
| 5,595,707 A | 1/1997 | Copeland et al. |
| 5,645,114 A | 7/1997 | Bogen et al. |
| 5,650,327 A | 7/1997 | Copeland et al. |
| 5,654,199 A | 8/1997 | Copeland et al. |
| 5,654,200 A | 8/1997 | Copeland et al. |
| 5,675,715 A | 10/1997 | Bernstein et al. |
| 5,696,887 A | 12/1997 | Bernstein et al. |
| 5,737,499 A | 4/1998 | Bernstein et al. |
| 5,758,033 A | 5/1998 | Bernstein et al. |
| 5,804,141 A | 9/1998 | Chianese |
| 5,819,842 A | 10/1998 | Potter |
| 5,839,091 A | 11/1998 | Rhett et al. |
| 5,882,601 A | 3/1999 | Kath et al. |
| 5,922,604 A | 7/1999 | Stapleton et al. |
| 5,947,167 A | 9/1999 | Bogen et al. |
| 5,948,359 A | 9/1999 | Kalra et al. |
| 5,958,341 A | 9/1999 | Chu |
| 5,985,669 A | 11/1999 | Palander |
| 6,093,574 A | 7/2000 | Druyor-Sanchez et al. |
| 6,096,271 A | 8/2000 | Bogen et al. |
| 6,180,061 B1 | 1/2001 | Bogen et al. |
| 6,183,693 B1 | 2/2001 | Bogen et al. |
| 6,207,408 B1 | 3/2001 | Essenfeld et al. |
| 6,218,191 B1 | 4/2001 | Palander |
| 6,245,297 B1 * | 6/2001 | Kowallis .................. 422/66 |
| 6,296,809 B1 | 10/2001 | Richards et al. |
| 6,352,861 B1 | 3/2002 | Copeland |
| 6,358,473 B1 | 3/2002 | Coello et al. |
| 6,403,036 B1 | 6/2002 | Rodgers et al. |
| 6,403,931 B1 | 6/2002 | Showalter et al. |
| 6,451,551 B1 | 9/2002 | Zhan et al. |
| 6,472,217 B1 | 10/2002 | Richards et al. |
| 6,489,171 B1 | 12/2002 | Aghassi et al. |
| 6,495,106 B1 | 12/2002 | Kalra et al. |
| 6,534,008 B1 | 3/2003 | Angros |
| 6,541,261 B1 | 4/2003 | Bogen et al. |
| 6,544,798 B1 | 4/2003 | Christensen et al. |
| 6,582,962 B1 | 6/2003 | Richards et al. |
| 6,594,537 B1 | 7/2003 | Bernstein et al. |
| 6,632,598 B1 | 10/2003 | Zhang et al. |
| 6,649,368 B1 | 11/2003 | Aghassi et al. |
| 6,673,620 B1 | 1/2004 | Loeffler et al. |
| 6,678,577 B1 | 1/2004 | Stylli et al. |
| 6,719,449 B1 | 4/2004 | Laugharn, Jr. et al. |
| D495,425 S | 8/2004 | Goris et al. |
| 6,783,733 B2 | 8/2004 | Bogen et al. |
| 6,827,901 B2 | 12/2004 | Copeland et al. |
| 6,855,559 B1 | 2/2005 | Christensen et al. |
| 6,930,292 B1 | 8/2005 | Winther et al. |
| 6,943,029 B2 | 9/2005 | Copeland et al. |
| 6,943,035 B1 | 9/2005 | Davies et al. |
| 6,948,843 B2 | 9/2005 | Laugharn, Jr. et al. |
| 7,025,933 B2 | 4/2006 | Ganz et al. |
| 7,250,301 B2 | 7/2007 | Angros |
| 7,270,785 B1 | 9/2007 | Lemme et al. |
| 7,318,913 B2 | 1/2008 | Loeffler et al. |
| 7,378,055 B2 | 5/2008 | Lemme et al. |
| 7,378,058 B2 | 5/2008 | Lemme et al. |
| 7,400,983 B2 | 7/2008 | Feingold et al. |
| 7,584,019 B2 | 9/2009 | Feingold et al. |
| 7,648,678 B2 | 1/2010 | Favuzzi et al. |
| 7,850,912 B2 | 12/2010 | Favuzzi et al. |
| 7,867,443 B2 | 1/2011 | Key et al. |
| 7,875,245 B2 | 1/2011 | Favuzzi et al. |
| 2003/0022391 A1 | 1/2003 | Richards et al. |
| 2003/0124729 A1 | 7/2003 | Christensen et al. |
| 2003/0203493 A1 | 10/2003 | Lemme et al. |
| 2003/0211630 A1 | 11/2003 | Richards et al. |
| 2004/0002163 A1 | 1/2004 | Reinhardt et al. |
| 2004/0029184 A1 | 2/2004 | Gourevitch |
| 2005/0227298 A1 | 10/2005 | Gourevitch |
| 2006/0188396 A1 | 8/2006 | Bedingham et al. |
| 2006/0275861 A1 | 12/2006 | Angros et al. |
| 2006/0275889 A1 | 12/2006 | Angros et al. |
| 2006/0281116 A1 | 12/2006 | Angros et al. |

FOREIGN PATENT DOCUMENTS

| | | |
|---|---|---|
| EP | 0947135 | 4/2005 |
| WO | 9944030 | 9/1999 |
| WO | WO 00/14507 | 3/2000 |
| WO | PCT/US00/18686 | 11/2000 |
| WO | WO 2004/059284 | 7/2004 |
| WO | WO 2006/127852 | 11/2006 |

OTHER PUBLICATIONS

U.S. Appl. No. 60/142,789, filed Jul. 8, 1999, Angros.
U.S. Appl. No. 60/375,679, filed Apr. 26, 2002, Ventana.
"Automated Systems" Brochure, BioGenex 2000.
"Dako® Autostainer Universal Staining System," Brochure, DAKO Corporation, 1999.
"Declere™, One Giant Step Towards Standardization of IHC," Brochure, Cell Marque, 1999.
"Expanding the Power of NexES®", Ventana Brochure, 1998.
"Mark 5 HSS" Promotional Release and Flyer, Diagnostic Products Corporation, 1999.
"MISHA™" Catalog pp. 2-3, Shandon Lipshaw, 1997.
"One Platform. Infinite Possibilities™."Artisan Staining System Brochure, CytoLogix Corporation, 1999.
Pileri et al., "Antigen Retrieval Techniques in Immunohistochemistry: Comparison of Different Methods," Journal of Pathology, 1997, vol. 183:116-123.
"Protocol™ MicroProbe® Staining System for Immunohistochemistry and Special Stains," Fisher Healthcare Brochure, 1998.
Shi et al., "Antigen Retrieval Immunohistochemistry: Past, Present, and Future," J. of Histochemistry & Cytochemistry, 45I3):327-343, 1997.
Shi et al., "Development of an Optimal Protocol for Antigen Retrieval: A 'Test Batter' Approach Exemplified with Reference to the Staining of Retinoblastoma Protein (pRB) in Formalin-Fixed Paraffin Sections," J. of Pathology, 179:347-352, 1996.
Shi et al., "Use of pH 9.5 Tris-HCl Buffer Containing 5% Urea for Antigen Retrieval Immunohistochemistry," Biotechnic & Histochemistry, 71(4):190-195, 1996.
Taylor et al., "Comparative Study of Antigen Retrieval Heating Methods: Microwave, Microwave and Pressure cooker, Autoclave and Steamer," Biotechnic & Histochemistry, 71(5):263-270, 1996.
"TST Stainer Trio" Brochure, Mopec™,—dated prior to 1998.
"Walk-Away Automation for Special Stains and IHC" Brochure, CytoLogix Corporation,—dated prior to 1998.
"Zymed®" Immunohistopathology Catalog, Zymed Laboratories Inc., 1998-1999.
U.S. Appl. No. 11/439,722, Angros et al., Preliminary Amendment, Nov. 13, 2007.
U.S. Appl. No. 11/439,722, Angros et al., Office Action dated Apr. 15, 2008.
U.S. Appl. No. 11/439,722, Angros et al., Amendment and Response to Office Action, Oct. 13, 2008.
U.S. Appl. No. 11/439,722, Angros et al., Office Action Restriction dated Oct. 6, 2009.
U.S. Appl. No. 11/439,722, Angros et al., Amendment and Response to Office Action Restriction dated Apr. 6, 2010.
U.S. Appl. No. 11/439,722, Angros et al., Final Office Action dated Jul. 7, 2010.
U.S. Appl. No. 11/439,722, Angros et al., Amendment and Response dated Aug. 4, 2010.
U.S. Appl. No. 11/439,722, Angros et al., Notice of Allowance dated Aug. 27, 2010.
U.S. Appl. No. 11/439,722, Angros et al., 312 Amendment filed Nov. 15, 2010.

U.S. Appl. No. 11/439,722, Angros et al., Second 312 Amendment filed Nov. 29, 2010.
U.S. Appl. No. 11/439,722, Angros et al., PTO Response to 312 Communication, mailed Dec. 6, 2010.
U.S. Appl. No. 11/439,722, Angros et al., PTO Response to Second 312 Communication, mailed Jan. 28, 2011.
U.S. Appl. No. 11/439,834, Angros et al., Preliminary Amendment, Nov. 13, 2007.
U.S. Appl. No. 11/439,834, Angros et al., Office Action dated Jan. 23, 2009.
U.S. Appl. No. 11/439,834, Angros et al., Amendment and Response dated Jun. 22, 2009.
U.S. Appl. No. 11/439,834, Angros et al., Office Action Restriction dated Oct. 15, 2009.
U.S. Appl. No. 11/439,834, Angros et al., Amendment and Response to Restriction Requirement dated Apr. 16, 2010.
U.S. Appl. No. 11/439,834, Angros et al., Supplemental Amendment and Response dated Sep. 28, 2010.
U.S. Appl. No. 11/439,834, Angros et al., Final Office Action dated Dec. 7, 2010.
U.S. Appl. No. 11/439,834, Angros et al., Response dated Dec. 28, 2010.
U.S. Appl. No. 11/439,834, Angros et al., PTO Advisory Action dated Jan. 13, 2011.
U.S. Appl. No. 11/439,834, Angros et al., Amendment and Response under 1.116 filed Feb. 8, 2011.
U.S. Appl. No. 11/439,834, Angros et al., PTO Notice of Allowance dated Mar. 17, 2011.
Australian Serial 2006249956, Angros et al., Voluntary Amendment dated Nov. 23, 2009.
Australian Serial 2006249956, Angros et al., Office Action dated Feb. 24, 2011.
Brazilian Application No. 0609898-3, Angros et al., Voluntary Amendment dated May 18, 2009.
Canadian Application No. 2,609,453, Angros et al., Voluntary Amendment dated Dec. 9, 2009.
Chinese Application No. 200680026673.8, Angros et al., Voluntary Amendment dated Nov. 30, 2009.
Chinese Application No. 200680026673.8, Angros et al., Office Action dated Feb. 12, 2010.
Chinese Application No. 200680026673.8, Angros et al., Response to Office Action dated Aug. 27, 2010.
Chinese Application No. 200680026673.8, Angros et al., Office Action dated Nov. 24, 2010.
Chinese Application No. 200680026673.8, Angros et al., Amendment and Response filed Apr. 11, 2011.
European Application No. 06771115.0, Angros et al., Voluntary Amendment dated Jan. 20, 2010.
Indian Application No. 9149/DELNP/2007, Angros et al., Voluntary Amendment dated May 19, 2009.
Japanese Application No. 2008-513689, Angros et al., Voluntary Amendment dated May 22, 2009.
Mexican Application No. MX/a/2007/014655, Angros et al., Voluntary Amendment dated Feb. 16, 2010.
Mexican Application No. MX/a/2007/014655, Angros et al., Office Acton dated Mar. 28, 2011.
Russian Application No. 2007146930, Angros et al., Voluntary Amendment dated May 25, 2009.
Russian Application No. 2007146930, Angros et al., Office Action dated May 6, 2010.
Russian Application No. 2007146930, Angros et al., Response to Office Action dated Sep. 17, 2010.
Russian Application No. 2007146930, Angros et al., Office Action dated Nov. 29, 2010.
Russian Application No. 2007146930, Angros et al., Amended Claims filed in Response Jan. 18, 2011.

* cited by examiner

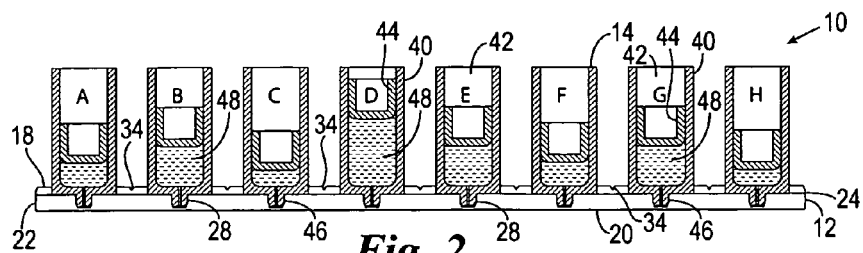
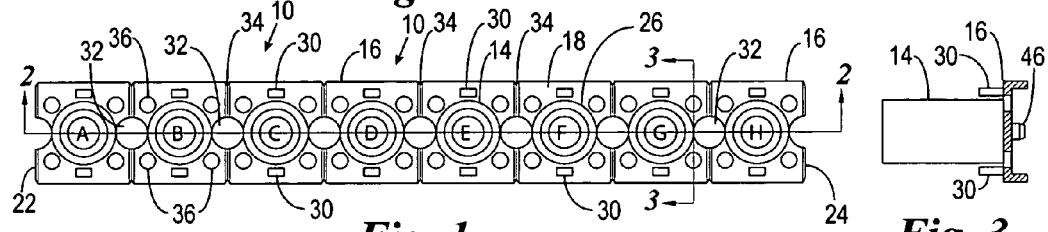
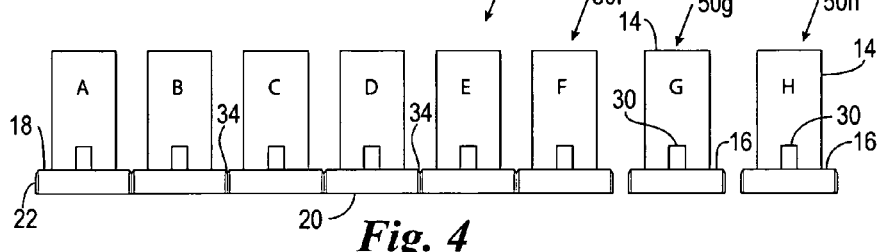
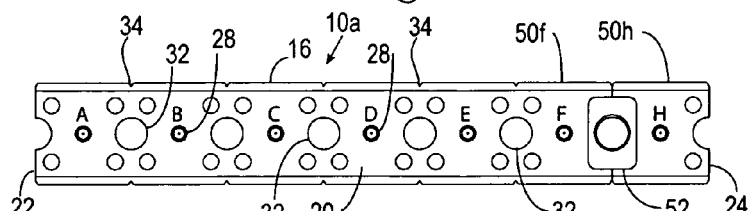
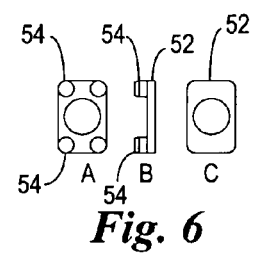
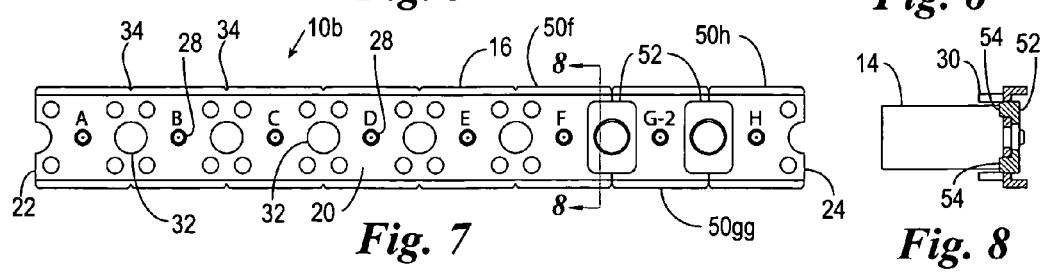

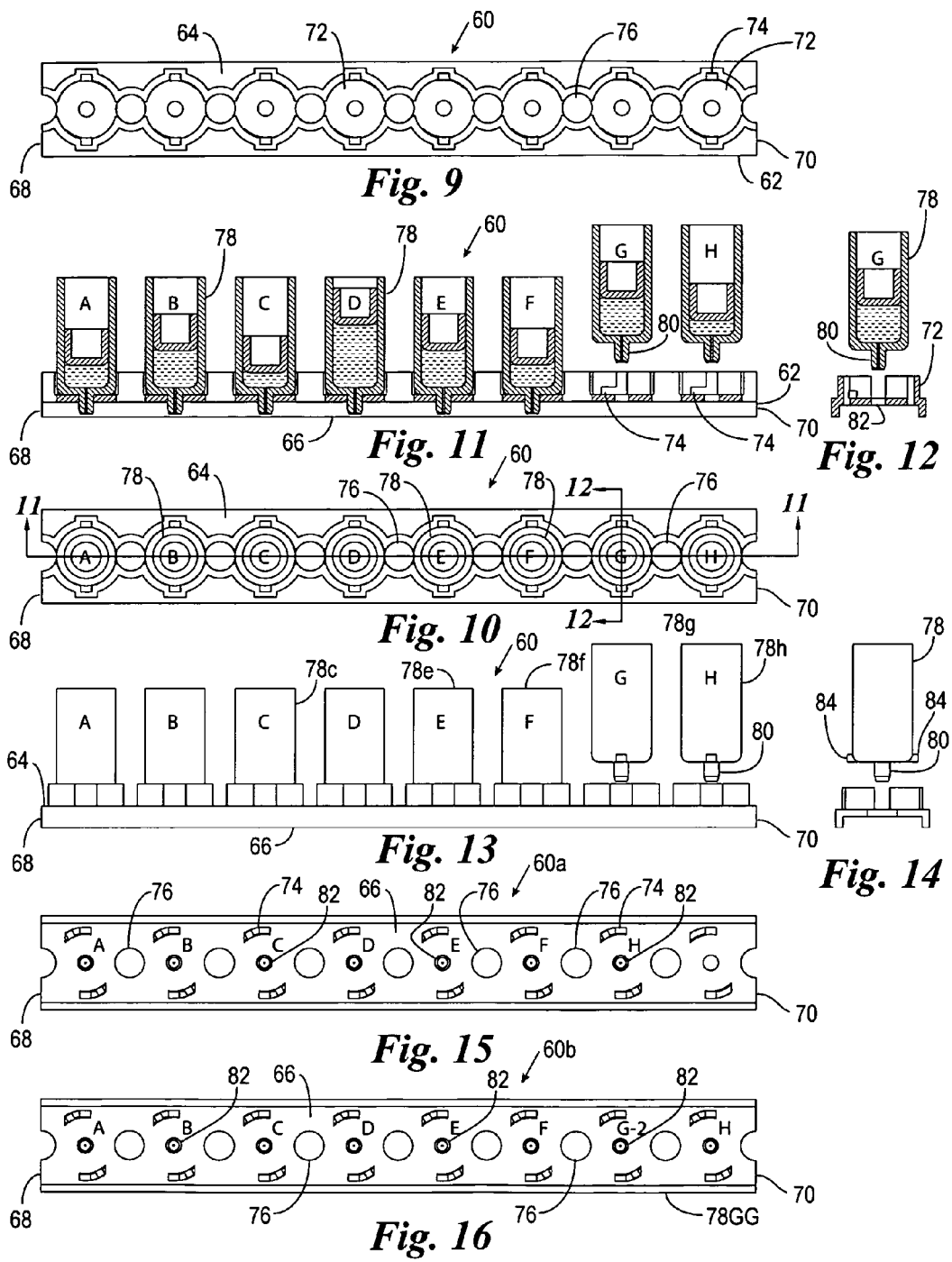

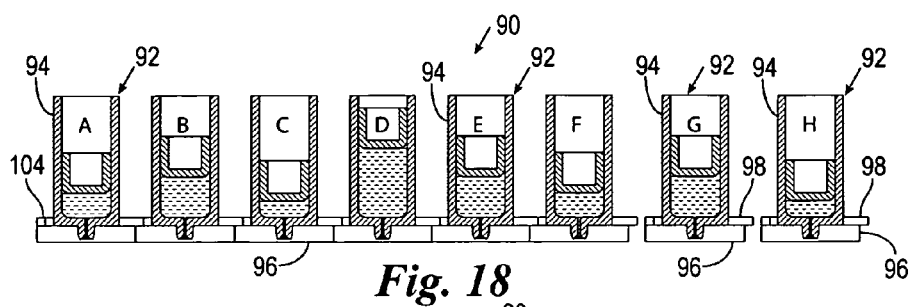
Fig. 18
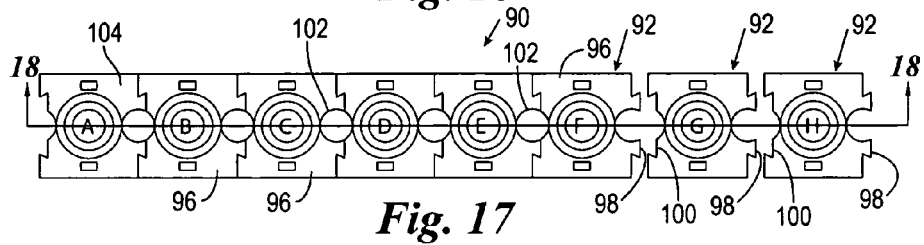
Fig. 17
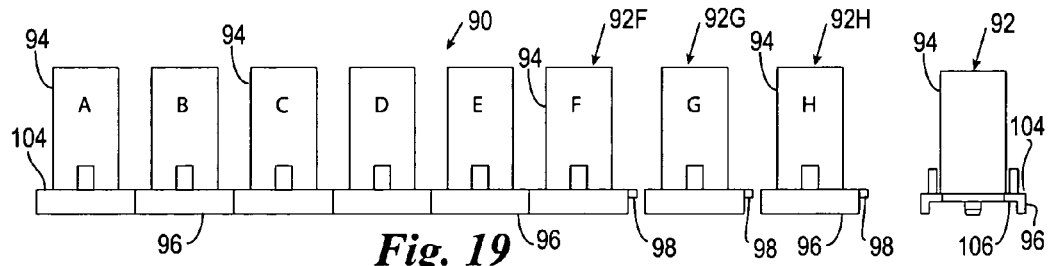
Fig. 19
Fig. 20
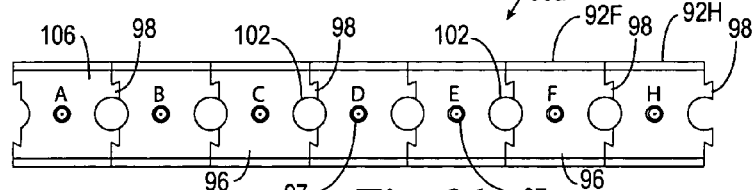
Fig. 21
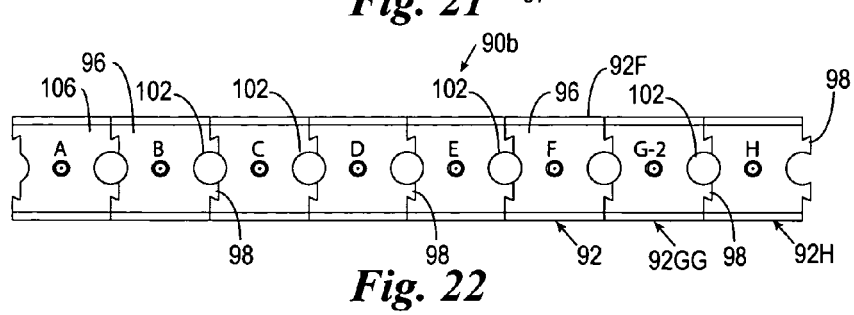
Fig. 22

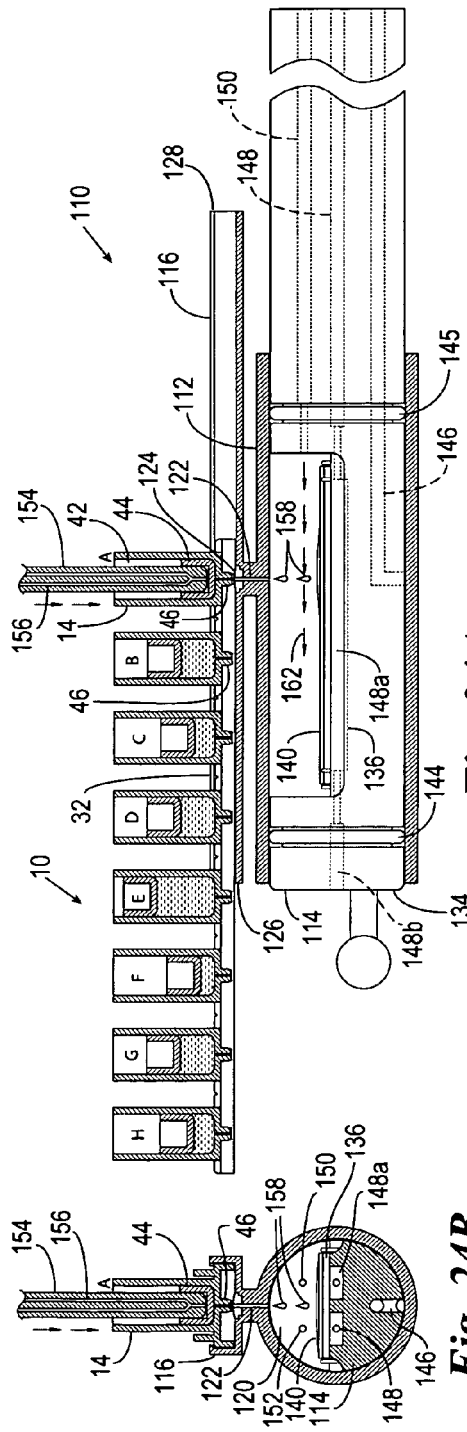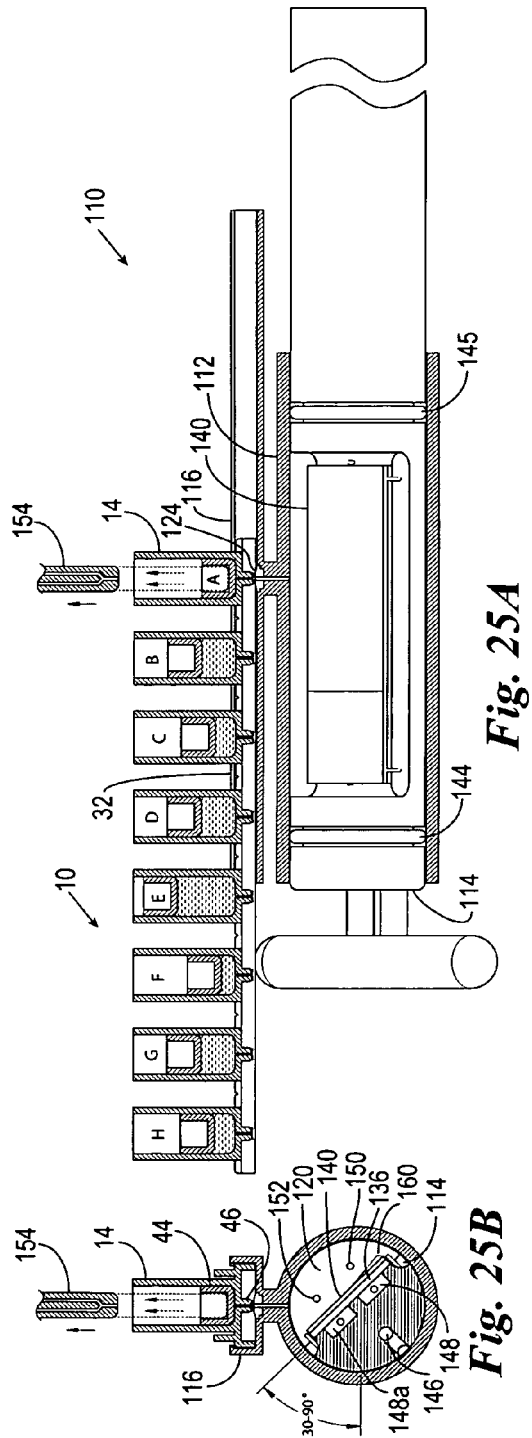

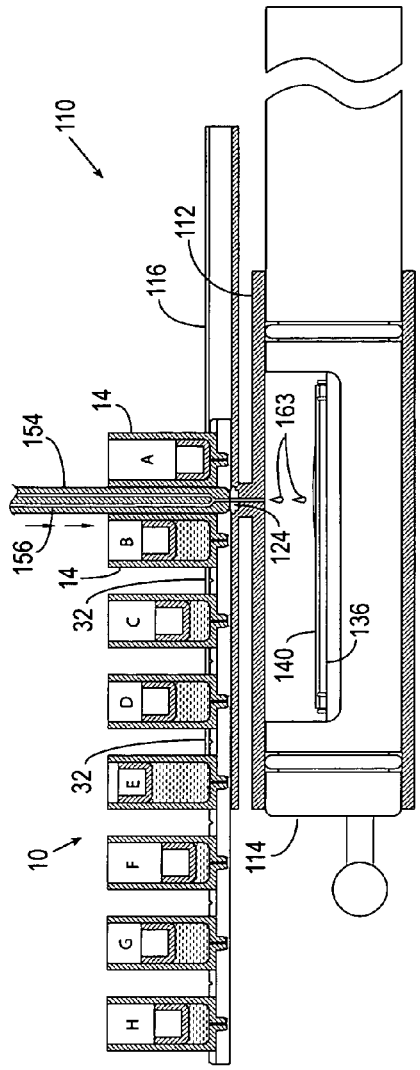
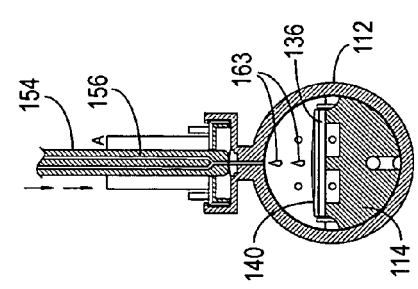
Fig. 26A
Fig. 26B
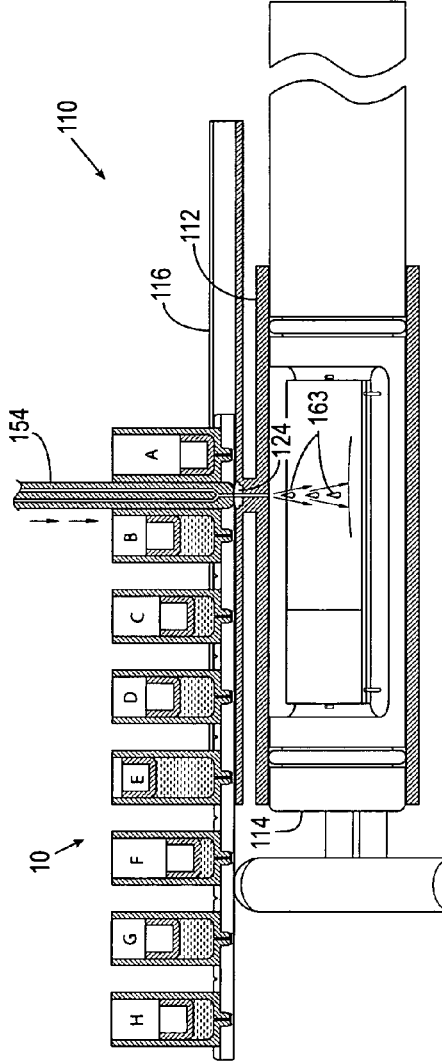
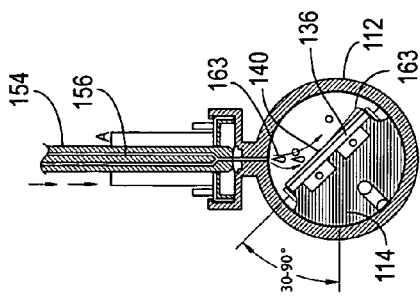
Fig. 27A
Fig. 27B

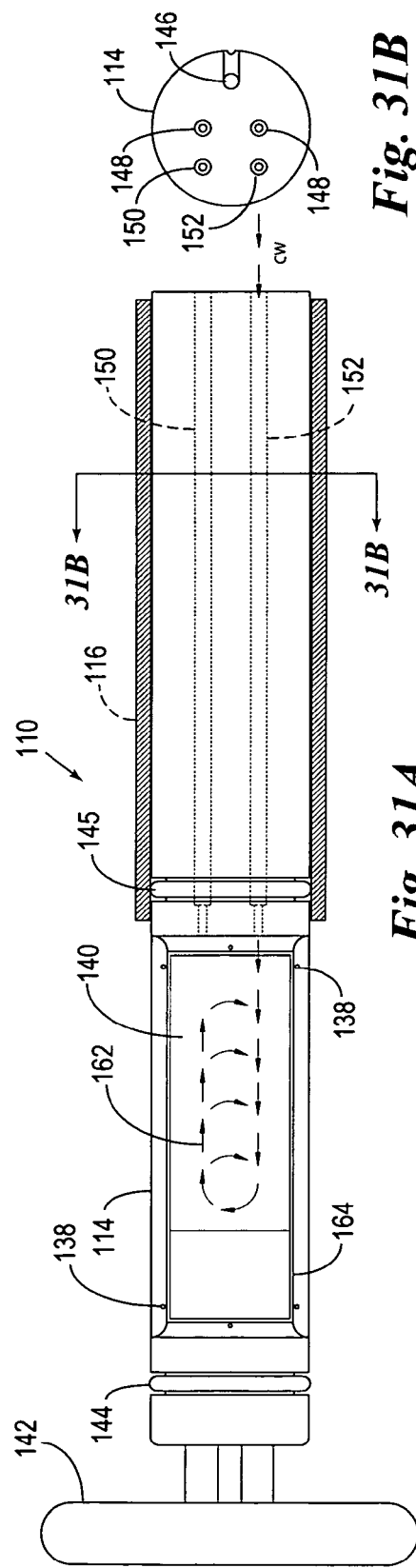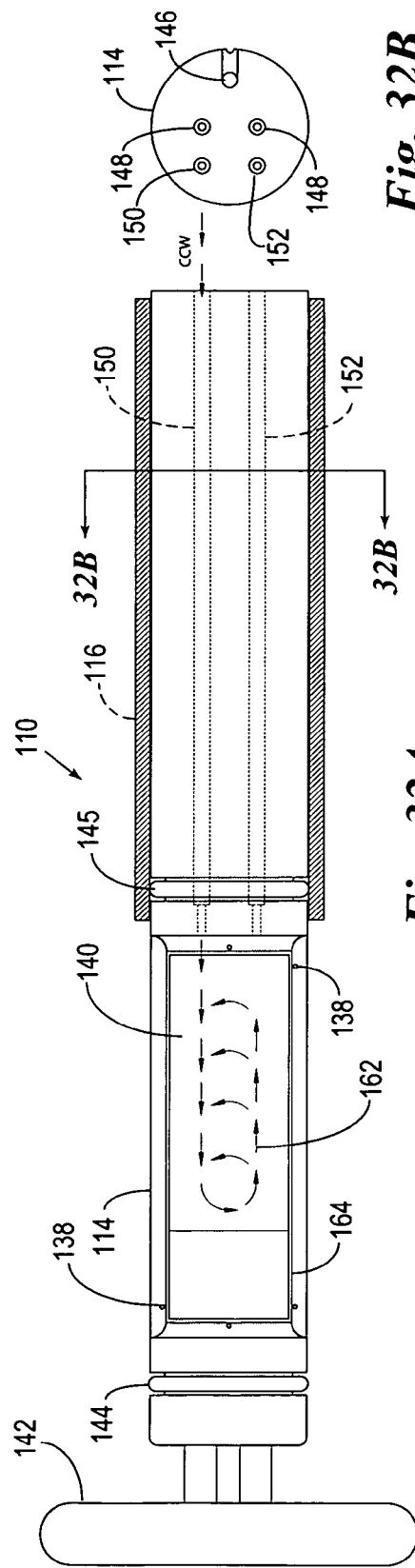

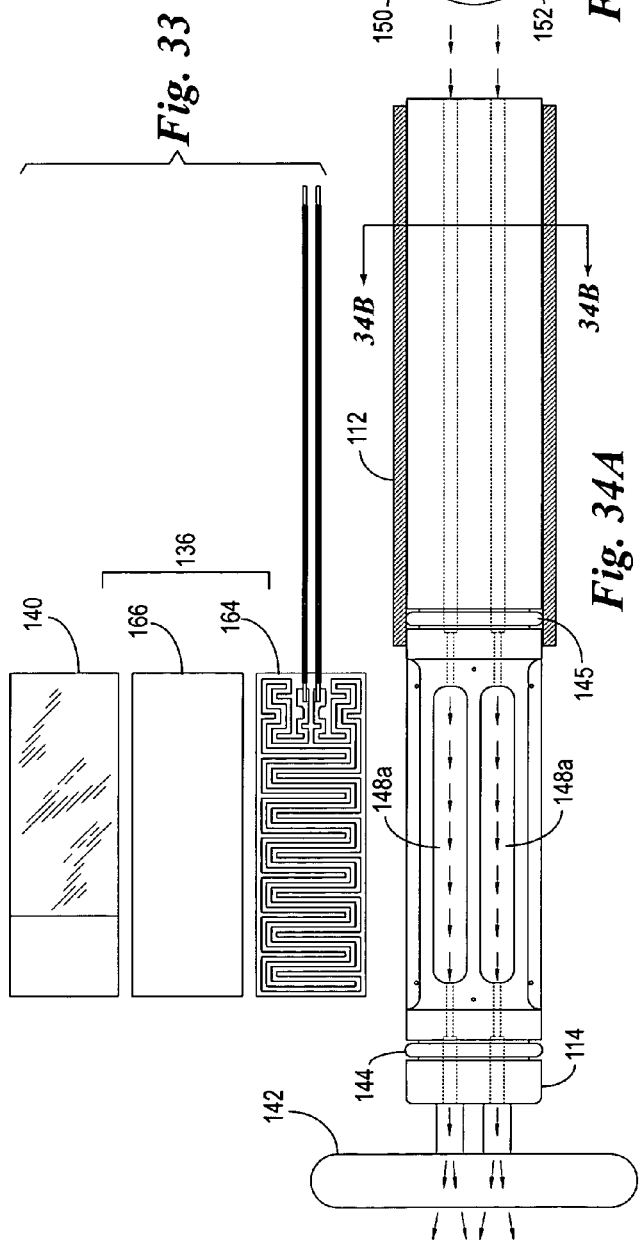

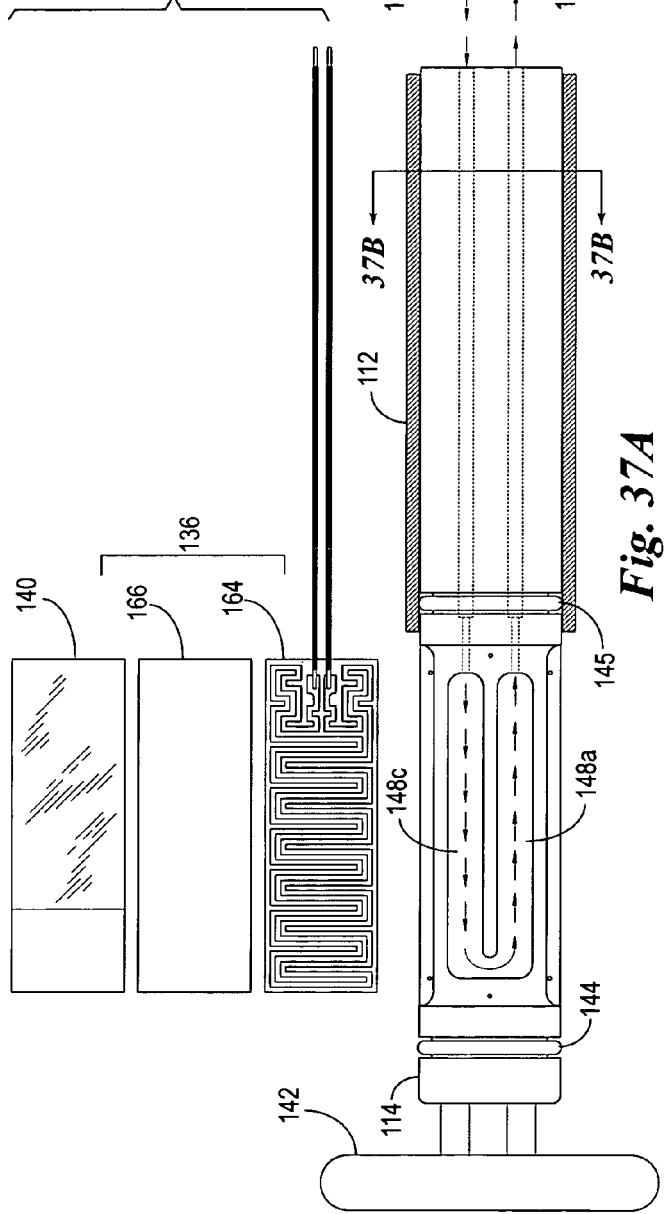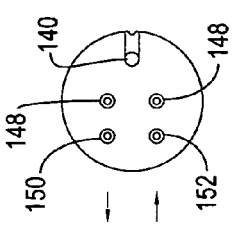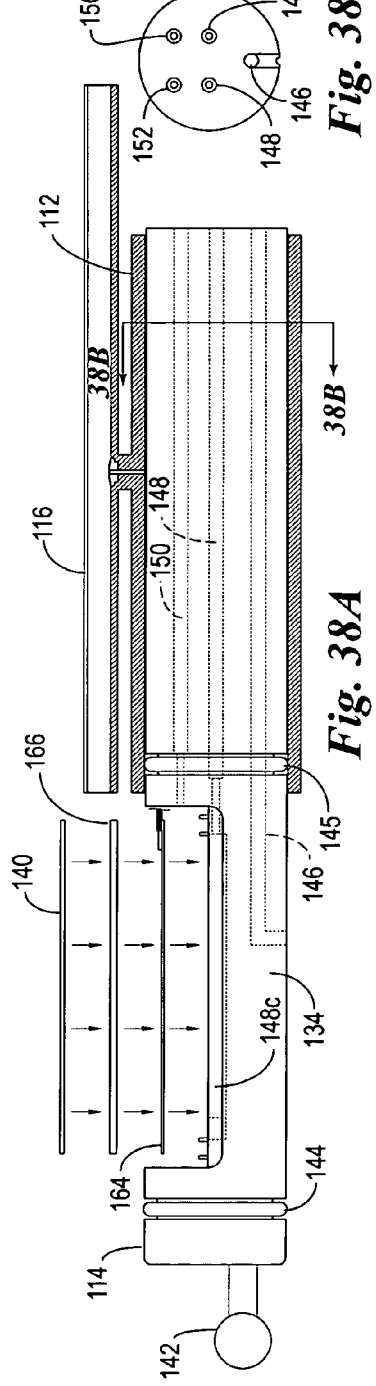

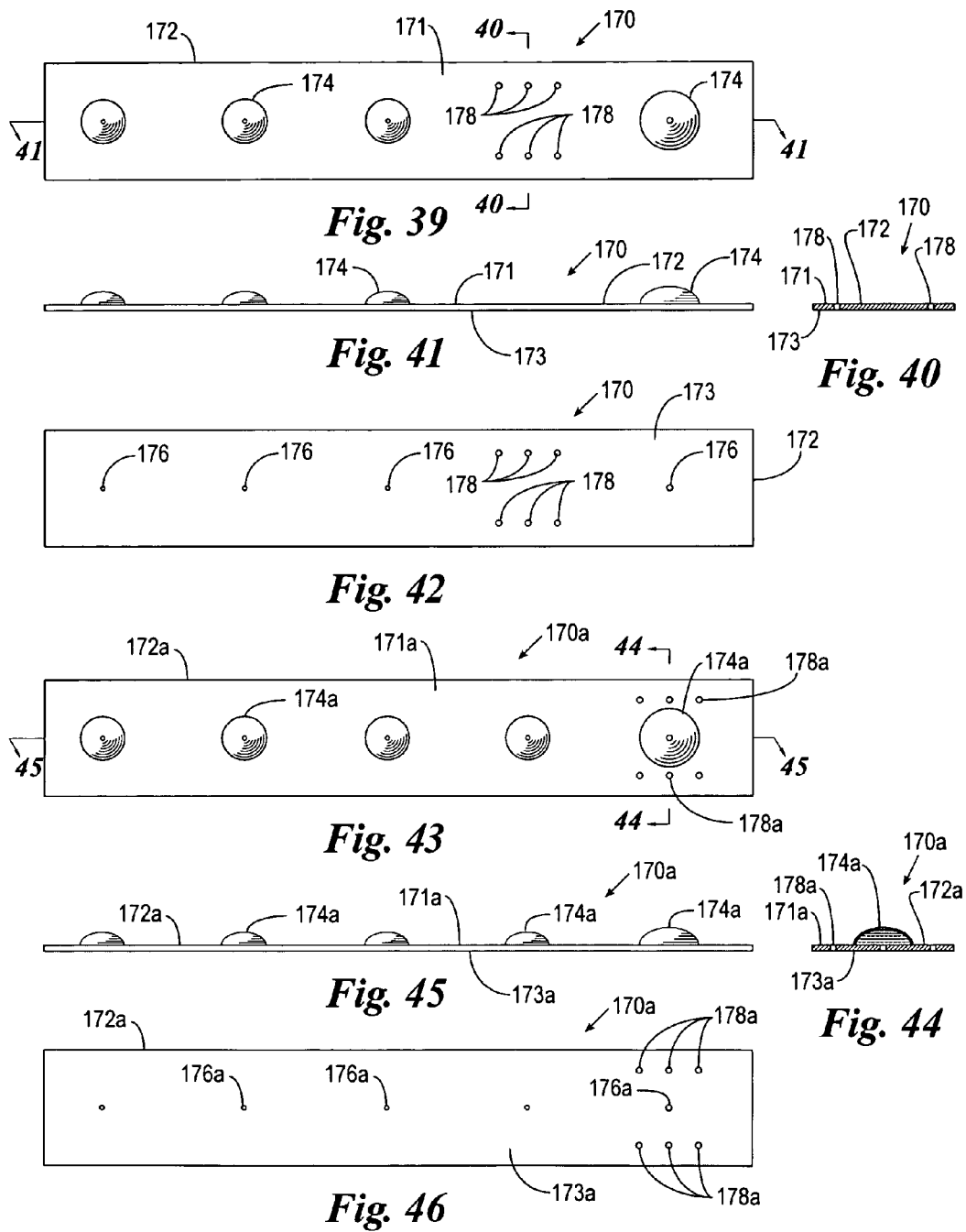

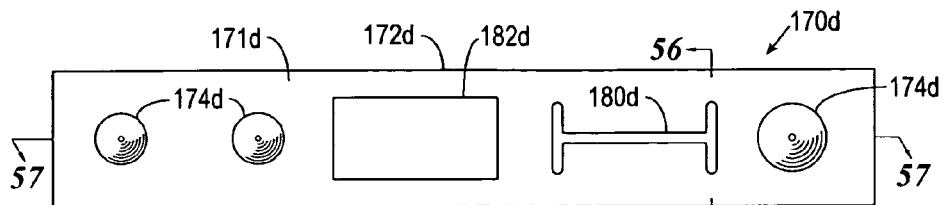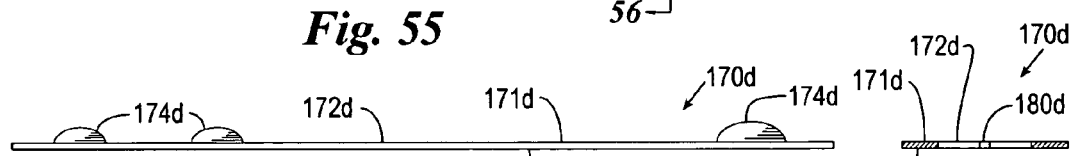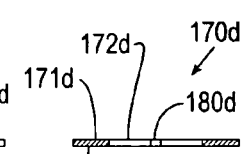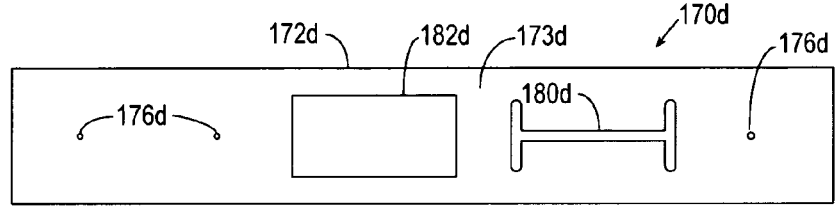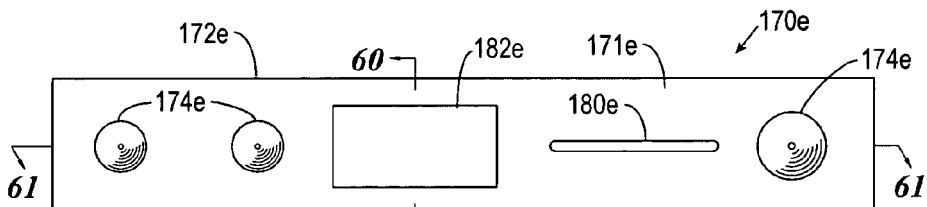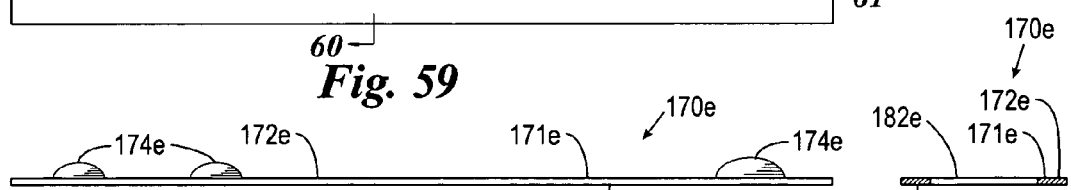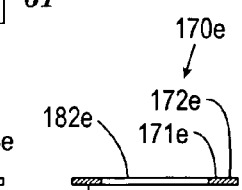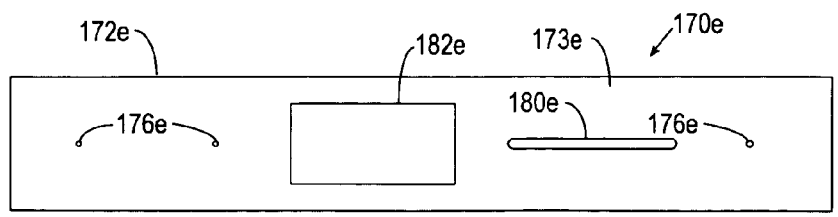

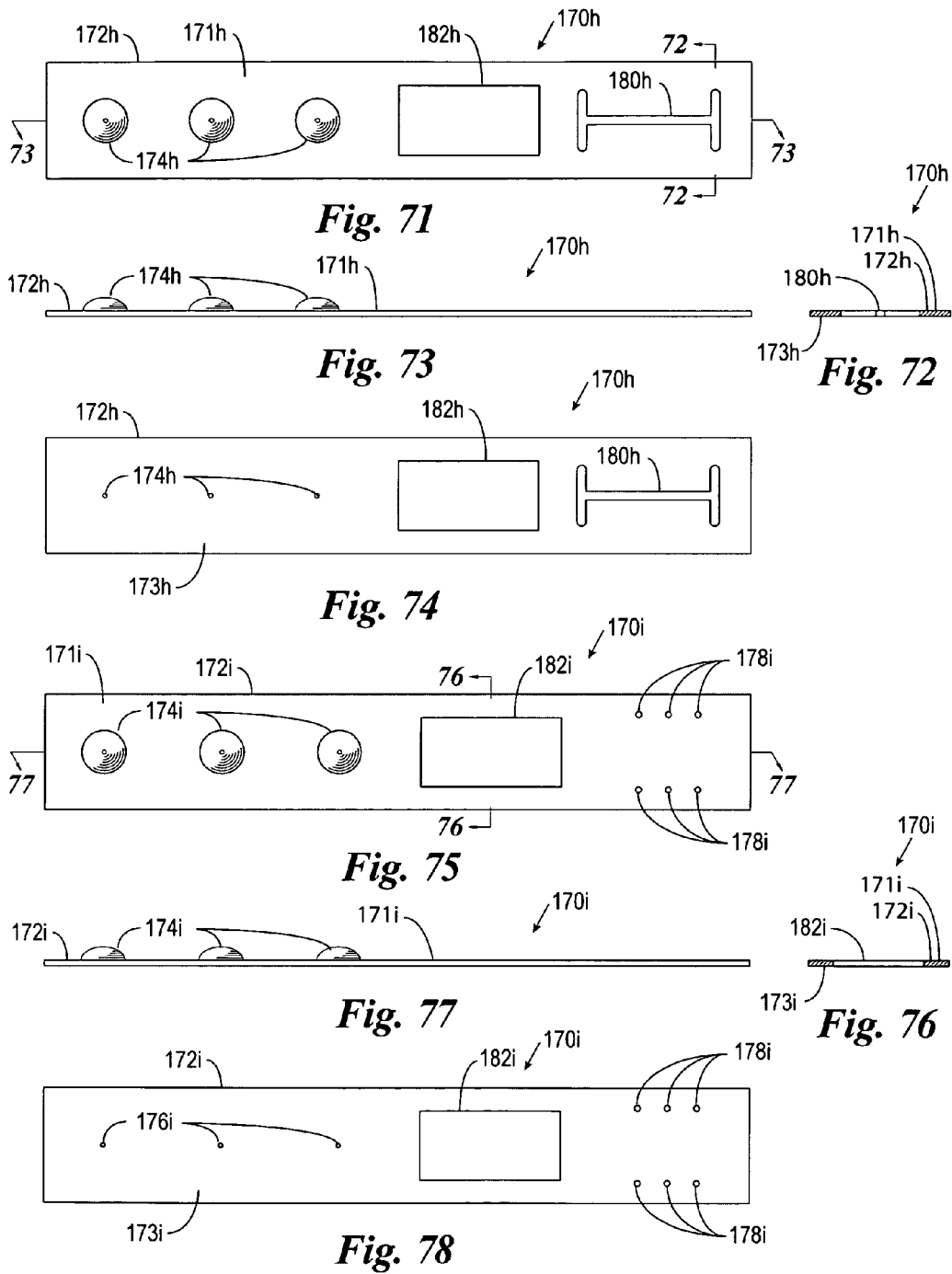

IN SITU HEAT INDUCED ANTIGEN RECOVERY AND STAINING APPARATUS AND METHOD

CROSS-REFERENCE TO RELATED APPLICATIONS

The present application claims benefit under 35 U.S.C. 119(e) of each of U.S. Prov. Appl. Ser. No. 60/684,047 filed May 24, 2005, U.S. Prov. Appl. Ser. No. 60/689,386 filed Jun. 10, 2005, and U.S. Prov. Appl. Ser. No. 60/730,744, filed Oct. 27, 2005, each of which is hereby expressly incorporated by reference herein in its entirety.

STATEMENT REGARDING FEDERALLY SPONSORED RESEARCH OR DEVELOPMENT

Not Applicable.

BACKGROUND

The present invention is related to the field of treating samples on microscope slides including analytical substrates, and more specifically to the field of heat induced antigen recovery and staining.

In anatomical pathology labs (e.g., histology, cytology) it is known that certain immunohistochemical procedures, herein known as IHC assays, are performed on biological specimens including, for example, formalin-fixed paraffin-embedded tissues and cell preps. Also used in the art are several IHC antibodies (abs) like Estrogen receptor abs, Progesterone receptor abs, Proliferation abs like Ki-67, which require the use of high temperature unmasking techniques, (i.e., antigen retrieval, high temperature epitope recovery, and antigen unmasking), prior to application of the antibody for labeling cell structures (antigens).

There are several procedures known in the art for the "unmasking" of antigens that have been rendered "hidden" by formalin fixation. Procedures known in the art include treating the biological specimen in aqueous solutions (e.g., water) that may include buffers (e.g., citrate, EDTA, urea, etc.), along with detergents or surfactants (e.g., Brij 35, Tween, SDS, NP-40 and Igepal). These known formulations are heated to temperatures from around 60° C. to about 120° C. These heated formulations are in contact with the biological specimen for various amounts of time (e.g., about 10 minutes to about 90 minutes) thereby causing the "masked" antigen to become "unmasked" so the antibodies used in the IHC assays can attach to their corresponding antigens which are associated with the biological specimen.

Types of apparatuses that are known and used to perform the heating of the antigen retrieval solutions and the biological specimen include waterbaths, steamers, pressure cookers, autoclaves, microwave ovens and convection ovens. Since water boils at 100° C. at normal atmospheric pressure, antigen retrieval solutions even with other chemicals present have only been able to reach temperature from about 98° C. to 100° C. before evaporative heat loss inhibits the solution from reaching higher temperatures. Pressure cookers and autoclaves overcome this by allowing for pressurization of the solutions so higher temperatures can be achieved without evaporation of the heated fluid. Since there are antibodies that require the antigen retrieval solution be at temperatures exceeding 100° C., many laboratories must use pressure cookers to heat the biological specimen with its antigen retrieval solution to attain temperatures up to 120° C., without which the antigen would not be "unmasked" preventing the antibody from binding to the antigen.

There remains a need for an apparatus able to produce high temperature pressure conditions for single slides being subjected to individualized antigen retrieval conditions without relying on clumsy and unwieldy devices such as pressure cookers and autoclaves.

BRIEF DESCRIPTION OF THE DRAWINGS

FIG. 1 is a top plan view of a reagent strip (reagent dispensing strip) of the present invention.

FIG. 2 is a cross-sectional side view taken through line 1-1 of the reagent dispensing strip of FIG. 1.

FIG. 3 is a cross-sectional view along line 3-3 of FIG. 2.

FIG. 4 is a side view of the reagent strip of FIG. 1 having two reagent modules detached therefrom.

FIG. 5 is a bottom plan view of the reagent strip of FIG. 1 with a reagent module reattached via a tile connector.

FIG. 6 is a top plan view (A), side view (B), and bottom plan view (C) of the tile connector used in FIG. 5.

FIG. 7 is a bottom plan view of a reagent strip with two reagent modules reconnected via a pair of tile connectors.

FIG. 8 is a cross-sectional view taken through line 8-8 of a reagent module and tile connector.

FIG. 9 is a top plan view of a base of another reagent strip of the present invention.

FIG. 10 is a top plan view of the reagent strip of FIG. 9 with reagent containers disposed upon the base.

FIG. 11 is a cross-sectional side view taken through line 11-11 of FIG. 10.

FIG. 12 is a cross-sectional view taken through line 12-12 which shows how a reagent container fits onto or is removed from the base of the reagent strip of FIG. 11.

FIG. 13 is a side view of the reagent strip of FIG. 11.

FIG. 14 is a front end view of the reagent strip of FIG. 13.

FIG. 15 is a bottom plan view of the reagent strip of FIG. 10 after the "G" reagent container has been removed and the "H" reagent container has been moved into the former "G" position.

FIG. 16 is a bottom plan view of the reagent strip of FIG. 10 after the "G" reagent container has been replaced with a "G-2" reagent container.

FIG. 17 is a top plan view of another reagent strip of the present invention which has exchangeable reagent modules.

FIG. 18 is a cross-sectional view taken through line 18-18 of FIG. 17.

FIG. 19 is a side view of the reagent strip of FIG. 17.

FIG. 20 is a front end view of the reagent strip of FIG. 19.

FIG. 21 is a bottom plan view of the reagent strip of FIG. 17 after reagent module "G" has been removed.

FIG. 22 is a bottom plan view of the reagent strip of FIG. 17 after the reagent module "G" has been exchanged with reagent module "G-2".

FIG. 24A is a cross-sectional side view of the reaction module of FIG. 23 in operation in a reagent dispensing phase.

FIG. 24B is a transverse cross-sectional view of the reaction module of FIG. 24A.

FIG. 25A is a cross-sectional side view of the reaction module of FIG. 23 and FIG. 24A in a reagent drainage phase.

FIG. 25B is a transverse cross-sectional view of the reaction module of FIG. 25A.

FIG. 26A is a cross-sectional side view of the reaction module of FIG. 25A in a rinse buffer dispensing phase.

FIG. 26B is a transverse cross-sectional view of the reaction module of FIG. 26A.

FIG. 27A is a cross-sectional side view of the reaction module of FIG. 26A in a rinse buffer drainage phase.

FIG. 27B is a transverse cross-sectional side view of the reaction module of FIG. 27A.

FIG. 31A is a cross-sectional top view of the reaction compartment and slide support element of the reaction module of FIG. 29 which shows a clockwise air mixing step.

FIG. 31B is a transverse cross-sectional view of the air ports of the slide support element of FIG. 31A.

FIG. 32A is a cross-sectional top view of the reaction compartment and slide support element of the reaction module of FIG. 29 which shows a counter-clockwise air mixing step.

FIG. 32B is a transverse cross-sectional view of the air ports of the slide support element of FIG. 32A.

FIG. 33 is a view of the slide and detached components of the heating element of the slide support element of FIG. 28.

FIG. 34A is a cross-sectional top view of a slide support of a reaction module element with the slide and heating element detached to show air flow through the air cooling ducts which are used to enhance a rapid cooling of the heating element.

FIG. 34B is a transverse cross-sectional view through the air cooling ducts of the slide support element of FIG. 34A.

FIG. 35A is a cross-sectional side view of the reaction module of FIG. 34A.

FIG. 35B is a transverse cross-sectional view through the air cooling ducts of the slide support element of FIG. 35A.

FIG. 36 is a view of the slide and detached components of the heating element of the slide support element of FIG. 28.

FIG. 37A is a cross-sectional top view of a slide support of a reaction module element with the slide and heating element detached to show air flow through the air cooling ducts which are used to rapidly cool the heating element.

FIG. 37B is a transverse cross-sectional view through the air cooling ducts of the slide support element of 37A.

FIG. 38A is a cross-sectional side view of the reaction module of FIG. 34A.

FIG. 38B is a transverse cross-sectional view through the air cooling ducts of the slide support element of FIG. 38B.

FIG. 39 is a top plan view of an alternate version of the reagent strip of the present invention, the reagent strip having ventilation holes.

FIG. 40 is a cross-sectional view of the reagent strip of FIG. 39 taken through line 40.

FIG. 41 is a side view of the reagent strip of FIG. 39.

FIG. 42 is a bottom plan view of the reagent strip of FIG. 39.

FIG. 43 is a top plan view of an alternate version of the reagent strip of the present invention, the reagent strip having ventilation holes.

FIG. 44 is a cross-sectional view of the reagent strip of FIG. 43 taken through line 44.

FIG. 45 is a side view of the reagent strip of FIG. 43.

FIG. 46 is a bottom plan view of the reagent strip of FIG. 43.

FIG. 55 is a top plan view of an alternate version of the reagent strip of the present invention, the reagent strip having a ventilation slot and a rapid cooling window.

FIG. 56 is a cross-sectional view of the reagent strip of FIG. 55 taken through line 56.

FIG. 57 is a side view of the reagent strip of FIG. 55.

FIG. 58 is a bottom plan view of the reagent strip of FIG. 55.

FIG. 59 is a top plan view of an alternate version of the reagent strip of the present invention, the reagent strip having a ventilation slot and a rapid cooling window.

FIG. 60 is a cross-sectional view of the reagent strip of FIG. 59 taken through line 60.

FIG. 61 is a side view of the reagent strip of FIG. 59.

FIG. 62 is a bottom plan view of the reagent strip of FIG. 59.

FIG. 71 is a top plan view of an alternate version of the reagent strip of the present invention, the reagent strip having a ventilation slot and a rapid cooling window.

FIG. 72 is a cross-sectional view of the reagent strip of FIG. 71 taken through line 72.

FIG. 73 is a side view of the reagent strip of FIG. 71.

FIG. 74 is a bottom plan view of the reagent strip of FIG. 71.

FIG. 75 is a top plan view of an alternate version of the reagent strip of the present invention, the reagent strip having ventilation holes and a rapid cooling window.

FIG. 76 is a cross-sectional view of the reagent strip of FIG. 75 taken through line 76.

FIG. 77 is a side view of the reagent strip of FIG. 75.

FIG. 78 is a bottom plan view of the reagent strip of FIG. 75.

DETAILED DESCRIPTION OF THE INVENTION

Figure 23:
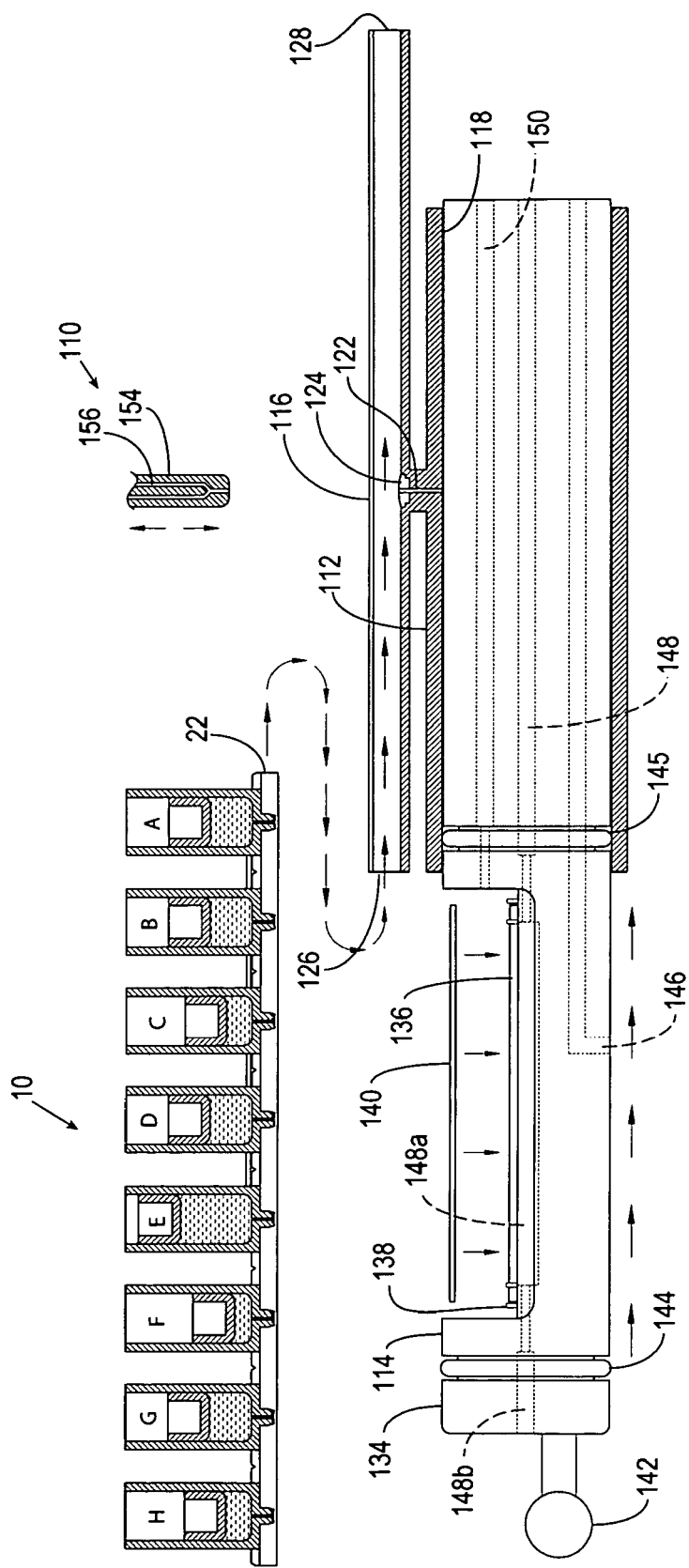
FIG. 23 is a cross-sectional side view of a reaction module (reaction compartment, slide, support element, and reagent strip support device) of the present invention before the reagent strip has been inserted into the reagent strip support device, and before a microscope slide has been disposed on the slide support element.

Contemplated herein is an automated microscope slide staining apparatus that features a plurality of individually operable miniaturized pressurizable reaction compartments for individually and independently processing a plurality of individual microscope slides (where used herein the term "microscope slide" is also intended to refer to other microscopy analytical devices which are used as vessels or support structures for supporting biological and biochemical specimens for testing and analysis, and which are sized and shaped to fit within a reaction compartment as described and contemplated herein and which include, but are not limited to, test tubes, petri dishes, and microarray plates, as well as standard microscope slides). The automated in-situ antigen recovery and staining apparatus of the present invention preferably features independently movable slide support elements each having an individually heatable heating plate. Each slide support element preferably supports a single microscope slide. Each slide support element with the microscope slide thereon is enclosed within its own individual pressurizable reaction compartment and/or comprises a portion thereof. In one treatment step, antigen retrieval solution is disposed on the slide and the heating plate heats the slide and the antigen retrieval solution thereon to temperatures of up to and in some cases exceeding 150° C. by regulating the pressure within the reaction compartment thereby increasing the temperature that the solution can attain. In one embodiment each reaction compartment has its own individual pressure regulator, device, or switch to regulate pressure within the reaction compartment. Pressures exceeding 1 atm (i.e., exceeding 14.7 psi, 0 psig or 101.325 kPa) or below 1 atm can be created and maintained in the reaction compartment. The reaction compartment can hold, for example, 0.1 ml to 100 ml of antigen retrieval solution.

Where used herein the term "biological specimen" includes, but is not limited to, unprocessed specimens, processed specimens, paraffin embedded tissue, whole mounts, frozen sections, cell preps, cell suspensions, touch preps, thin preps, cytospins, and other biological materials or molecules including blood, urine, cerebrospinal fluids, pleural fluids, ascites fluids, biopsy materials, fine needle aspirates, pap smears, swabbed cells or tissues, microbiological preps including bacteria, viruses, parasites, protozoans, biochemicals including, but not limited to proteins, DNA, RNA, carbohydrates, lipids, microarrays, ELISA reagents and analytes, synthetic macromolecules, phospholipids, support structures of biological molecules (e.g., metals, beads, plastics, polymers, glass), or any other materials attached to a biological testing substrate for processing, examination, or observation.

Because of the ability to pressurize and regulate pressure within the reaction compartment, and to individually heat each slide, each slide and a liquid solution or reagent thereon (e.g., including, but not limited to, antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives) can be heated to temperatures that could not be obtained without the enclosed pressurized environment of the reaction compartment. For example, since the vapor produced by the solution is contained in the reaction compartment (or is released in a regulated manner), the pressure in the reaction compartment can be regulated to produce a temperature required by the user. Pressures ("negative pressure", i.e., vacuums) below 1 atm (i.e., below 14.7 psi, 0 psig or 101.325 kPa) may also be created and maintained within the reaction compartment. For example, vacuum pressures of from 100 kPa to 10 kPa to 1 kPa to 100 Pa to 10 Pa to 1 Pa to 0.1 Pa may be formed and held in the reaction compartment.

Each reaction compartment of each reaction module can be heated separately and independently from the other reaction compartments by a conductive heating element (or heating plate) underneath or adjacent to the slide (e.g., wherein the heating element is in a sidewall of the reaction compartment or in a cavity). In a preferred embodiment, as noted above, the enclosed reaction compartment containing at least a portion of the microscope slide has an antigen retrieval solution deposited onto the slide in the reaction compartment. The slide is then heated, in a preferred embodiment, to a temperature of about 100° C.-300° C. and under a pressure from 0.1 psig (102.016 kPa) to 350 psig (2514 kPa). In one embodiment the containment of the pressure is proportional to the temperature of the antigen retrieval solution, such that the regulation of both the temperature of the heating element of the reaction compartment and the regulation of the pressure generated by the solution on the slide can be adjusted during the automated staining procedure.

In one example, the heating element could heat the slide to at least 120° C. and the pressure in the reaction compartment would be 16 psig wherein, the solution on the slide in contact with the biological specimen would be about 130° C. It would be apparent to one of ordinary skill in the art of pressure regulated vessels that the temperature attained by the antigen retrieval solution would be dependent on the regulation of either the pressure generated or the temperature of the heating element or both. If regulation of the temperature of the solution is to be determined by the pressure, the heating plate can be set at 130° C. (for example) and the pressure relief valve could be set to a level to maintain a pressure of 19 psig (232.3 kPa) within the reaction compartment, for example. Thus, the temperature of the antigen retrieval solution would not exceed 130° C. and would remain in the range of 120° C.-130° C.

If regulation of the temperature of the solution is determined by temperature of the heating element, then the heating plate can be regulated to heat up to a desired temperature. Once the desired pressure within the reaction compartment has been reached, the heating element pressurizing means are adjusted to keep the desired pressure within the preferred limits. The reaction compartment under some conditions does not necessarily require a pressure regulator since the pressure in the reaction compartment was regulated solely by the temperature of the heating element. In some embodiments it would be advantageous to have a regulator to relieve pressure if the pressure exceeds desired levels or to have a pressure regulator which would cause the heating element to be turned on and off depending on the desired pressure.

Since boiling of the solution on the slide is suppressed by the containment of the pressure, the antigen recovery buffer in the reaction compartment may appear not to be boiling even though it has actually reached a temperature above 100° C. Elimination or reduction of vapor loss due to boiling is advantageous because it removes the necessity of adding additional buffer during processing (such as is necessary when using certain other apparatuses known in the art, e.g., as shown in U.S. Pat. Nos. 5,654,200; 5,595,707; 6,296,809; 6,352,861; 6,582,962; 6,096,271; 6,180,061; 6,183,693; 6,541,261; or 6,783,733) even when only small amounts of buffers are initially used (e.g., 500 µl-4 ml) and treatment times are extended up to 60 minutes at high temperatures (e.g., 130° C.). Loss of antigen retrieval volume in the present invention is minimal due to containment of vapors generated. Another important advantage to minimization of boiling at high temperatures is that the biological specimen on the slide is not subjected to extreme agitation from bubbles being formed which could cause the biological specimen to detach from the glass slide or be otherwise damaged. Moreover, the controlled pressurized micro-environment in the reaction compartment of the present invention is very efficient because the amount of buffer that is used is minimal and the amount of time needed to heat to high heat conditions (e.g., 120° C.-140° C.) is also minimal (e.g., 5 minutes).

Commercial pressure cookers which are currently available for use in antigen retrieval procedures are bulky and require a greater amount of buffer and time to complete the high temperature antigen retrieval process and furthermore must be used to treat many slides in the same container. The typical pressure cooker procedure from start time to the last step (rinse) typically lasts 45-60 minutes. Only a few different buffers can be heated at the same time, (on the order of 5-6 separate slide treatment containers) within a pressure cooker's main reaction compartment. Each separate slide container in a commercial pressure cooker requires significant volumes of antigen retrieval solution (e.g., 45-50 mls per container). As opposed to the pressure cookers which are used in the field of antigen retrieval, the apparatus and method of the present invention preferably uses vapor from the reagent on the slide itself to produce an elevated pressure in the individual reaction compartment. Pressure cookers, to the contrary, rely on a separate liquid present within the bottom of the vessel to produce the vapor necessary to cause increased pressure within the vessel for inducing antigen retrieval on the slides therein. This method requires the additional step of heating the separate liquid to an elevated temperature before the process of heating the slide and the reagent thereon can begin.

Each of the individual reaction compartments of the apparatus of the present invention, to the contrary, utilize relatively small quantities of antigen retrieval buffer (e.g., 0.5-5 ml per slide) and heat up quickly and cool quickly due to the small amounts of liquid and area to be heated and cooled. Even a volume of 0.1-1 ml per slide can be used with the present invention and the typical time from start to finish using the present invention can be as low as 20 minutes, for example.

In a preferred embodiment of the invention, to maintain small amounts of liquid reagents (e.g., including, but not limited to antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives) from being reduced in volume by the conversion from a liquid phase to a gaseous phase, and loss thereof, during heating (as occurs in other commercially available systems), the reaction compartment, when closed, can be pre-pressurized, individually, prior to the heating of the slide and reagent. This pre-pressurization from a separate pressurization source, (i.e., rather than solely from the vapor pressure produced by the heated liquid), can significantly reduce the amount of loss of the gaseous phase (evaporation) of small amounts of liquid reagents (e.g.,100 µl-4 ml) under high temperature conditions (e.g., 100° C.-140° C.) for extended heating times (e.g., 10-60 minutes), thereby eliminating the requirement of adding additional reagent after the treatment process has begun. For example, preferably, 0.1-4 milliliters of reagent (e.g., antigen retrieval reagent) is placed on the slide, the reaction compartment is then pre-pressurized and then the heating element begins to heat the reagent. The pre-pressurization of the reaction compartment, followed by heating of the reagent, produces an environment for the reagent to reach temperatures exceeding 100° C., for example up to 140° C., with minimal reagent loss due to gas phase formation (evaporation).

As is apparent from the above example, the temperatures and pressures could alternatively be set for any desired level for any protocol known in the art of staining biological specimens. Super high temperature conditions can also be achieved using the present invention. These super high heating conditions can reach and exceed 350° C. and 300 psig (2170 kPa) due to pressurization, pre-pressurization, and the particular construction of the reaction compartment (described below). The individual pre-pressurizable reaction compartments of the present invention can hold any type of vessel or substrate known in the art for containing a biological specimen for testing. Vessels or substrates include but are not limited to glass and plastic microscope slides, micro titer plates, tubes, flasks, micro arrays, vials, plates, and other vessels for containing biological materials.

In a preferred embodiment, the reaction compartment can be pre-pressurized and remain pressurized even under very high pressures of over 300 psig (2170 kPa) to produce very high temperatures exceeding 300° C. for use in special procedures that require such very high temperature conditions. In alternate embodiments, the reaction compartment can generate and sustain temperatures and pressures, for high heat conditions, in the range of 100 to 150° C. to 200° C.-250° C. to 300° C. Preferably, a pressure of at least 15 psig (204.7 kPa) is maintained within the reaction compartment during heating.

As described elsewhere herein, this heat can be generated by a conductive heating element positioned beneath the microscope slide, a conductive heating element in the reaction compartment wall, other types of heating devices in locations adjacent to the reagents being heated, and microwaves passing through the walls of the reaction compartment to heat the regents, for example. These types of heating devices can all be incorporated separately or together with the systems described herein for the regulation of pressure.

In a preferred embodiment, the regulation of pressure within the reaction compartment, either by pre-pressurization or by pressure produced by evaporation of the heated reagent, is a critical component of the invention.

In a preferred embodiment the present invention eliminates the use of a single large container (e.g., a pressure cooker) to treat one or a plurality of slides under pressure. Each individually operable reaction compartment of the apparatus of the present invention can treat an individual slide disposed therein with an individualized reagent at an individualized temperature and pressure without relying on or affecting any of the other plurality of slides in their respective reaction compartments in the same apparatus, i.e., each reaction compartment can operate independently of each other reaction compartment. The advantage of the present invention is in its ability to treat every slide in the instrument separately and independently at an individualized temperature and pressure without reliance on any other processing devices of the other reaction compartments thereby increasing efficiency in the production and processing of specimens and providing a constant workflow advantage. Using the present invention, a technician can separately begin a test of a slide utilizing any protocol at any temperature or pressure without affecting or stopping the other reaction compartment even when those other reaction compartments are already in use.

As described above, the temperature of the reagent on or in the slide (or vessel) in the reaction compartment can be maintained by regulating the temperature of the heating element or by regulating the pressure by a pressure regulator or by both in combination. In one embodiment, for example, the reaction compartment can be pre-pressurized to 23 psig (259.9 kPa), the heating element can be set to reach 125° C., and the maintenance pressure can be set to 23 psig (259.9 kPa), wherein the reagent on the slide reaches a temperature of 125° C. for 10 minutes, and is then cooled for further processing. In a preferred embodiment, the pre-pressurized conditions are defined as "separately pressurizing a reaction compartment that has a biological specimen contained therein." In this embodiment, as noted above, the pressure is not produced by the vaporization of the liquid contained in the reaction compartment, but rather by a separate pressurization system or device. The reaction compartment can hold one individual biological specimen or can also hold several biological specimens. In the preferred embodiment, an individual reaction compartment is pre-pressurizable and is constructed to contain only one slide having a biological specimen thereon.

Without wishing to be held to theory, the pre-pressurization process, when incubating reagents (including any reagents described elsewhere herein) features conditions to minimize evaporative loss of reagents and or aqueous phase (water) or oil phase (oil) of reagents during heating and/or ambient temperature staining conditions. A further aspect of the embodiment featuring the individual pre-pressurized reaction compartment is that during the reaction process, pressure causes the reagents to come in close, intimate contact with the biological specimen by being "pressed" against the biological specimen wherein the physical contact between them is increased due to the pressure exerted on the reagent and thereby upon the biological specimen.

This pressurized force of the reagent toward the biological specimen preferably decreases the time of treatment by the reagents due to very efficient contact of the reagents with the biological specimen. Specimens may have their processing times significantly reduced due to superior staining caused by the reagents being "pressed" against the biological specimen, thus enhancing intimate contact with the biological specimen.

Polymerase Chain Reaction (PCR), including tissue PCR is dependent on the retention of the water levels in the reagents during processing. Specific water concentrations, pH conditions, and temperatures have to be strictly met in order for the PCR reaction to be successful. The pressurized conditions of the reaction compartment of the present invention are ideal for these conditions (low evaporation) to be met during staining. This low evaporation, due to an individual pressurized micro-environment (the individual reaction compartment) is ideal for PCR reactions on glass microscope slides, plastic microscope slides, vessels, tubes, micro arrays, micro titer plates, plates, or any other vessel used for the containment of biological specimens. This pressurization can also be used at ambient temperature as well (e.g., 25° C.).

The preferred embodiment of the pre-pressurized reaction compartment includes not only individual reaction compartments that hold only one biological containing vessel or slide, but also a pre-pressurized chamber that can hold several vessels or slides that can be pre-pressurized to decrease processing time and reduce evaporation or reagent loss.

In a further embodiment, the heating of the reagent on the slide can be done by pre-pressurizing the reaction compartment with heated (below 100° C.) or super heated (above 100° C.) air that would maintain the required temperature for the protocol or would at least pre-heat the reaction compartment prior to the heating element reaching heating temperature or being turned on to heat, and maintain the heating of the reagent on the microscope slide.

In a particularly preferred embodiment of the invention, one or more of the reaction compartments of the apparatus are pre-pressurized after microscope slides are enclosed therein. The pre-pressurization of the reaction compartment may occur before, during, or after the heating element is actuated to heat the microscope slide and reagent thereon.

In another embodiment of the invention, a plurality of slides together in a common chamber may be pre-pressurized and heated thereby eliminating the need to add additional reagent to each slide during the antigen retrieval process. For example, the plurality of slides in the apparatuses shown in U.S. Pat. Nos. 5,654,200; 5,595,707; 6,296,809; 6,352,861; 6,582,962; 6,096,271; 6,180,061; 6,183,693; 6,541,261; or 6,783,733 may be enclosed within a pressurizable chamber and pre-pressurized before, during, or after the heating step begins.

In a preferred embodiment of the invention a plurality of slides are enclosed within a common chamber, reagent is applied to the slides (before or after enclosure within the chamber), the chamber is pressurized to a level above atmospheric pressure, and the slides are heated so the temperature of the reagent on the slide exceeds 85° C. and more preferably exceeds 100° C. Further, the reagent could be applied to the slides after the chamber is pressurized.

The same steps as above could be followed in an alternate embodiment absent inclusion of a heating process. The result of the process without heating is reduced evaporation or vaporization of the reagent from the slide while reagent is reacting with the specimen or sample on the slide and an increase in the physical interaction thereof, due to increased pressure of the reagent with the specimen or sample on the slide.

In the preferred embodiment, each microscope slide is processed within its own individual reaction compartment that can be individually pressurized. Each reaction compartment is separate from every other reaction compartment which together comprise an automated slide staining apparatus to process a plurality of slides simultaneously, if desired, yet individually. Each reaction compartment is functionally independent (i.e., non-interdependent) from each other reaction compartment. The independent operability of each reaction compartment is due to each reaction compartment having separate operational mechanisms, including but not limited to, individually moving slide support elements, individually moving reagent dispensing strips, and individually movable or stationary ports and dispensers for rinses, pressure, vacuum and waste disposal. No single individual processing device in any of the reaction compartments is dependent at anytime on the operation of the processing components of another reaction compartment whether it is in operation or not, including, preferably, microprocessing programs unique to each reaction compartment. All processing components (e.g., including, but not limited to, reagent dispensers, rinses ports, vacuum ports, pressure ports, waste ports, mixing ports, slide supports, reaction compartments, air cooling ducts, and liquid cooling ducts) can be individually and independently moveable and/or usable.

In a further embodiment of the present invention, the microprocessor of the invention utilizes an operating system that can have multiple, individually, and/or simultaneously running processing programs, partially or completely specific to each individual reaction compartment. This would enable a simple approach to programming by eliminating the need for the microprocessor to have one operating program to determine the status of all processing steps as on current slide staining instruments (e.g., as shown in U.S. Pat. Nos. 5,439, 649, 5,595,707, 5,758,033, 5,839,091, 6,296,809, 6,352,861 and 6,783,733). In staining instruments known in the prior art, microprocessors have a processing program which is aware of all the steps for each slide in the staining process and which determines the correct time to activate a common processing device for a particular slide's use (i.e.-reagent dispenser, rinses, air applications, etc.) This "thinking and reacting" approach to the computer's involvement in processing a plurality of slides is inefficient. A lagtime is produced when all the slides are under the control of one program. This inefficient use of time causes increased time for processing just because of the requirement of the microprocessor to determine the next step for each slide and determine any conflicts with two or more slides needing to be processed by a common device at the same time. This type of microprocessing delays the completion of the processing of a slide that would need a processing device at the same time as another slide or multiple slides.

Some staining instruments known in the art feature a "STAT RUN" option. With this type of processing, the user has already started a staining run and has decided that one or more additional slides need to be placed on the instrument and processed because the processing of the "additional slides" is more urgent. The user can put the "original" slides on a lesser priority setting. The "new slides" can then be placed on the instrument and would receive the priority use of the "new slides" of all the processing devices. In between the priority staining protocol, the processing devices can then be used to treat the "original" or "non stat" slides that were on the instrument initially. The requirement for this type of interrupted processing is eliminated due to the features of the present invention.

The advantages of the present invention microprocessor having a single or unique program for each reaction compartment program eliminates the need for a microprocessor which is able to plan the interdependent steps for a plurality of slides being processed, as required by prior art systems. A further advantage of having a separate microprocessing program unique to each reaction compartment, is that if the microprocessors of one or several reaction compartments failed, there would be no effect on the operation of the other reaction compartments. One advantage to this system of microprocessing is that there is no appreciable downtime in the event of a microprocessor failure in one or a few reaction compartments. To the contrary, in the instruments of the prior art, if the microprocessor or operating system fails, then the instrument is completely inoperable and must be repaired.

In the present invention, in a preferred embodiment, there can be a common "master" operating system that could be in communication with each individually unique program so that the user can open a separate program specific to any or all of the reaction compartments at anytime. The separate individual program running a specific reaction compartment would have all the protocols loaded therein for completely processing a slide. The separate program could be updated and edited by the user and with the help of the master program could update all the other separate programs so that each reaction compartment could have the same protocols updates or edits. In the event of a master program failure, the separate unique programs to each reaction compartment would still be operational to process slides; it just would lose the ability of communicate with the separate programs of the other reaction compartments for updating, downloading, or uploading information. In a variation, each reaction compartment may be individually separated and unique to itself in regards to its operating program with no link to the other reaction compartments. A further advantage to having a master operating system is the ability to communicate with the other separate reaction compartment programs for diagnostic purposes, uploading, downloading, and general and specific communications between reaction compartments.

In one embodiment of the present invention, all the motion control requirement necessary for operation of the system can be in the form of AC, DC, solar, and optionally other power sources like pneumatic and steam. The microprocessor can be run on AC, DC, and solar for example. The entire instrument is compact and can be configured with any amount or numbers of reaction compartments necessary. The instrument can be portable to be used in the field (research for example) or carried to an area of use. The number of reaction compartments typically would be 10-20 per chamber and are stackable or are joined linearly or are connected in any other manner which is appropriate. A portable field unit could have as few as 1-5, or 5-10, reaction compartments, for example, for less weight. Preferably the components are made from light weight, anti-corrosive materials. A further advantage of the present invention is that the instrument can be serviced in a modular approach. Each reaction compartment or slide support element in the module can be removed in isolation and serviced or discarded and replaced with an all new unit with simple modular attachments. All the motion controls are preferably modular and either serviceable or completely replaceable. An advantage to this modular serviceability is that the other reaction compartments that are in use or could be used, are not affected during servicing of any device or part from a different reaction compartment.

An advantage of the present invention, as explained previously, is that each slide can be treated with a separate unique reagent, inferring that any slide can have any reagent and be treated at pressures and for varying amounts of treatment times which are the same or different from all other slides loaded into the apparatus. Examples of reagents include, but are not limited to: antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives. Another advantage with the present invention is that cross contamination from reagents or biological specimens one slide by another slide is eliminated because each slide is separated and treated with its own reagent in a separate reaction compartment.

Another important advantage of present invention is that each individual reaction compartment can be cleaned or repaired separately and automatically at the same time that other reaction compartments being used to process slides. Thus, there is no downtime or interruption for the other reaction compartments when a particular individual reaction compartment is being cleaned or repaired. Each reaction compartment can be separately cleaned and/or sterilized by steam, with or without a detergent or sterilizing reagent and dried with heated (below 100° C.) or super heated (above 100° C.) air. This type of sterilized cleaning could be used for example if a biological specimen that was being processed had infectious properties. Each reaction compartment essentially has the properties of an individual self-regulated and controlled miniature autoclave. Sterilization of each reaction compartment prior to use with the next biological specimen process can provide an inherent technical advantage due to the elimination of cross contamination and direct contact with infectious biological specimens. Sterilization can be performed using steam alone, or chemicals dispensed by a reagent strip or another dispensing element.

Reagent Strips

In a preferred embodiment of the invention, reagents are supplied to the reaction compartment from a reagent strip (also referred to herein as a reagent dispensing strip) individualized for a single reaction compartment as described in more detail below (FIGS. 1-22 and 39-78).

The reagent strip comprises at least one and preferably a plurality of separate reagent containers. The reagents in the reagent containers can be of any type known in the art, including but not limited to, antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives. The reagent can also be a dry or desiccated reagent that can be dispensed onto a biological specimen or a dry or desiccated reagent that can be reconstituted prior to dispensing onto the biological specimen. A dry or desiccated reagent can be dispensed onto the biological specimen and then reconstituted by another reagent, for example. The reagent strip and individual reagent containers can be made out of any appropriate material, including, but not limited to, plastics, metals, polymers, and composites. The reagent strip, in a preferred version, has an opening between individual reagent containers which can be sealed by a reagent dispensing plunger on the apparatus to close an upper opening in the reaction compartment (described in more detail below). The reagent strip can be constructed of materials which enable it to be heated, if desired, by a heating means located on or in the reagent strip and/or the individual reagent containers, or heating means adjacent the reagent strip and/or reagent container to pre-heat the reagents prior to dispensing of the reagent from the reagent strip into the reaction compartment and onto the microscope slides or onto the microscope slide before it is inserted into the reaction compartment. The heating means can be any known to those of ordinary skill in the art including, but not limited to, infrared heating, electrical conductive inks, blanket, wire wrappings, light, kapton heaters, foil heater, and conductive type heaters. The reagent strip, for example, can be directly wired to an electrical supply for activating the heaters or can use wireless technology to interface with the heaters located on the reagent strip or reagent containers.

The reagent strips in a preferred embodiment are 0.25 inch (6.35 mm) to 3 inches (76.2 mm) in width and any length to accommodate a sufficient number of reagent dispensing containers to complete a staining protocol. The length in a preferred embodiment is from 4 inches (101.6 mm) to 20 inches (508 mm) or greater, with a length of less than 10 inches (254 mm) being preferred. The reagent strips can have any number, size, configuration, dispensing abilities (i.e., the ability to dispense a reagent from the reagent strip under a pressure greater than that of the reaction compartment's internal pressure) of the reagent containers (i.e., capsules, blister packs, miniature syringe-type containers, dispensing (volume metered) containers, and volume metered dispensing containers that can be dispense their reagents at a pressure higher than the reaction compartment's internal pressures).

The reagent strips can have any number or configuration (arrangement or positioning) of vapor vents, vapor holes, vapor releasing devices (pressure valve or pressure regulator), pressure monitoring devices, or cooling windows based on a particular protocol, for example, as shown in FIGS. 39-78, and as described and discussed below. Each reagent strip can have reagent containers arranged thereon in a pattern such that reagent from the first reagent container is dispensed at one end of the reagent strip and successive reagents are dispensed from successive reagent containers as the reagent strip moves forward toward the last reagent container on the opposite end of the reagent strip without skipping or moving in an opposing direction. The reagent strip can also be utilized by dispensing reagents from non-successive reagent containers in an out-of-order arrangement on the reagent strip wherein the reagent strip is moved "back and forth" to "pick" and "dispense" reagents from particular reagent containers. In a preferred embodiment either method of dispensing (successive or non-successive) would be used to dispense reagents from every reagent container present on the reagent strip without leaving any one reagent unused.

Alternatively, the user can delete or override a pre-set protocol, with the microprocessor, to skip any particular reagent container or containers on the reagent strip. The reagent strip can be placed on the reagent strip support device and is captured and fixedly held in place on the support device by some means known in the art of securing devices. An example of a securing device would be a "clip" such as used on a "clipboard" to secure either end or either side of the reagent strip to the reagent strip holder. Other securing devices which can be used are cogs, snaps, grabbers, low tack adhesives, "fitted" or "snug" fitting strip into the reagent strip holders rails, or other means described herein or known in the art.

Elevated pressure within the reaction compartment can cause reagents placed on the slide without or with heat to be pushed into closer physical contact with the biological specimen on the slide, thereby improving the staining. The pressurizing means (with or without additional heating) can cycle on and off and mixing jets can be employed to mix the reagent and then repressurized to push the reagent down onto the slide. This process can be repeated.

Reagents (e.g., gas and liquid reagents as described elsewhere herein) and all processing components, including, but not limited to, mixing air jets, vacuum (aspiration), pressure relief, air pressure, waste removal, and liquid reagents can be brought to the reaction compartment (in addition to or in lieu of reagents supplied by a reagent strip) of each reaction module (either into or outside of the reaction compartment) via pneumatic of electrically operated valves. These valves can be a separate valve for each component being delivered to each reaction module for example by 2-port, multi-port, rotary type valves (multi-port valve) and or pinch-type valves. The distribution of processing components can be via one or more rotary valves per reaction module. Rotary valves can be used along with 2-port valves or pinch-valves in any combination with or without rotary valves. These miniature type valves (e.g., multi-port valves, rotary valves, 2-port valves, and pinch valves) are commercially available by vendors including Bio-Chem Valve Company, 85 Fulton Street, Boonton, N.J. 07005, Parker Hannifan, 6035 Parkland Boulevard, Cleveland Ohio 44124, and Tri-Tech LLC, 56733 Magnetic Drive, Mishawaka, Ind. 46545.

Embodiments of FIGS. 1-22

Referring now to the drawings, shown in FIGS. 1-8 is a reconfigurable reagent dispensing strip (reagent strip) 10 which is constructed of a base 12, preferably constructed of a metal, plastic, thermoplastic or polymeric material, and a plurality of reagent containers 14 (designated for ease of reference as A-H), each of which is positioned upon a tile 16 of the base 12. The base 12 has an upper surface 18, a lower surface 20, a first end 22 (near first reagent container A) and a second end 24 (near last reagent container H). Each tile 16 preferably has a container platform 26 upon which each reagent container 14 is positioned upon, and is secured thereto via a container connector 30. Each tile 16 has an injector aperture 28 which extends therethrough. Preferably between each container platform 26 is located a rinse port aperture 32 which extends through the base 12. As shown in the figures, a separate rinse port aperture 32 is located between each container platform 26, but each reagent strip 10 may have only a single or several rinse port apertures 32. The reagent strip 10 preferably comprises a plurality of score lines 34 (or perforation lines) individually located between pairs of tiles 16 which enables the user to separate an individual tile 16 from the base 12. Each tile 16 also has a plurality of tile connector receiving holes 36 for enabling detached tiles 16 to be reconnected to an adjacent tile 16. Each reagent container 14 comprises a body 40, an inner space 42 within the body 40, a piston 44, an injector nozzle 46, and a reagent 48 disposed in the inner space 42 between the piston 44 and the injector nozzle 46. In a preferred embodiment, the tiles 16 of the base 12 are molded in a single piece and the reagent containers 14 are molded or permanently attached to their respective tiles 16 in the base 12.

As shown in FIG. 4, an individual tile 16 can be separated along the score line 34 from an adjacent tile 16, wherein, for example, the tiles 16 having reagent containers G and H have been detached. Each tile 16 and reagent container 14 constitutes a single reagent module 50 (e.g., the reagent module 50 having reagent container G is referred to as reagent module 50G and the reagent module 50 having reagent container H is referred to as reagent module 50H. FIG. 5 shows a reagent strip 10a in which reagent module 50H has been reattached to reagent module 50F via a tile connector 52 (FIG. 6) which comprises two pairs of tile connector link feet 54 and has an aperture which leaves the rinse port aperture 32 uncovered. In an alternative embodiment, shown in FIGS. 7 and 8, a reagent strip 10b is constructed of the original reagent strip 10 except reagent module 50G has been replaced with a new reagent module 50gg positioned between reagent module 50F and reagent module 50H and connected thereto via a pair of tile connectors 52.

The configurations of the reagent strips 10a and 10b are merely examples of how the configurations of reagent modules 50 can be rearranged, as will be well understood by a person of ordinary skill in the art.

Shown in FIGS. 9-16 is a reconfigurable reagent dispensing strip (reagent strip) 60 which is constructed of a base 62, preferably constructed of a metal, plastic, thermoplastic or polymeric material, and a plurality of reagent containers 78 (designated for ease of reference as A-H), each of which is positioned upon a container platform 72 of the base 62. The base 62 has an upper surface 64, a lower surface 66, a first end 68 (near first reagent container A) and a second end 70 (near last reagent container H). Each reagent container 78 is secured to the base 62 via a container female connector 74. Each container platform 72 has an injector hole 82 which extends through the base 62. Preferably between each container platform 72 is located a rinse port aperture 76 which extends through the base 62. As shown in the figures, a separate rinse port aperture 76 is located between each container platform 72, but each reagent strip 60 may have only a single or several rinse port apertures 76. Each reagent container 78 comprises an injector 80 and a container male connector 84 which is insertable into a corresponding female connector 74 for securing the container 78 to the container platform 72. The container female connector 74 and container male connector 84 may comprise a twist lock. Each reagent container 78 is otherwise constructed in a manner similar to container 14 of reagent strip 10. In a preferred embodiment, the base 62 is molded in a single piece and the reagent containers 78 are attachable and removable from their respective container platforms 72 in the base 62.

As shown in FIGS. 11 and 13, an individual reagent container 78 can be removed, for example, reagent containers 78 designated as G and H have been detached. FIG. 15 shows a reagent strip 60a in which reagent module 78H has been reattached to the container platform 72 which original held reagent container 78G. In an alternative embodiment, shown in FIG. 16, a reagent strip 60b is constructed of the original reagent strip 60 except reagent container 78G has been replaced with a new reagent container 78GG positioned between reagent module 78F and reagent container 78H and connected thereto upon container platform 72G.

The configurations of the reagent strips 60a and 60b are merely examples of how the configurations of reagent containers 78 can be rearranged, as will be well understood by a person of ordinary skill in the art.

Shown in FIGS. 17-22 is a reconfigurable reagent dispensing strip (reagent strip) 90 which is constructed of a plurality of interlocking reagent modules 92 each comprising a reagent container 94 (designated for ease of reference as A-H), and an interlocking tile 96. The reagent strip 90 has an upper surface 104 and a lower surface 106. Each interlocking tile 96 has an injector aperture 97 which extends therethrough. Preferably between each reagent container 94 is located a rinse port aperture 102. As shown in the figures, a separate rinse port aperture 102 is located between each reagent container 94, but each reagent strip 90 may have only a single or several rinse port apertures 102. Each interlocking tile 96 of the reagent strip has a jigsaw-like male interlocking portion 98 and jigsaw-like female interlocking portion 100, each of which is connectable to an adjacent female interlocking portion 100 and a male interlocking portion 98, respectively. This enables the user to separate and reattach individual interlocking tiles 96. Each reagent container 94 is constructed in a manner similar to that of reagent container 14. In a preferred embodiment, each interlocking tiles 96 is molded in a single piece with the reagent container 94 or is permanently attached in any manner known in the art.

As shown in FIG. 17-19, individual interlocking tiles 96 can be separated from adjacent interlocking tiles 96, wherein, for example, the interlocking tiles 96 having reagent containers G and H have been detached. Each interlocking tile 96 and reagent container 94 constitutes a single interlocking reagent module 92 (e.g., the interlocking reagent module 92 having reagent container G is referred to as reagent module 92G and the reagent module 92 having reagent container H is referred to as reagent module 92H. FIG. 21 shows a reagent strip 90a in which reagent module 92H has been reattached to reagent module 92F via male interlocking portion 98 and female interlocking portion 100 and has a rinse port aperture 102. In an alternative embodiment, shown in FIG. 22, a reagent strip 90b is constructed of the original reagent strip 90 except reagent module 92G has been replaced with a new reagent module 92GG positioned between reagent module 92H and reagent module 92F and connected thereto.

The configurations of the reagent strips 90a and 90b are merely examples of how the configurations of interlocking reagent modules 92 can be rearranged, as will be well understood by a person of ordinary skill in the art.

As described above and elsewhere herein, in a preferred embodiment, the reagent strip of the present invention can be reconfigured from an original or previous configuration, by the user, thereby giving the user the ability to custom arrange the reagent containers 14 on the reagent strip 10, e.g., as shown for reagent strips 10a and 10b.

For example, if a user does not want or need to use all the reagent containers 14 present on a preassembled reagent strip 10, or the user would like to add one or more reagent containers 14 to a particular reagent strip or rearrange them thereon, the user will have the ability to reconfigure the reagent containers 14 on the reagent strip.

As shown in FIGS. 1-4, in one embodiment, the preassembled tiles 16 having reagent containers 14 positioned thereon on the reagent strip 10 can be perforated or easily separated via tile score lines 34 to produce reagent modules 50 thereby enabling the reconfiguration of the reagent modules 50 as described elsewhere herein. The reagent tiles 16 can be any size but preferably those in the same reagent strip 10-10b are all the same size, although certain reagent strips may have tiles 16 that are different in size.

For example, in a reagent strip of the present invention such as reagent strip 10 which is 5 inches long and has 10 individual tiles 16 present, each tile 16 would be 0.5 inch in length. In the embodiment of FIG. 1, the separate tiles 16 are manufactured together in a series and are separable via tile score lines 34 such as grooves, perforations or other means of detaching between the individual tiles 16 as discussed elsewhere herein.

As indicated above, a reagent strip 10 has four tile connector receiving holes 36 in each tile 16. Adjacent tiles 16 can be joined and held by a tile connector 52 similar to a master bicycle chain link. There are many ways known by those of ordinary skill in the art of how to separate and join small parts which could be used to link the tiles 16 together in a way to produce the reconfigured reagent strips of the present invention.

The "snap together" or "puzzle piece" approach if reagent strips 90-90b makes the reagent strip continuous wherein it can be pulled or pushed over the reaction compartment of the apparatus without dislodging one of the reagent tiles and without requiring a separate attaching means to hold the strip together (e.g., a connector).

Any of the reagent strips contemplated herein can include any or all the features noted above, and may also have empty reagent containers 14 which can be filled by the user. In fact, in one embodiment, the reagent strip of the present invention may comprise empty containers 14 for the user to "custom make" his own custom reagent strip using joined empty reagent modules and/or separate tiles to build a reagent strip.

In one embodiment, the reagent strip of the present invention may have a predetermined number of reagent containers in a predetermined sequence that cannot be altered by the user (e.g., see FIGS. 39-78 as described below in more detail). The reagent strip is thus non-reconfigurable. In a preferred embodiment the non-reconfigurable reagent strip is advanced in one direction intermittently as directed by the microprocessor or other means until the all of the reagents in the reagent strip have been deployed. The reagent strip is preferably disposable and is in a preferred embodiment is thrown away and not refilled or reused again. Each reagent container can be deployed consecutively, or one or more containers could be skipped over, then returned to. The reagent strip could be labeled with a computer readable optical character symbol or code (bar code, optically readable symbol, code, character) to identify the type of treatment protocol which would then program the computer as to the type of protocol to be used, and when the next reagent in the series would be dispensed onto the slide.

Once the microprocessor, along with the optical reader on the instrument, has scanned the optical character on the reagent strip, the user would then place the reagent strip on the reagent strip support device and press the start button located near the opening of the individual reaction compartment or on the corresponding icon on the computer screen to start the procedure. The reagent strip support device would preferably have a homing device so the computer would "know" were the first reagent container is located relative to the dispensing plunger. In a preferred embodiment, the distance between reagent containers on the reagent strip would be an equal distance (e.g., 0.5 inches apart) so once the homing position is recognized by the microprocessor, it will know where the first reagent container is on the reagent strip and the reagent strip will be moved to the reagent dispenser position where the reagent will be dispensed onto the biological specimen on the microscope slide. The reagent strip will then be moved 0.5 inches (or other predetermined equal distance) to the next reagent container (or to a rinsing port there between) after the appropriate amount of time. The protocol type, treatment times per reagent, rinse steps, drying, air mixing, etc., are all assessed at the time the optical character is scanned and recognized by the microprocessor.

In this embodiment, it is preferably predetermined that all the reagents on the reagent strip will have to be dispensed onto the slide within a given duration of time and processing conditions. The microprocessor will move and activate all the processing devices independently for all reaction compartments until the last step of the protocol is completed.

The distance between reagent containers on the reagent strip can be any distance that the microprocessor could identify (e.g., from 0.001 inch to about 4.00 inches or greater).

The identification of an individual reagent container by the microprocessor can be by consistent distances after initial homing, each reagent container optionally having its own separate homing device on the reagent strip or on the reagent strip support device, optical recognition, and any other type known in the art for recognizing multiple containers by a microprocessor.

In a further embodiment, the reagent strip or containers or reagent modules thereof could have numeric symbols (numbers) or other symbols (characters) printed thereon that the user simply inputs into the microprocessor for identification of the reagent containers of the reagent strip and protocols associated therewith.

In a preferred embodiment, the reagent strip of the present invention is a single use device which is disposed of after its use, wherein the single use reagent strip is completely or partially prepared by the user (e.g., the user fills one or more containers for the reagent strip) or is completely prepared by a manufacturer. Alternately, the reagent strip could be reusable wherein individual containers could be refilled by a user or manufacturer or new containers or reagent modules could be added to a used reagent strip or could be substituted for used containers or reagent modules on a used reagent strip. Further, a single used container could still have several "doses" or "applications" of reagent wherein it would be advantageous for the user to switch the used container from a used reagent strip to a different reagent strip. Further, as described elsewhere herein, the reagent strip could be reconfigurable such that one or more containers or reagent modules could be replaced, substituted, rearranged or "switched-out" for an alternate one or more containers.

Embodiments of FIGS. 23-38B

Shown in FIGS. 23-38B is a reaction module 110 having a cylindrical reaction compartment 112, a slide support element 114, and a reagent strip support device 116, as previously described. Preferably, the reaction compartment 112 has an inner diameter of 2-5 cm, and more preferably 27 mm, and has a wall thickness of 2 mm to 3 cm. The length of the slide support element 114 is preferably 10-20 cm, and more preferably 12 cm. The length of the reaction compartment 112 is preferably 15-30 cm, and more preferably 20 cm. The reagent strip support device 116 is operatingly connected (e.g., attached at a top) to the reaction compartment 112 via a reagent conduit 122 which opens to the inner space 120 of the reaction compartment 112. There is an injector port orifice 124 in the reagent strip support device 116 which is adapted to receive the injector nozzle from a reagent container of a reagent strip. The reagent strip support device 116 has a front end 126 and a rear end 128. The reagent strip support device 116 functions to receive, support, and eject a reagent strip of the present invention. The slide support element 114 has a base 134 which can reciprocatingly be moved into and out of the reaction compartment 112. The slide support element 114 comprises a heating element 136 upon which a slide 140 is placed. The slide support element 114 may have a handle 142 which enables a technician to more easily insert and withdraw the base 134 from the reaction compartment 112. The slide support element 114 preferably further comprises a sealing means which in the present embodiment is a front O-ring 144 and a rear O-ring 145 for providing a pressure resistant seal of the base 134 against the inner surface 118 of the reaction compartment 112. The slide support element can be constructed from materials which include, but are not limited to, glass, quartz, Pyrex®, borosilicate, steel, metals, aluminum, composites, polymers such as polycarbonate and plastics or combinations thereof.

The slide support element 114 also preferably has a drainage port 146 for receiving and draining reagents and waste liquids from the reaction compartment 112. The slide support element 114 further preferably has one or more cooling ducts 148 which are operatively connected to a sub heating element cooling space 148a beneath the heating element 136, and one or more cooling duct exits 148b which evacuate the cooling air or liquid from the sub heating element cooling space 148a. The slide support element 114 preferably further comprises a first air/pressure duct 150 and a second air/pressure duct 152 for regulation of the pressure within the reaction compartment 112 as discussed elsewhere herein. The duct 150 and/or duct 152 or an additional duct (not shown) can be used for releasing and/or regulating pressure from the reaction compartment 112. The slide support element 114, as noted above, comprises a heating element 136 upon which the microscope slide 140 is placed for application of reagents thereon. The reaction module 110 may further comprise a thermocouple or other temperature measuring device for measuring temperatures of the slide or other components therein. Before operation the slide support element 114 is inserted by a sliding motion into the inner space 120 of the reaction compartment 112 (see FIG. 24A). Also before operation the reagent strip 10 (or any other reagent strip described or enabled herein) is inserted into the reagent strip support device 116, for example, inserting the first end 22 of the reagent strip 10 into the front end of 126 of the reagent strip support device 116, wherein during operation the reagent strip 10 is moved in a direction toward the rear end 128 of the reagent strip support device 116. The reagent strip 10 may be advanced manually or automatically via a pulling or pushing device, including rollers or a track which incrementally advances the reagent strip 10 as instructed by the microprocessor. The reaction module 110 further comprises a reagent conduit 122 in the reaction compartment 112 for allowing passage of a reagent from the reagent strip 10 into the reaction compartment 112. The reaction module 110 also comprises a dispenser plunger 154 (also referred to herein as a dispensing element), which has a dispensing canal 156 therein for allowing passage of another reagent or solution therethrough preferably from a remote source. The reagent strip support device 116 preferably has an injector port orifice 124 for receiving at least a portion of an injector nozzle 46 from a reagent container 14 of the reagent strip 10 during use thereof.

The slide support element 214 may further optionally comprise one or more drainage and/or supply conduits which lead to the base cavity 252 for supplying the base cavity 252 with a liquid or other solution and for draining used liquid from the base cavity 252 after its use (e.g., by aspiration). Other supply ports, conduits, and ducts may supply the reaction compartments of the present invention as described previously in U.S. Pat. Nos. 6,534,008 and 6,855,292.

Figure 28:
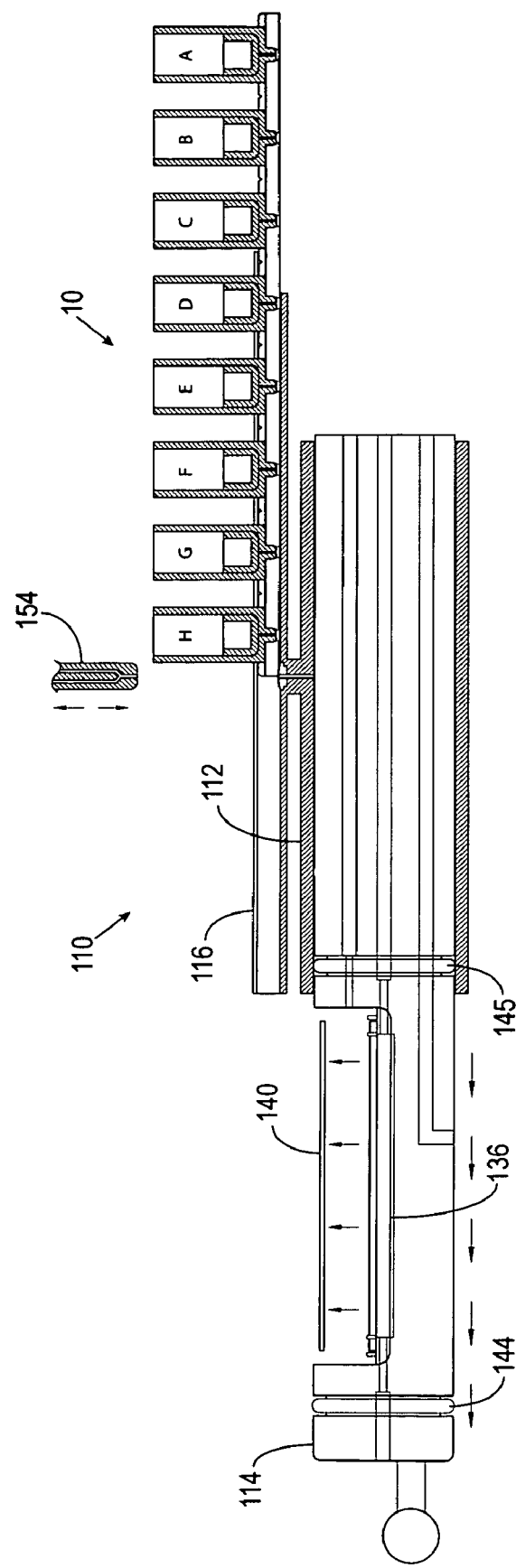
FIG. 28 is a cross-sectional view of the reaction module of FIGS. 23-27B after the reagent strip is completely used and the microscope slide is removed from the slide support element.
Figure 29:
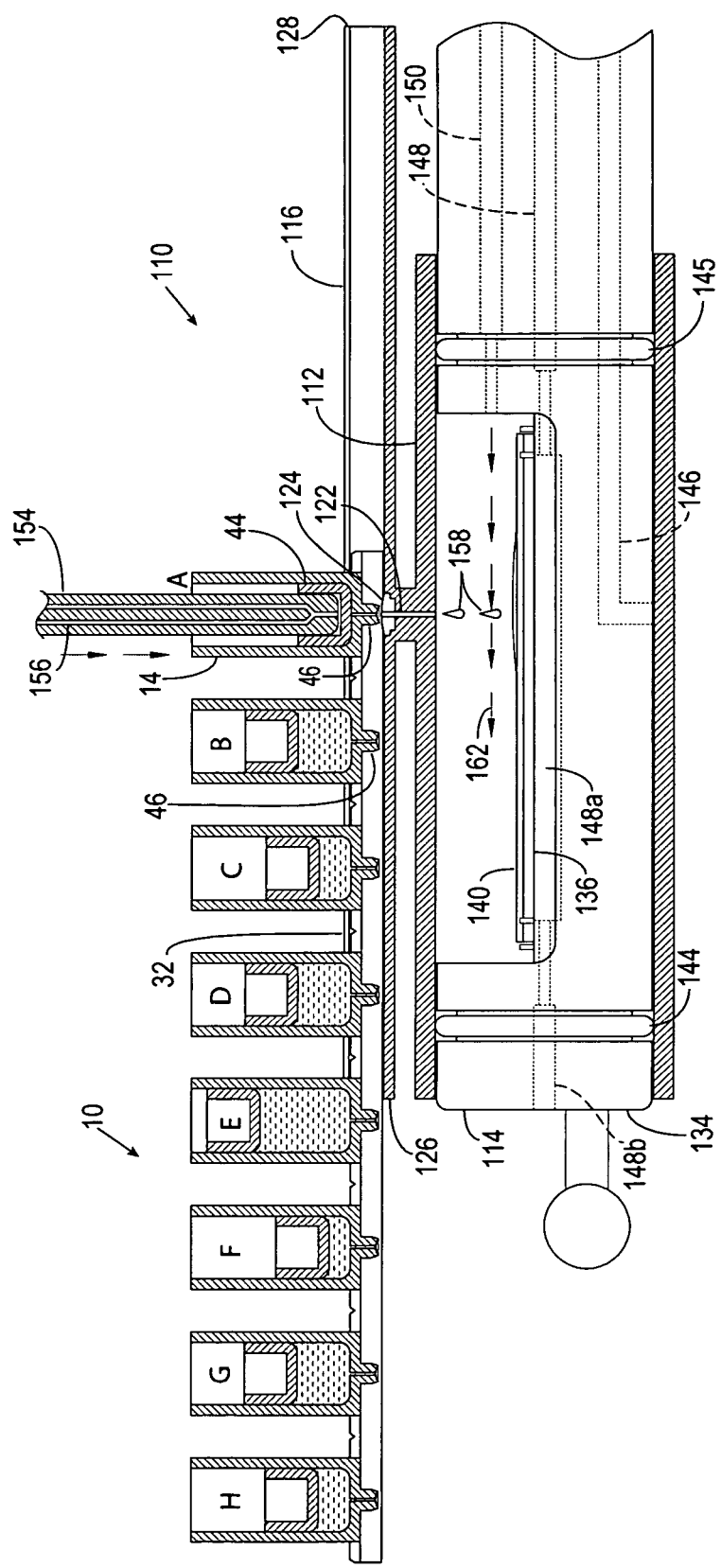
FIG. 29 is an enlarged version of FIG. 24A.
Figure 30:
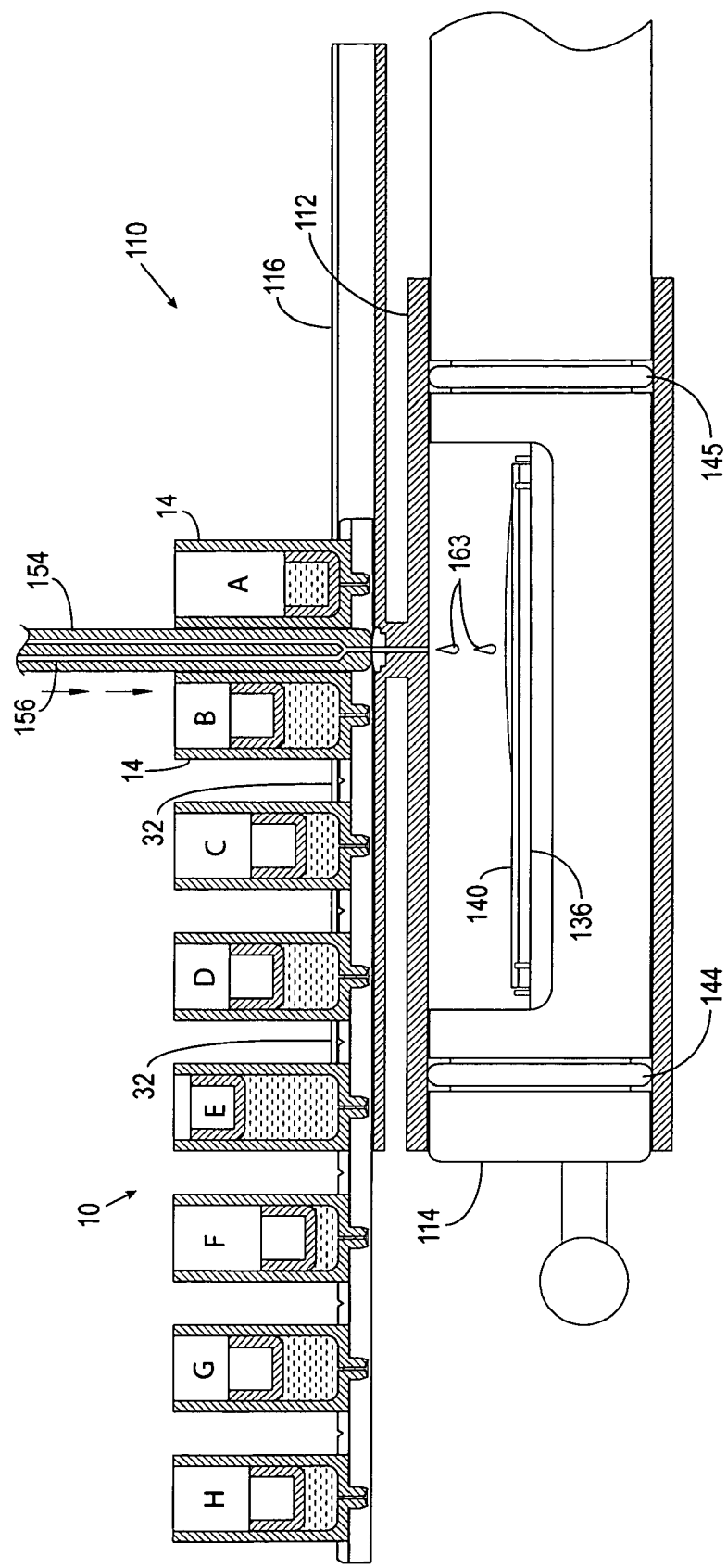
FIG. 30 is an enlarged version of FIG. 26A.
Figure 47:
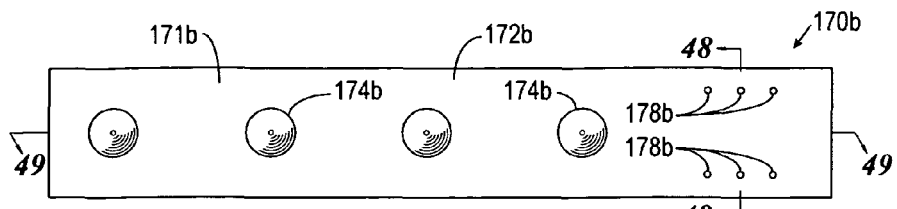
FIG. 47 is a top plan view of an alternate version of the reagent strip of the present invention, the reagent strip having ventilation holes.
Figure 49:
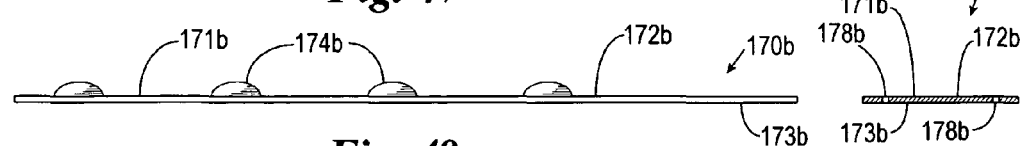
FIG. 49 is a side view of the reagent strip of FIG. 47.
Figure 48:
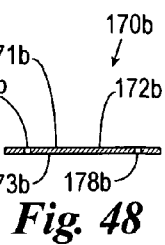
FIG. 48 is a cross-sectional view of the reagent strip of FIG. 47 taken through line 48.
Figure 50:
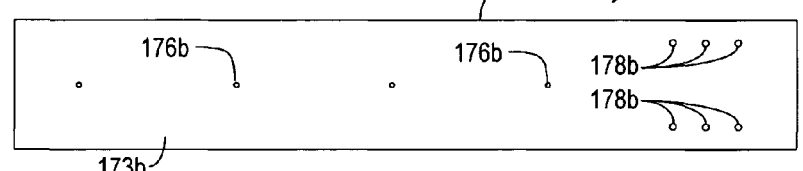
FIG. 50 is a bottom plan view of the reagent strip of FIG. 47.
Figure 51:
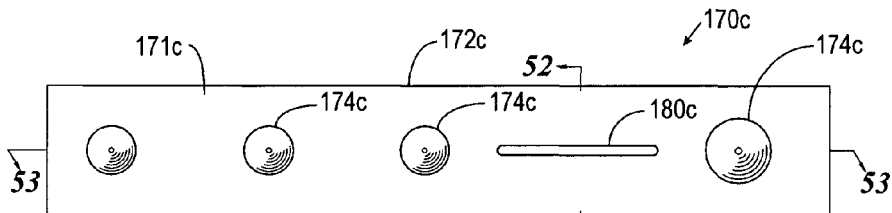
FIG. 51 is a top plan view of an alternate version of the reagent strip of the present invention, the reagent strip having a ventilation slot.
Figure 53:
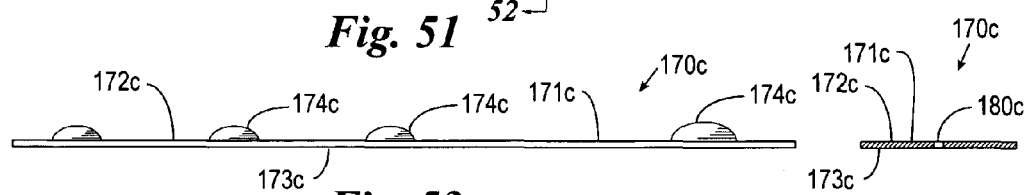
FIG. 53 is a side view of the reagent strip of FIG. 51.
Figure 52:
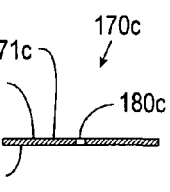
FIG. 52 is a cross-sectional view of the reagent strip of FIG. 51 taken through line 52.
Figure 54:
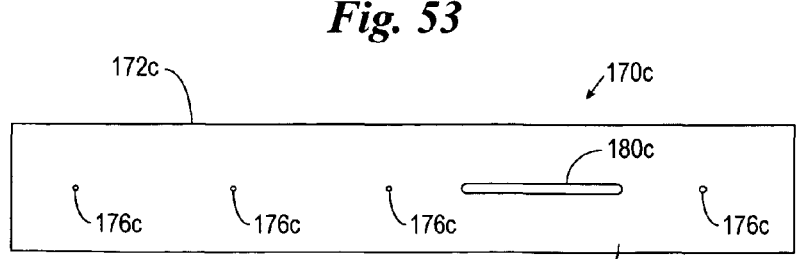
FIG. 54 is a bottom plan view of the reagent strip of FIG. 51.
Figure 63:
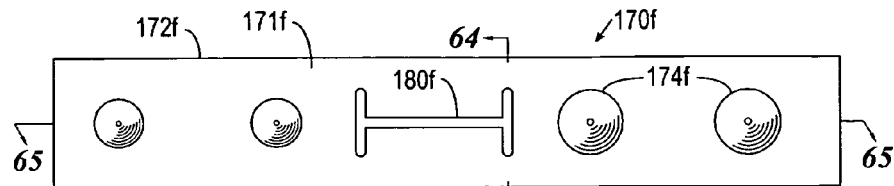
FIG. 63 is a top plan view of an alternate version of the reagent strip of the present invention, the reagent strip having a ventilation slot.
Figure 65:
FIG. 65 is a side view of the reagent strip of FIG. 63.
Figure 64:
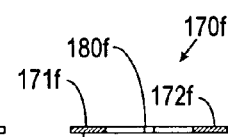
FIG. 64 is a cross-sectional view of the reagent strip of FIG. 63 taken through line 64.
Figure 66:
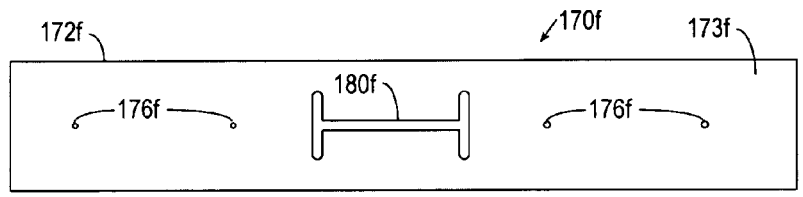
FIG. 66 is a bottom plan view of the reagent strip of FIG. 63.
Figure 67:
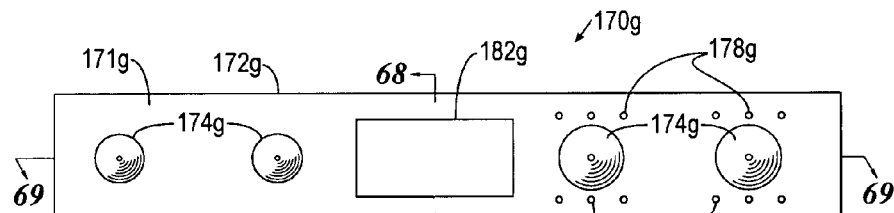
FIG. 67 is a top plan view of an alternate version of the reagent strip of the present invention, the reagent strip having a rapid cooling window.
Figure 69:
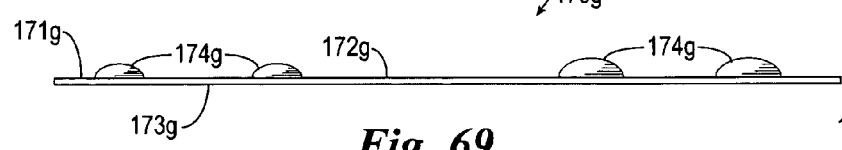
FIG. 69 is a side view of the reagent strip of FIG. 67.
Figure 68:
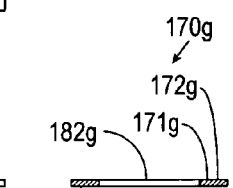
FIG. 68 is a cross-sectional view of the reagent strip of FIG. 67 taken through line 68.
Figure 70:
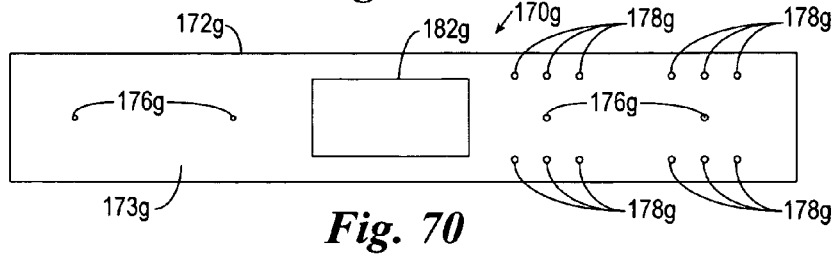
FIG. 70 is a bottom plan view of the reagent strip of FIG. 67.

During operation, as shown in FIGS. 24A-24B and 29, a reagent strip 10 (or any other reagent strip described or enabled elsewhere herein) is inserted into the reagent strip support device 116 as previously described and a reagent container 14 is positioned over the injector port orifice 124. The dispensing plunger 154 is extended downwardly into the inner space 42 of the reagent container 14 wherein it engages the piston 44, forcing the piston 44 downwardly and causing ejection of the reagent 48 through the injector nozzle 46, through the reagent conduit 122 and providing reagent 158 deposited onto the slide 140. When the dispensing plunger 154 forces the piston 44 downwardly, a seal is maintained within the reagent container 14 and in a preferred embodiment enables pressurization of the reaction compartment 112. The reagent 158 can be mixed on the microscope slide 140 by delivering bursts of air 162 through the first air/pressure duct 150 and the second air/pressure duct 152 as discussed in further detail below. In a subsequent step the dispensing plunger 154 may be withdrawn (FIG. 25A-B) and the base 134 of the slide support element 114 tilted within the reaction compartment 112 to allow the reagent to drain from the slide 140, forming a reagent drainage 160 which is collected in the drainage port 146, removed from the reaction compartment 112, and collected in a waste storage container (not shown). In a later step (FIGS. 26A-B) the slide 140 is returned to an upright, horizontal position and the reagent strip 10 is advanced until the rinse port aperture 32 is positioned above the injector port orifice 124 wherein rinse solution 163 is delivered from a rinse solution reservoir (not shown). Furthermore, air or liquid may be delivered through the dispensing canal 156 in the dispensing plunger 154 to cause mixing of reagent 158 or to remove the reagent 158 from the slide, or to enhance the rinsing of the reagent 158 or rinse solution 163 from the slide 140 (e.g., see FIGS. 27A-B). Finally as shown in FIG. 28, after all reagents from the reagent strip 10 have been dispensed, the portion of the slide support element 114 which carries the slide 140 is withdrawn from the reaction compartment 112 wherein the slide 140 is then removed from the slide support element 114. Note that FIGS. 29-30 are enlarged versions of FIGS. 24A and 26A, respectively and are provided herein for the purpose of more easily showing the steps therein.

FIGS. 31A-32B provide a more detailed description of how the bursts of air 162 delivered form the first air/pressure duct 150 and second air/pressure duct 152 can be used to cause mixing of the reagent 158 on the slide 140. Preferably, the first air/pressure duct 150 and second air/pressure duct 152 are operated alternately to provide bursts of air 162 in alternating clockwise/counterclockwise directions to agitate the reagent 158. The first air/pressure duct 150 and second air/pressure duct 152 can be used simultaneously to pressurize the reaction compartment 112. At any desired time the heating element 164 can be used to heat the slide 140 and reagent 158 thereon as discussed in greater detail elsewhere herein. As shown in FIGS. 33-35B after the slide 140 is heated, it can be rapidly cooled by directing air or liquid via the cooling ducts 148 into sub heating element cooling spaces 148a which are located below the heating element 164 which in one embodiment is located below and is used to heat a hot plate 166 upon which the slide 140 is positioned. Air or liquid used for cooling can then pass through cooling duct exits 148b. In another embodiment, shown in FIGS. 36-38B a sub heating element cooling space 148c is similar to sub heating element cooling space 148a except the cooling air or liquid which passes through the sub heating element cooling space 148c is delivered via one of the cooling ducts 148 and exits the slide support element 114 via the outer cooling duct 148.

Other embodiments of reagent strips of FIGS. 23-38B which have features similar to those of FIGS. 39-78, having various combinations of vent holes, ventilation slots, and rapid cooling windows can readily be envisioned particularly regarding the sizes, shapes and locations of the vent holes, ventilation slots and rapid cooling windows.

Each individual reagent containers of the present invention, e.g., reagent containers 14, 78 and 94, can be a container whose inner space has been evacuated to hold a vacuum. To fill the reagent container, a reagent source can be contacted with a filling port of the reagent container (not shown) wherein the vacuum then pulls the reagent into the inner space of the reagent container. The reagent container volume limits the amount of reagent pulled into the reagent container from the reagent source.

Alternatively, the reagent container may have a plunger or piston present in a down (dispense) position. The dispensing port (e.g., the injector nozzle) of the reagent container is connected to a reagent source. Reagent is drawn into the reagent container by moving the plunger or piston in the reagent container upwardly. Once the plunger or piston has reached its uppermost position, the individual reagent container is filled. The filling of a reagent container could be as simple as a method of filling a common syringe with a reagent and affixing the outlet of the syringe to the bottom of the individual reagent container and pushing the reagent into the reagent container thus moving the reagent container's plunger or piston upwardly and filling the reagent container. The bottom of the injector nozzle of each reagent container would then be sealed or capped with its own individual cap or seal. The plurality of caps or seals on a reagent strip may be removable together. This linkage is useful in one embodiment to remove the caps in one motion to expose the injector nozzles prior to putting the reagent strip on the reagent strip support device. In an alternate embodiment of the sealing of the injector nozzles (i.e., the dispensing side of the reagent strip) a cover made of foil, plastic, or other covering means can be used that can be peeled away prior to use to expose the injector nozzles.

In a preferred embodiment, the injector nozzles, reagent strips, and the dispensing plunger or piston or other ducts leading to the reaction module can dispense reagents by using a pressure which is greater than the internal pressure of the reaction compartment into which the reagent is dispensed. For example, if a reaction compartment is pressurized at 30 psig (308.1 kPa), a reagent must be dispensed into the reaction compartment with force exceeding 30 psig (308.1 kPa) to overcome the pressure in the reaction compartment. Otherwise, the reaction compartment would have to be depressurized to add the reagent. Such a depressurization step would probably be deleterious because the depressurization would cause the reagent on the slide to boil off due to extreme evaporation at high temperature. The present invention can dispense its reagents under pressure in the range of over 0 to 350 psig (101.3 kPa-2514 kPa), preferably in the range of 0.5-100 psig (104.8 kPa-790.6 kPa) and more preferably 5-50 psig (135.8 kPa-446.0 kPa) and the reaction compartment can be pressurized to these levels as well.

The reagent strips of the present invention are used to provide reagents onto microscope slides positioned in, or prior to being positioned in, a pressurizable reaction compartment of the antigen retrievable apparatus of the present invention as shown for example in FIGS. 23-38B.

As shown in FIGS. 23-38B, each reaction compartment of the apparatus preferably comprises a hollow cylinder, preferably constructed of a thermoplastic resin or polymer (including but not limited to polycarbonate or any other polymeric material able to withstand elevated temperatures and pressures), glass, Pyrex®, quartz, other crystalline materials, and metals and metal alloys. The tubular nature of the reaction compartment is preferred because the elevated pressures created within the reaction compartment during its use are more evenly distributed therein.

The seal between the slide support element and the reaction compartment can be formed using O-rings, as shown in the FIGS. 23-38B or can be formed using an inflatable O-ring, a seal, or an inflatable seal depending on the shape of the mating surfaces. The seal can be constructed of plastic, polymer, thermoplastic, resin, ceramic, rubber, metal glass, or composite, for example. In a preferred embodiment, the mating surfaces of the slide support element and the reaction compartment are of a low tolerance ground or polished sealing surface. These sealing surfaces when joined together eliminate the need for a visually or seal raised above the mating surface. In this embodiment, the ground or polished mating surface alone, when joined together, produces a microscopic seal with a large surface area to seal the reaction compartment and maintain an elevated pressure therein (above atmospheric) even under high temperature conditions above 100 degrees centigrade. The material of the slide support element and the tubular reaction compartment can feature a very high tolerance ground or polished seal on the mating surfaces. In the preferred embodiment, the slide support element and the reaction compartment is made of a high tempered glass material like Pyrex®, or any material that can produce a ground or polished mating surface to form a seal which maintains a pressure above atmosphere pressure. The ground glass surface, or polished surface of the slide support element against the ground or polished surface of the reaction compartment yields an air-tight and pressure-tight seal when the two ground or polished surfaces are joined together, wherein, there is no separate replaceable or raised seal to fill the mating surfaces void. This embodiment of the present invention eliminates the need for raised seals (e.g., O-rings) thus reducing maintenance cost for the replacement of separate components seal such as O-rings and increases simplicity and efficiency and seals the reaction compartment even under pressures above atmospheric levels (e.g., above 14.7 psig (101.325 kPa), i.e., above 0 psig (101.325 kPa)) and high temperature conditions above 100° C. degrees centigrade.

The apparatus of the present invention preferably comprises a plurality of reaction modules, such as the reaction module 110 shown in FIG. 23. Each reaction module 110 comprises a tubular reaction compartment 112, a slide support element 114 and a reagent strip support device 116. The reaction compartment has an inner surface 118 and an inner space 120 into which the slide support element 114 can be more for treating a biological sample on a microscope slide 140 thereon. The slide support element 114 is able to slide into and out of the reaction compartment 112 in a manner similar to a piston within a cylinder. When the slide support element 114 is withdrawn from the reaction compartment 112, a slide 140 can be placed thereon or removed therefrom. The slide support element 114 can be inserted into the reaction compartment 112 for treatment of the material on the slide 140 as described elsewhere herein. As shown below, the slide support element 114 can be turned (tipped) within the reaction compartment 112 for facilitating the removal of reagents or fluids from the slide 140 after the slide 140 has been treated, as shown in the figures (e.g., see FIG. 25B). Reagents or fluids on the slide 140 can be mixed by air circulation as shown in FIGS. 31A-32B for example. After heating, the slide 140 can be cooled by circulation of air or fluid thereunder, for example as shown in FIGS. 34A-38B. In another embodiment, the slide 140 could be cooled by using a circulating liquid such as a reagent that becomes pre-heated by passing under the heated slide 140 thus transferring heat to the circulating reagent which could then be dispensed onto the slide 140.

The reaction compartment 112 can be constructed of any material known in art of high temperature and pressure compatible devices. These materials also include, but are not limited to, plastic, composites, ceramics, metals and coated metals. The instrument can be coated for resistance to porosity, to increase hydrophobic and hydrophilic properties, for ease of cleaning, chemical resistance, and stain resistance. These coatings could be, for example, Teflon®, fluoropolymers, any other known coating that would impart these desirable properties to all surfaces of reaction compartment 112 and surrounding structures with a different coating being present on different portions of the apparatus. In one embodiment, for example, the inner surface 118 of the reaction compartment 112 is coated with a hydrophobic, chemical, and stain resistant coating to aid in the draining of the condensed reagents on the inner surface 118 of the reaction compartment 112 and ease of removal of reagents therefrom.

The slide support element 114 of the reaction module 110 preferably comprises a heating element 136, and a hot plate (which may be one and the same) and which may include guide clips 138 or pegs or elements to locate and secure the slide 140 thereon. The tops of the clips 138 may be positioned to be below an upper surface of the microscope slide 140, so as to prevent reagent on the slide 140 from being wicked off by the clips 138 by capillary action.

In a particularly preferred embodiment, underneath the heating element 136 is one or more recessions (sub-heating element cooling spaces 148a) which are connected via cooling ducts 148 to a gas or liquid supply source to quickly cool the heating element 136 thereby quickly cooling the microscope slide 140 and the reagent thereon.

The slide support element 114 and reaction compartment 112 can be constructed of any material suitable for use under pressurized conditions and resistant to corrosion by laboratory reagents, including but not limited to stainless steel, metals, plastics (clear or opaque), polymers (e.g., polycarbonate), tempered glass, and Pyrex®.

Containment of waste and used reagents from the reaction module 110 will be now briefly discussed, and will be discussed in more detail below.

In a preferred embodiment the apparatus of the present invention has a waste container (not shown) which can be connected to all the reaction modules 110 by a fitting that can join multiple tubes or conduits. In a preferred embodiment of the present invention, this main fitting (not shown) can be joined to the waste container (which preferably is disposable or non-reusable) by a breakable joint present on the waste container. This fitting on the waste container snaps together with the main fitting of the instrument. This attachment is secure and will not leak under pressure. When detached, this fitting on the waste container partially "breaks away" and leaves behind on the waste container an airtight, leakproof, tamper proof, non-removable seal. The residual piece that was detached from the waste container is removed by the technician and then is ready to be reattached to a new waste container. The waste container is now ready to be deposited in its entirety by medical waste personnel. No other sealing is necessary. The tamper proof seal of the separated fitting protects the medical waste personnel from coming in contact with any of the waste in the sealed waste container.

In an alternate embodiment the detachable fitting on the waste container may not have any residual piece on the main instrument fitting but rather "breaks" or "snaps" away form the detachable piece on the disposable waste container cleanly.

In an alternate embodiment the instrument could have two or more waste containers wherein it is possible to remove one full waste container while retaining one or more other waste containers attached to receive waste from the working reaction modules. The microprocessor could alert the technician that a waste container is in need of replacing by a sensor located in the waste container. If the technician chooses to ignore the alert from the instrument, it could divert the waste to another waste container until the time is convenient to replace the full waste container. Since the processing device operates each reaction module 110 independently, the waste containers are set-up to receive waste from any of the working reaction modules 110 eliminating the need to stop the instrument to change any full waste container. The waste containers can be hooked up in a series or in parallel to keep at least one waste container active while any other waste container is being changed. The microprocessor is in direct communication with all the waste containers and will shut down waste routes that are going to a fitting that has been detached and is in the process of replacement.

In an alternate embodiment, the instrument could have one main waste container which when full would alert the technician to start the waste recovery procedure. The main waste container could be drained to a secondary waste container to be disposed.

The waste container can be charged with activated charcoal or other neutralizing chemicals to aid in decontamination. The waste container can have a vent that has a neutralizing filter to release the build up of pressured vapors.

Turning again to the figures, it will be shown in greater detail how the reaction module 110 (and others described herein) operates.

As explained above, the operation sequence of the reagent strip 10 with the reaction module 110 is generally shown in FIGS. 23-38B.

The slide 140 is loaded onto the heating element 136 or the hot plate 166 of the slide support element 114 and positioned by location clips 138 or guide pegs or other orientation elements to verify proper location of the microscope slide 140 on the slide support element 114. The slide support element 114 and slide 140 is then moved into the reaction compartment 112 wherein it is sealed via the O-rings 144 and 145. The reagent strip 10 is placed onto the reagent dispensing strip support device 116. The protocol is entered either automatically or manually (described elsewhere herein) and the instrument with the plurality of reaction modules 110 is instructed to start. Depending on the protocol the heating element 136 can start to heat the slide 140 or the protocol instructs the dispensing of a reagent from the reagent strip 10 or from another source via the dispensing plunger 154.

If an individual reagent container 14 located on the reagent strip 10 is selected, that particular reagent container 14 will be positioned over the injector port orifice 124, and the dispensing plunger 154 and depresses the piston 44 within the reagent container 14 to expel the reagent 48 therefrom onto the microscope slide 140. The reagent strip 10 would then be moved to position the rinse port aperture 76 in the reagent strip 10 (e.g., generally located between adjacent reagent containers 14) over the injector port orifice 124 wherein the dispensing plunger 154 would be lowered to seal the injector port orifice 124 or, additional air or reagent could be injected into the reaction compartment 112. Once the reagent 158 which has been applied to the slide 140 is removed from the slide 140 by tilting the slide 140 or by rinsing, the slide 140 can be further rinsed with a reagents or treated with pressurized air from the dispensing plunger 154.

As disclosed in U.S. Pat. Nos. 6,534,008 and 6,855,292, the apparatus of the present invention used to treat the microscope slide comprises a plurality of reaction modules 110 each having a reaction compartment 112 which is encloseable for reducing evaporative heat loss by vapors being contained inside the reaction compartment 112 during heating conditions.

As discussed elsewhere herein, the reaction compartments of the reaction modules of the present invention can be pressurized (positively or negatively) during heating of the reaction compartment or pressurized without heating, or pre-pressurized (positively or negatively) before the microscope slide or other component of the reaction module is heated.

The reaction compartment can be pre-pressurized, then heated, then repressurized to maintain a preferred pressure level within the reaction compartment. The reaction compartment can be pressurized either by vapor, gas, or steam produced by a reagent, solution, or liquid within the reaction compartment or by air, steam, inert gases, $N_2$ or any other gas typically used for pressurizing vessels, which is provided from an external source and is supplied via air/pressure ducts or conduits or vacuum lines into the reaction compartment.

Embodiments of FIGS. 39-78

Various embodiments of reagent strips which can be used with the present invention, and which may also be used in the apparatus of U.S. Pat. Nos. 6,534,008 and 6,855,292, are shown in FIGS. 39-78. These reagent strips have various holes, openings, slits and windows for controlling the venting of vapors produced within the reaction compartments 112, as described below.

Alternate embodiments of reagent strips which may be used in the present invention are shown in FIGS. 39-78 herein and are similar to embodiments of reagent strips used and described in U.S. Pat. Nos. 6,534,008 and 6,855,292, and U.S. Ser. Nos. 10/245,035 and 10/943,386.

Shown in FIGS. 39-42 is a reagent strip 170 which can be used in an alternate embodiment of the presently described apparatus which has a dispensing plunger which can crush a capsule containing a reagent. Reagent strip 170 has a base 172, an upper surface 171, a lower surface 173, a plurality of reagent capsules 174, each having a reagent dispensing port 176 thereunder, and a plurality of vent holes 178 positioned between a pair of the reagent capsules 174. The vent holes 178 allow excess vapor to escape from the reaction compartment thereby preventing excessive pressure buildup within the reaction compartment.

Shown in FIGS. 43-46 is another reagent strip 170a which can be used in an alternate embodiment of the presently described apparatus which has a dispensing plunger which can crush a capsule containing a reagent. Reagent strip 170a has a base 172a, an upper surface 171a, a lower surface 173a, a plurality of reagent capsules 174a, each having a reagent dispensing port 176a thereunder, and a plurality of vent holes 178a positioned between adjacent one of the reagent capsules 174a. The vent holes 178a allow excess vapor to escape from the reaction compartment thereby preventing excessive pressure buildup within the reaction compartment.

Shown in FIGS. 47-50 is another reagent strip 170b which can be used in an alternate embodiment of the presently described apparatus which has a dispensing plunger which can crush a capsule containing a reagent. Reagent strip 170b has a base 172b, an upper surface 171b, a lower surface 173b, a plurality of reagent capsules 174b, each having a reagent dispensing port 176b thereunder, and a plurality of vent holes 178b positioned between near an end of the reagent strip 170b. The vent holes 178b allow excess vapor to escape from the reaction compartment thereby preventing excessive pressure buildup within the reaction compartment.

Shown in FIGS. 51-54 is another reagent strip 170c which can be used in an alternate embodiment of the presently described apparatus which has a dispensing plunger which can crush a capsule containing a reagent. Reagent strip 170c has a base 172c, an upper surface 171c, a lower surface 173c, a plurality of reagent capsules 174c, each having a reagent dispensing port 176c thereunder, and a ventilation slot 180c positioned between a pair of the reagent capsules 174c. The ventilation slot 180c allows excess vapor to escape from the reaction compartment thereby preventing excessive pressure buildup within the reaction compartment.

Shown in FIGS. 55-58 is another reagent strip 170*d* which can be used in an alternate embodiment of the presently described apparatus which has a dispensing plunger which can crush a capsule containing a reagent. Reagent strip 170*d* has a base 172*d*, an upper surface 171*d*, a lower surface 173*d*, a plurality of reagent capsules 174*d*, each having a reagent dispensing port 176*d* thereunder, a ventilation slot 180*d* and a rapid cooling window 182*d* positioned between a pair of the reagent capsules 174*d*. The ventilation slot 180*d* allows excess vapor to escape from the reaction compartment thereby preventing excessive pressure buildup within the reaction compartment, and the rapid cooling window 182*d* increasing the speed at which the microscope slide, and reaction compartment cool down after a heating step.

Shown in FIGS. 59-62 is another reagent strip 170*e* which can be used in an alternate embodiment of the presently described apparatus which has a dispensing plunger which can crush a capsule containing a reagent. Reagent strip 170*e* has a base 172*e*, an upper surface 171*e*, a lower surface 173*e*, a plurality of reagent capsules 174*e*, each having a reagent dispensing port 176*e* thereunder, and a ventilation slot 180*e* and a rapid cooling window 182*e*. The ventilation slot 180*e* allows excess vapor to escape from the reaction compartment thereby preventing excessive pressure buildup within the reaction compartment, and the rapid cooling window 182*e* increases the rate at which the microscope slide and reaction compartment cool down after a heating step.

Shown in FIGS. 63-66 is another reagent strip 170*f* which can be used in an alternate embodiment of the presently described apparatus which has a dispensing plunger which can crush a capsule containing a reagent. Reagent strip 170*f* has a base 172*f*, an upper surface 171*f*, a lower surface 173*f*, a plurality of reagent capsules 174*f*, each having a reagent dispensing port 176*f* thereunder, and a ventilation slot 180*f* positioned in the center of the base 172*f* between adjacent one of the reagent capsules 174*f*. The ventilation slot 180*f* allows excess vapor to escape from the reaction compartment thereby preventing excessive pressure buildup within the reaction compartment.

Shown in FIGS. 67-70 is another reagent strip 170*g* which can be used in an alternate embodiment of the presently described apparatus which has a dispensing plunger which can crush a capsule containing a reagent. Reagent strip 170*g* has a base 172*g*, an upper surface 171*g*, a lower surface 173*g*, a plurality of reagent capsules 174*g*, each having a reagent dispensing port 176*g* thereunder, and a plurality of vent holes 178*g* positioned adjacent a pair of the reagent capsules 174*g*. The vent holes 178*g* allow excess vapor to escape from the reaction compartment thereby preventing excessive pressure buildup within the reaction compartment. The reagent strip 170*g* further comprises a rapid cooling window 182*g* to accelerate cooling of the microscope slide and the reaction compartment.

Shown in FIGS. 71-74 is another reagent strip 170*h* which can be used in an alternate embodiment of the presently described apparatus which has a dispensing plunger which can crush a capsule containing a reagent. Reagent strip 170*h* has a base 172*h*, an upper surface 171*h*, a lower surface 173*h*, a plurality of reagent capsules 174*h*, each having a reagent dispensing port 176*h* thereunder, a ventilation slot 180*h*, and a rapid cooling window 182*h*. The ventilation slot 180*h* allows excess vapor to escape from the reaction compartment thereby preventing excessive pressure buildup within the reaction compartment and the rapid cooling window 182*h* increases the rate at which the microscope slide and reaction compartment cool down after a heating step.

Shown in FIGS. 75-78 is another reagent strip 170*i* which can be used in an alternate embodiment of the presently described apparatus which has a dispensing plunger which can crush a capsule containing a reagent. Reagent strip 170*i* has a base 172*i*, an upper surface 171*i*, a lower surface 173*i*, a plurality of reagent capsules 174*i*, each having a reagent dispensing port 176*i* thereunder, a plurality of vent holes 178*i*, and a rapid cooling window 182*i*. The vent holes 178*i* allow excess vapor to escape from the reaction compartment thereby preventing excessive pressure buildup within the reaction compartment, and the rapid cooling window 182*i* increases the rate at which the microscope slide and reaction compartment cool down after a heating step.

The vent structures of the reagent strips of FIGS. 39-78 are designed to allow sufficient heat to be contained within the reaction compartment 112 by controlling the amount of vapor loss from the reagent to produce and maintain boiling conditions of reagents. It is known that aqueous reagents will boil at different temperatures in relation to the amount of solute contained in the solution. It is also known that when boiling small amounts of aqueous liquids (e.g., 500 microliters to 100 ml) the solution will reach a particular boiling point at which its liquid phase will go to its gaseous phase. This progression should to be controlled to reduce the amount of evaporative heat loss from the reaction compartment.

An example of why the ability to control the release of evaporative vapors is important to maintaining boiling conditions is demonstrated by placing an open-top chamber about a slide. During heating to boiling conditions small gaseous bubbles will form at the surface of the slide where the reagent is hottest. These bubbles, when they reach a size that can no longer cling to the surface of the microscope slide, will detach and rise to the cooler upper layers of the heated reagent. The bubbles will then burst at the surface of the reagent to release the gaseous phase to the atmosphere. This energy release cools the upper layer of the reagent. This property allows only the lower layer to reach the boiling point, and the remainder of the reagent only reaches temperatures below the boiling point of the reagent due to the evaporative heat loss, and subsequent reduction of the net temperature of the reagent. The reagent slowly loses its volume to evaporation and never reaches a constant vigorous boiling condition necessary for most antigen retrieval protocols.

In contrast, as occurs during the process of the present invention, the reaction compartment is sealed or substantially sealed, such that the reagent would quickly come to equilibrium in a boiling state throughout the layers of reagent and would maintain a vigorous constant boiling condition and would build up pressure inside the closed reaction compartment. If not regulated, the pressure could exceed safe levels and the reaction compartment could eventually fail under pressure. To have the benefits of a constant vigorous boiling effect of the reagent on the slide, the evaporative heat loss must be regulated by enclosing the reaction compartment sufficiently so as to release the gaseous phase at a rate that maintains a vigorous boiling condition.

The reagent strips shown in FIGS. 39-78 comprise a plurality of capsules sized to contain various amounts of reagents, fluids, or buffers, for example, from 10 µl to 2-5 ml. The capsules can contain reagents such a stains, probes, rinses, antibodies, buffers, chemicals or solvents, and the reagent strip preferably has at least one vent, slot, or window. Each vent may be preferably from 10 µm to 20 mm in diameter and extends between an upper surface and a lower surface of the reagent strip. There are typically from one to twenty vents in each reagent strip but there may be more in other embodiments. A reagent strip may be constructed with only a single capsule for dispensing an antigen recovery buffer or other reagent.

The number and diameters of vents and slots in the reagent strips can be varied depending on the types of reagents and antigen recovery buffers used and the amount of pressure, steam, vapor or gases which are likely to be released during the process of heating the antigen recover buffer applied to the microscope slide.

When the vent is a slot or a slit or window, rather than a "hole", the vent may be from 10 µm to 10 mm wide, for example. There may be typically from one to twenty vents in a reagent strip but may be more in other embodiments. The vents or slots are preferably located in a position of the reagent strip which is between adjacent capsules or to the sides of capsules. Preferably any one of the reagent dispensing strips of the present invention contemplated herein comprises only 1 to 25 reagent containers, only 1-20 reagent containers, only 1-15 reagent containers or only 1-10 reagent containers.

Embodiments of FIGS. 79-85

Figure 79:
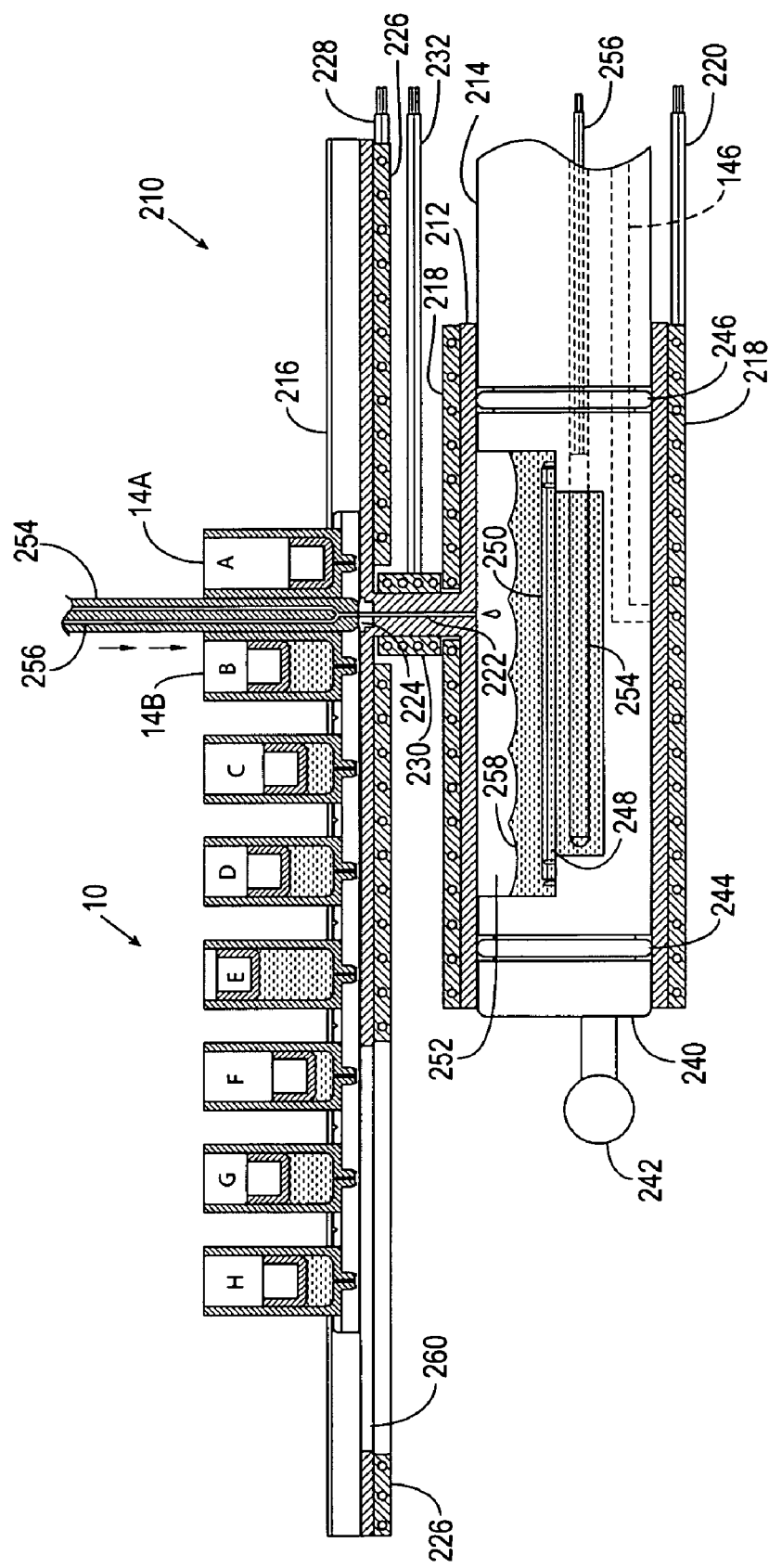
FIG. 79 is a cross-sectional side view of an alternate embodiment of a reaction module of the present invention.
Figure 80:
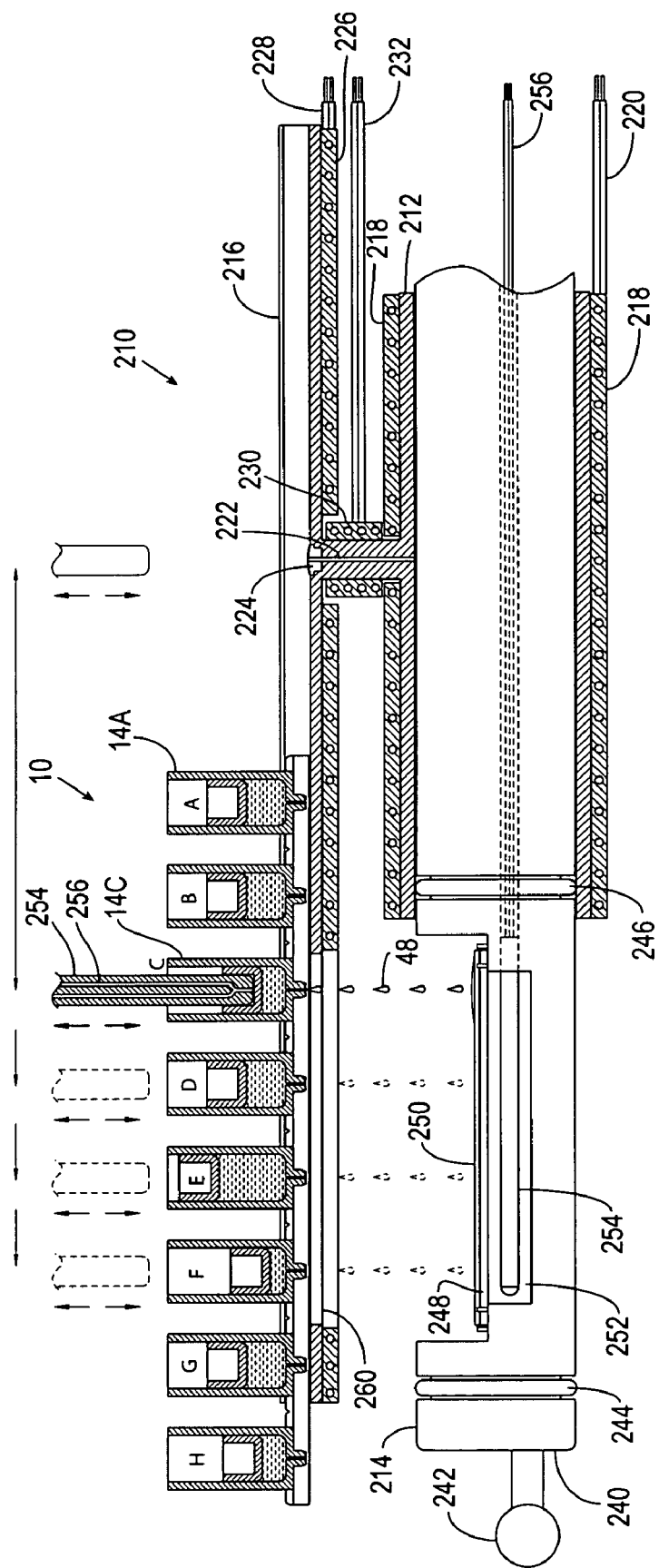
FIG. 80 is a cross-sectional side view of the reaction module of FIG. 79 in an alternate processing configuration.
Figure 81:
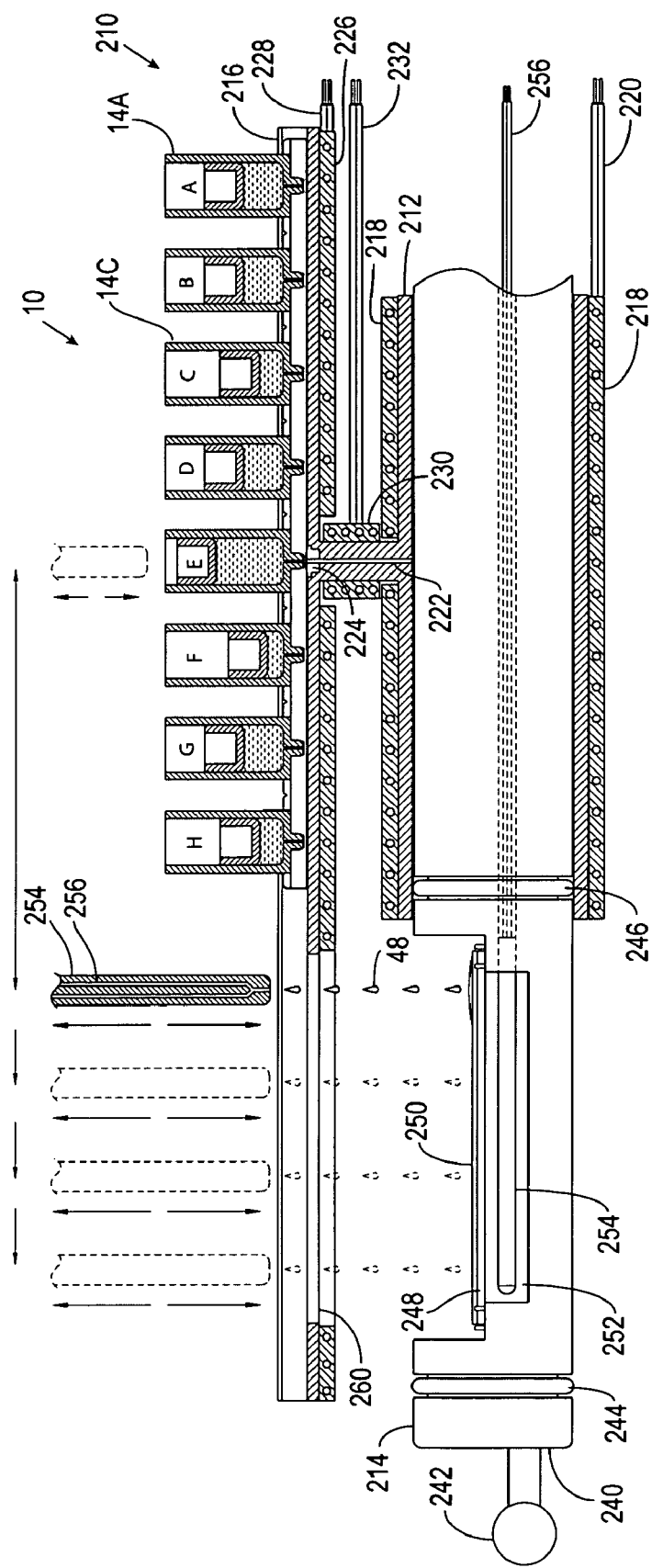
FIG. 81 is a cross-sectional side view of the reaction module of FIG. 79 in an alternate processing configuration.
Figure 82:
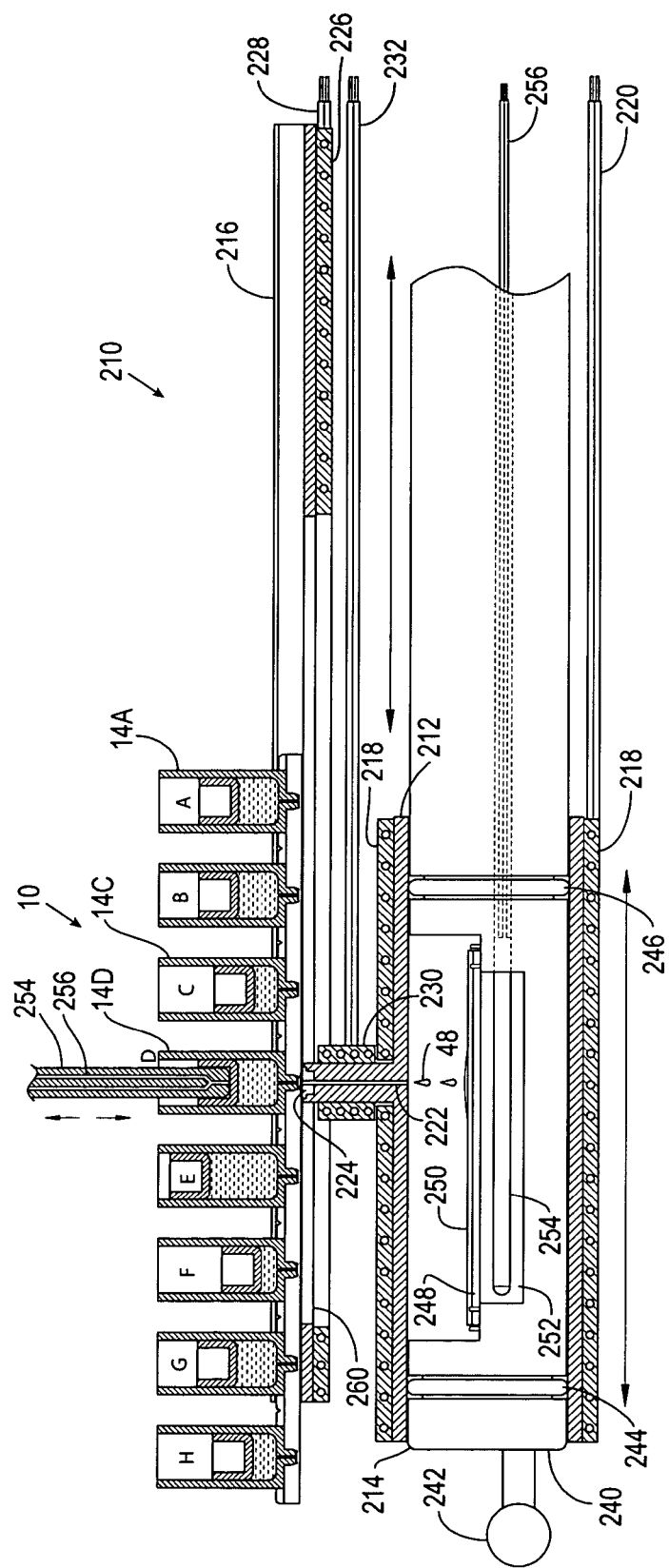
FIG. 82 is a cross-sectional side view of the reaction module of FIG. 79 in an alternate processing configuration.
Figure 83:
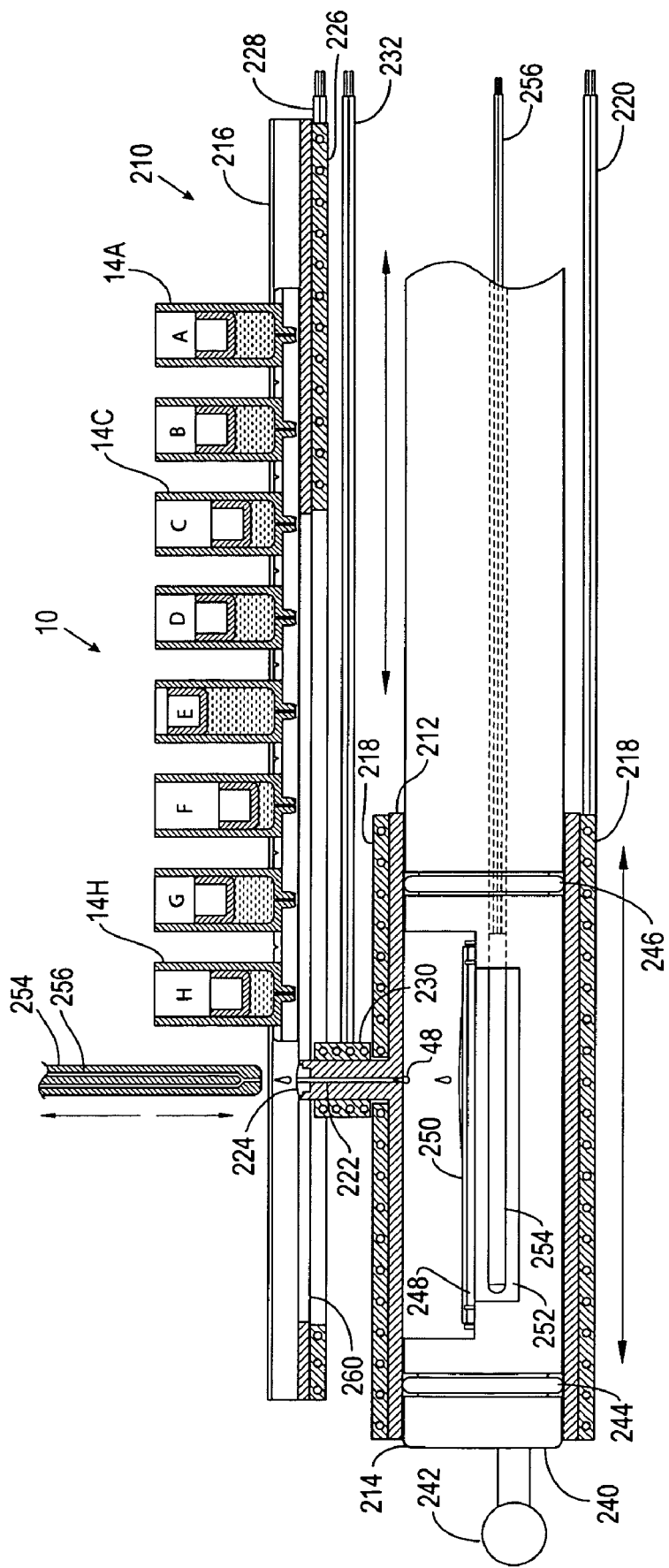
FIG. 83 is a cross-sectional side view of the reaction module of FIG. 79 in an alternate processing configuration.
Figure 84:
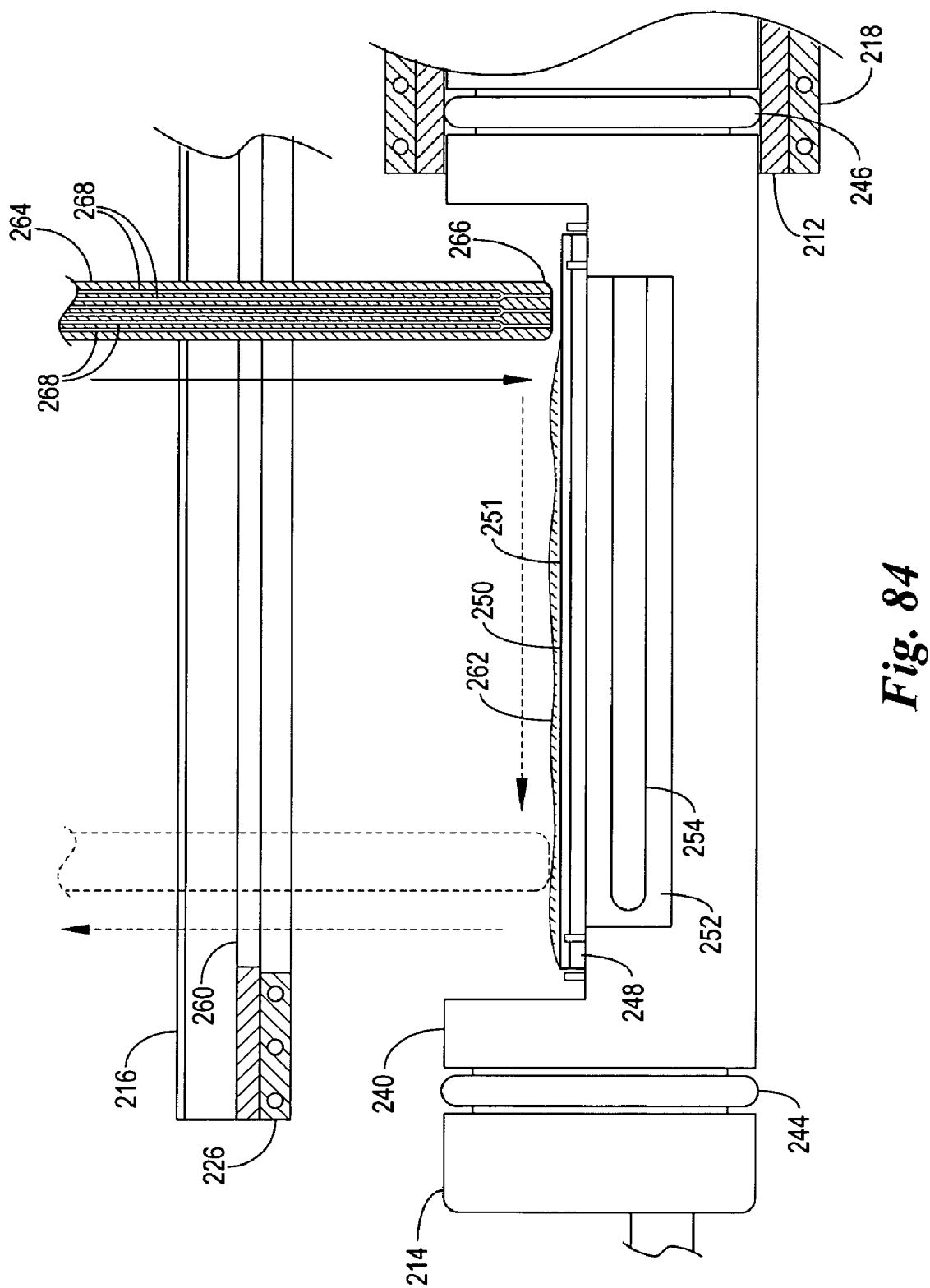
FIG. 84 is an enlarged fragmented cross-sectional side view of the reaction module of FIG. 79 in an alternate processing configuration.

As shown in FIGS. 79-85 in an alternate version of a reaction module of the apparatus of the present invention, reaction module 210 is similar to reaction module 110 in comprising a reaction compartment 212 similar to reaction compartment 112, a slide support element 214 similar to slide support element 114, and a reagent strip support device 216 similar to reagent strip support 116. Reaction compartment 212 comprises a reaction compartment heater 218 for heating the reaction compartment 212 and optionally the slide support element 214 when disposed therein or other gases or liquids therein. The reaction compartment heater 218 has leads 220 thereto for connecting to an electric power source (not shown). The reaction compartment 212 further comprises a reagent conduit 222 and an injector port orifice 224 for delivering a reagent or other solution into the reaction compartment 212. The reaction module 210 further comprises a reagent strip heater 226 incorporated into the reagent strip support device 216 for heating a reagent strip (such as any of the reagent strips disclosed herein) disposed thereon. Leads 228 connect the reagent strip heater 226 to an electric power source (not shown). The reaction module 210 further comprises a reagent conduit heater 230 for heating the reagent conduit 222 thereby functioning to heat a reagent as it passes through the reagent conduit 222 into the reaction compartment 212 merely onto the microscope slide if the reagent is applied when the slide is outside of the reaction compartment 212. Leads 232 connect the reagent conduit heater 230 to an electric power source (not shown). The slide support element 214 comprises a base 240 and, a handle 242, and a front O-ring 244 and a rear O-ring 246 for sealing the base 240 and microscope slide within the reaction compartment 212. The slide support element 214 further comprises a microscope slide platform/heater 248 and in operation has a microscope slide 250 disposed thereon, the microscope slide 250 having an upper surface 251. The base 240 further comprises a base cavity 252 positioned below the slide platform/heater 248 and has a base cavity heater 254 positioned therein and connected via lead 256 to an electric power source (not shown). The base cavity heater 254 functions to heat a reagent 258 disposed within the base cavity 252 to a temperature sufficient to heat the microscope slide 250 and biological specimen and reagent 258 disposed thereon as described elsewhere herein for other embodiments of the invention. The reagent 258 in one preferred embodiment completely immerses the microscope slide 250 as shown in FIG. 79. The reagent strip support device 216 in this embodiment comprises a slot 260 (which may also be included in the reagent strip support device 116) therein for enabling a dispenser plunger (i.e., dispenser element) 264 to deliver a reagent 262 directly upon the microscope slide 250 either when it is positioned within the reaction compartment 212 (FIGS. 79, 82, 83) or outside of the reaction compartment (FIGS. 80, 81). As shown in FIGS. 80, 81, and 84 reagent may be applied to or removed from the microscope slide 250 when the microscope 250 slide is positioned outside of the reaction compartment 212 on the slide support element 214. Reagent may be removed from the microscope slide 250 by the dispenser plunger 264 by moving the tip 266 of the dispenser plunger 264 over the microscope slide 250 and aspirating the reagent therefrom. Reagent may be delivered to or removed from the microscope slide 250 through one or more conduits 268 in the dispenser plunger 264 (FIG. 84). The conduits 268 may function to provide reagents or solutions, to remove reagents (via aspiration for example), or may provide air, gases, or liquids under pressure.

In other embodiments, reaction modules of the present invention may have any one or any combination of slide heating elements 136 or 248, reaction compartment heater 218, reagent strip heater 226, reagent conduit heater 230, and base cavity heater 254, and when present any of the heating systems described herein may function individually and independently of one another.

Figure 85:
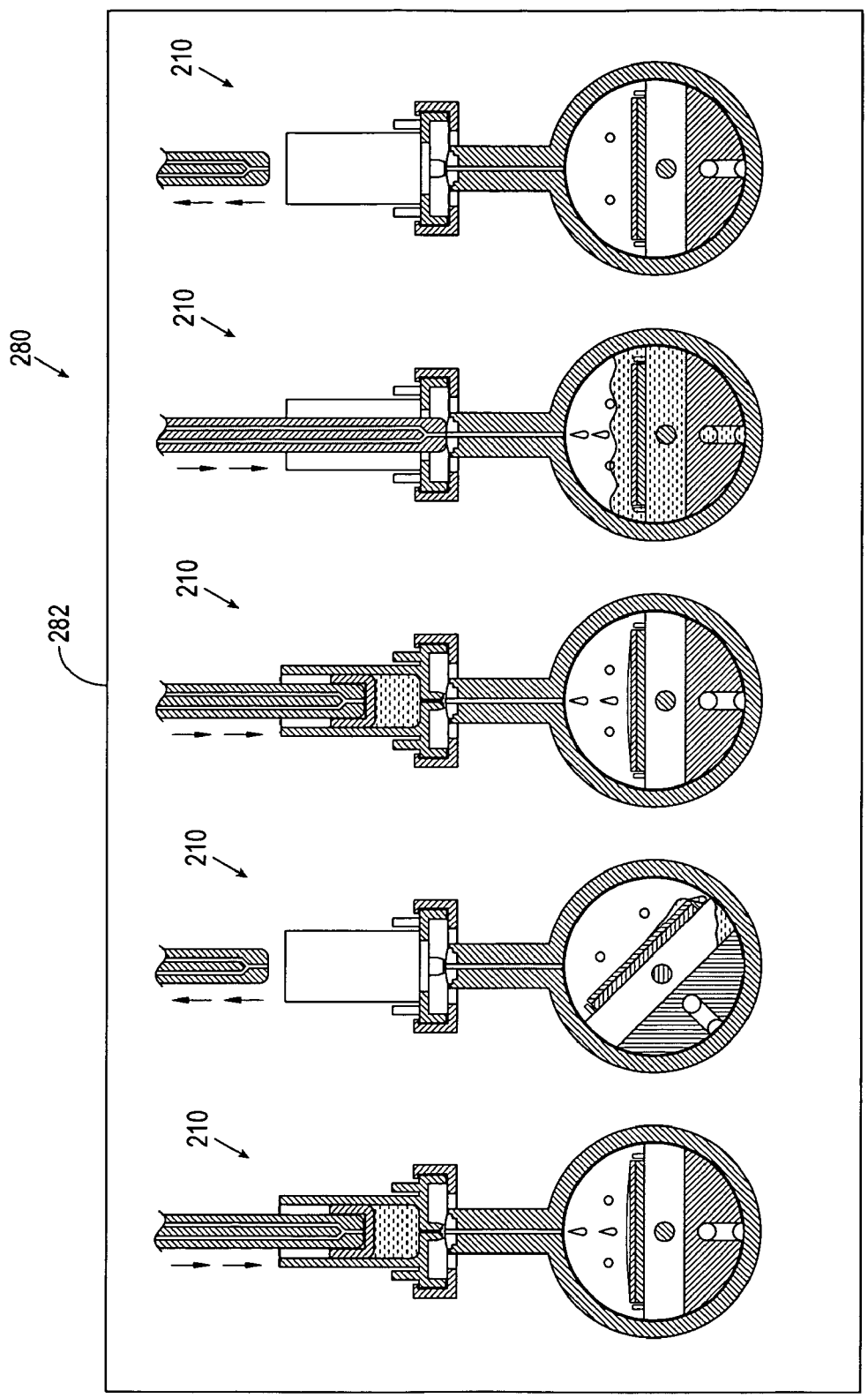
FIG. 85 is a front cross-sectional view of a plurality of reaction modules of the present invention combined in a chamber to form an in situ antigen recovery and staining apparatus of the present invention wherein the reaction modules are in various phases of operation.

As represented in FIG. 85, a plurality of reaction modules 210 are preferably positioned within a single chamber 282, wherein one or more such chambers 282 may be combined to provide a staining apparatus 280 comprising, e.g., 5 to 50 reaction modules 210.

In a preferred embodiment, the reaction compartment and/or slide support element of a reaction module of the present invention may be exposed to sterilization conditions which may include high heat (e.g., above 100° C., or more preferably above 130° C., and may use steam and/or chemicals to remove, or denature pathogens or residual chemicals or materials such as nucleic acids, antibodies, toxins or other proteins which remain in the reaction compartment and slide support element after the reaction module is used. In a preferred embodiment, the reaction compartment and/or slide support element after heating is quickly cooled to near room temperature or to below 50° C. within 3 s, 5 s, 10 s or 20 s for example to further denature or inactivate residual proteins or substances.

In an alternate embodiment of the invention, a plurality of slides are processed (either separately or within a common vessel) by applying a reagent or solution to the slide and pressurizing the vessel above atmospheric pressure to levels as discussed elsewhere herein, wherein the biological specimens, biochemicals, or other biological entity on the slide is not subjected to additional heating.

As described elsewhere herein, preferably the slide support element, reaction compartment, reagent strip, reagent strip support device, dispensing element, ports, conduits, mixing jets, pressurizing means, cooling means, aspiration devices, drainage ports, heating devices, and reagent conduits are independently operable and independently movable.

The in situ antigen recovery and staining apparatus of the present invention preferably has as one component a device for reading or detecting an optical character or code which identifies a reagent strip or reagent strip component such as a tile or container.

Various embodiments of the processes of the present invention include, but are not limited to, (1) application of a reagent to a slide using the present apparatus, and heating the slide, with or without a step of pressurizing the reaction compartment, (2) filling the base cavity with a reagent or solution such that it immerses the slide, pre-pressurizing the reaction compartment, then heating the slide and reagent solution in the base cavity, (3) filling the base cavity with a reagent or solution, then heating the slide and reagent or solution, without pre-pressurization before the heating step, or (4) placing a liquid in the bottom of the base cavity without the liquid directly touching the slide, then heating the liquid in the base cavity to cause vapor formation which pressurizes the reaction compartment and secondarily heats the slide and reagent therein (the slide also may optionally be heated by the slide heater).

Other embodiments of the present invention are shown and described in U.S. Pat. No. 6,534,008; U.S. Ser. No. 10/245,035; U.S. Pat. No. 6,855,292; and U.S. Provisionals 60/142,789; 60/684,047; 60/689,386 and 60/730,744, the entirety of each of which is hereby expressly incorporated herein by reference.

While the invention has been described above, and in further detail below, in connection with certain preferred embodiments herein so that aspects thereof may be more fully understood and appreciated, it is not intended to limit the invention to these particular embodiments. To the contrary, it is intended to cover all alternatives, modifications and equivalents as may be included within the scope of the invention as defined by the appended claims. Thus, these examples and embodiments, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

(1) Place microscope slide on slide support element and enclose within reaction compartment;
(2) Add antigen recovery buffer;
(3) Set slide heater at 130° C.;
(4) Pressure regulator set at 23 psig (259.9 kPa);
(5) Antigen recovery buffer reaches 125° C.;
(6) Incubate at 125° C. for 10 minutes;
(7) Turn off heater and turn on air or liquid cooling system;
(8) Cool 5 minutes; and
(9) Rinse with buffer and proceed with staining protocol.

Example 2

(1) Place microscope slide on support element;
(2) Enclose microscope slide within individual reaction compartment;
(3) Dispense 1-2 ml of antigen retrieval reagent onto microscope slide;
(4) Close all external ports;
(5) Open pressure port to pre-pressurize reaction compartment to about 25 psig (273.7 kPa);
(6) Turn on heat plate to reach about 120° C. on slide;
(7) Set pressure regulator to maintain 120° C. temperature by regulating the reaction compartment's pressure;
(8) Reagent reaches a temp of 120° C.;
(9) Heating is maintained for 30 minutes at about 120° C.;
(10) Turn off heater and turn on air or liquid cooling system;
(11) Cool 5-10 minutes;
(12) Release pressure to atmospheric pressure;
(13) Cool antigen retrieval reagent;
(14) Rinse slide with PBS wash buffer; and
(15) Proceed with staining protocol.

Example 3

Three mls of antigen recovery buffer present in reaction compartment can be heated to a particular reaction temperature at a particular pressure, including for example: 100° C. @ 8 psig (156.6 kPa), 106° C. @ 10 psig (170.3 kPa), 110° C. @ 12 psig (184.0 kPa), 115° C. @ 15 psig (204.7 kPa), 120° C. @ 16 psig (211.6 kPa), 125° C. @ 23 psig (259.9 kPa), or 130° C. @ 30 psig (308.1 kPa), 140° C. @ 40:retrieval buffer after a 60 minutes treatment time.

Example 4

Ambient temperature with pressure staining protocol:
1) Place slide on slide support;
2) Close chamber to seal slide support to chamber;
3) Dispense reagent by reagent strip or other dispensing element;
4) Pressurize the chamber with a separate gas to desired pressure (50-100 psig: 446-790.6 kPa);
5) Incubate the reagent for a desired time (10-120 minutes);
6) Depressurize the chamber by opening the waste port;
7) Rinse slide of reagent by rinsing and/or tilting and rinsing the slide;
8) Repeat steps 3-7 until all reagents are dispensed for a particular protocol and for a desired time.

Example 5

High temperature Antigen Retrieval protocol with pre-pressurization:
1) Place slide on slide support;
2) Close chamber to seal slide support to chamber;
3) Dispense reagent by reagent strip or other dispending element onto the microscope slide;
4) Pressurize the chamber with a separate gas to desired pressure (15-30 psig: 204.7-308.1 kPa);
5) Turn on at least one heating element (i.e., slide heater, chamber heater, cavity heater) and heat to 125° C.;
6) Pressure is maintained at 15-20 psig (204.7-239.2 kPa) by the pressure release valve or heating modulation (i.e., hearing elements turning off and on);
7) Incubate reagent at 125° C. for 10-30 minutes;
8) Turn heaters off and turn on cooling ducts (liquid or air) until reagent drops below 50° C.;
9) Depressurize the chamber sending condensation and pressure out the waste port;
10) Rinse slide of reagent by rinsing and/or tilting and rinsing the slide;
11) Dispense regent and incubate with or without pressure and/or with or without heat for a desired time;
12) Repeat steps 9-10 until all reagents are dispensed.

Example 6

High temperature Antigen Retrieval protocol without pre-pressurization:
1) Place slide on slide support;
2) Close chamber to seal slide support to chamber;
3) Dispense reagent by reagent strip or other dispending element and fill up the chamber with reagent by totally immersing the entire slide in reagent (i.e., antigen retrieval reagent);
4) Turn on at least one heating element (i.e., slide heater, chamber heater, cavity heater) and heat to 125° C.;
5) Pressure is produced by the reagent boiling;
6) Pressure is maintained at 25 psig (273.7 kPa) by the pressure release valve or heating modulation (i.e., heating elements turning off and on);
7) Reagent is incubated at a temperature of 125° C. for 10-30 minutes;
8) Turn heaters off and turn on cooling ducts (liquid or air) until reagent drops below 50° C.;
9) Depressurize the chamber sending condensation, reagent, and pressure out the waste port;
10) Rinse slide or reagent by rinsing and/or tilting and rinsing the slide;
11) Dispense reagent and incubate with or without pressure and/or with or without heat for a desired time;
12) Repeat steps 10-11 until all reagents are dispensed.

Example 7

High temperature Antigen Retrieval protocol—cavity produces steam to maintain high heat conditions with pressurization:
1) Place slide on slide support;
2) Close chamber to seal slide support to chamber;
3) Dispense reagent by reagent strip or other dispending element onto the microscope slide;
4) Add deionized (D.I.) water, or other liquid reagent to the cavity below the slide (deionized water not contacting the microscope slide);
5) Turn on slide heating element and cavity heaters and heat to 125° C.;
6) Pressure is produced by the deionized water boiling in the cavity and producing steam to heat the reagent on the microscope slide;
7) Pressure is maintained at 25 psig (273.7 kPa) by the pressure release valve or heating modulation (i.e., heating elements turning off and on);
8) Reagent is incubated at a temperature of 125° C. for 10-60 minutes;
9) Turn heaters off and turn on cooling ducts (liquid or air) until reagent drops below 50° C.;
10) Depressurize the chamber sending condensation, deionized water and pressure out the water port;
11) Rinse slide of reagent by rinsing and/or tilting and rinsing the slide;
12) Dispense reagent and incubate with or without pressure and/or with or without heat for a desired time;
13) Repeat steps 10-11 until all reagents are dispensed.

In summary, the invention in one embodiment contemplates an in situ antigen recovery and staining apparatus, comprising a plurality of independently operable reaction modules with each reaction module comprising: a reaction compartment having an inner space, a slide support element able to support a microscope slide in a horizontal position, the slide support element positionable within or adjacent the inner space of the reaction compartment for sealing the microscope slide therein wherein the reaction compartment is pressurizable (or optimally depressurizable) to maintain an internal pressure which exceeds (or is below) atmospheric pressure, and a dispensing element for dispensing a reagent into the reaction compartment while the reaction compartment is pressurized, and may further comprise a heating element for heating the microscope slide within the reaction compartment.

The present invention contemplates a reaction module, comprising: a reaction compartment having an inner space, a slide support element able to support a microscope slide in a horizontal position, the slide support element positionable within or adjacent the inner space of the reaction compartment for sealing the microscope slide therein wherein the reaction compartment can then be pressurized (or, optionally, depressurized) to maintain an internal pressure which exceeds (or is below) atmospheric pressure, and a dispensing element for dispensing a reagent into the reaction compartment while the reaction compartment is pressurized. The reaction module may optionally have a heating element for heating the microscope slide, and/or a reagent strip support device for supporting a reagent strip having a plurality of reagent containers each of which contains or is able to contain a reagent therein, wherein the reagent strip support device supports the reagent strip in a position external to and adjacent the reaction compartment, and the dispensing element may be adapted to engage the reagent container thereby causing the reagent to be delivered from the reagent container into the inner space of the reaction compartment and onto the microscope slide.

More particularly, the invention contemplates an in situ antigen recovery and staining apparatus, comprising a plurality of independently operable reaction modules, wherein each reaction module comprises: a reaction compartment having an inner space, a slide support element able to support a microscope slide in a horizontal position, the slide support element positionable within or adjacent the inner space of the reaction compartment for sealing the microscope slide therein wherein the reaction compartment can then be pressurized (or, optionally, depressurized) to maintain an internal pressure which exceeds (or is below) atmospheric pressure, a heating element for heating the microscope slide, a reagent strip support device for supporting a reagent strip having a plurality of reagent containers each of which contains or is able to contain a reagent therein, wherein the reagent strip support device supports the reagent strip in a position external to and adjacent the reaction compartment, and a dispensing element for engaging the reagent container thereby causing the reagent to be delivered from the reagent container into the inner space of the reaction compartment and onto the microscope slide, and wherein each of the reaction compartments of the plurality of reaction modules is individually and independently pressurizable (or, optionally, depressurizable) and wherein each of the heating elements of the plurality of reaction modules is individually and independently heatable.

In the in situ antigen recovery and staining apparatus, the reaction compartment may be pressurizable before, during, or after the heating element heats the microscope slide, the heating element may be a component of the slide support element and may be positionable directly beneath the microscope slide, the reaction compartment may have a cylindrical, tubular shape wherein the slide support element has a cylindrical shape, or the reaction compartment may have a rectangular shape, such that the slide support element has a rectangular shape.

In the in situ antigen recovery and staining apparatus, the slide support element of each reaction module may be independently movable in relation to each other slide support element, the reagent strip of each reaction module may be independently movable in relation to each other reagent strip, the reaction compartment of each reaction module may be independently movable in relation to each other reaction compartment, and the dispensing element of each reaction module may be independently movable in relation to each other dispensing element, the reaction compartment is preferably pressurizable to maintain a pressure above atmospheric pressure, such as 0 to 350 psig (101.3-2514 kPa), to a pressure of 1 to 100 psig (108.2-790.6 kPa), to a pressure of 5 to 50 psig (135.8-446.0 kPa), or to a pressure of 10 to 40 psig (170.3-377.0 kPa), or is depressurizable to maintain a pressure below atmospheric pressure to a level as low as 100 kPa to 10 kPa to 1 kPa to 100 Pa to 10 Pa to 1 Pa to 0.1 Pa.

In the in situ antigen recovery and staining apparatus, the reagent disposed onto or about the microscope slide may be heated to a temperature of 25° C. to 37° C., 37° C. to 56° C., 56° C. to 85° C., 85° C. to 100° C., 100° C. to 125° C., 125° C. to 135° C., 135° C. to 150° C., 150° C. to 175° C., 175° C. to 200° C., 200° C. to 225° C., 225° C. to 250° C., 250° C. to 275° C., 275° C. to 300° C., 300° C. to 325° C., or 325° C. to 350° C. When the slide support element of the reaction module is movable, the reaction compartment may be stationary or movable, and the reagent strip support device may be stationary or movable, when the slide support element of the reaction module is stationary, the reaction compartment is movable, and the reagent strip support device may be stationary or movable. When the slide support element of the reaction module is movable or stationary, and the reaction compartment is movable, and the reagent strip support device is movable, the reaction compartment may be movable independently of the reagent strip support device. Further, the reagent strip support device may be movable in either a forward or reverse direction to carry the reagent strip when loaded thereon in either a forward or reverse direction, and when the reagent strip support device is stationary, the reagent strip may be movable in either a forward or reverse direction when loaded thereon. The reagent strip support device and the reaction compartment are connected to each other, or not connected. The reaction module may comprise at least one of an air duct for pressurizing the reaction compartment or causing mixing of the reagent on the slide, or a cooling duct for enhancing the rate of cooling of the heating element after heating, a supply port for delivering a liquid to the slide support element, and a drainage duct for removing reagents supplied to the microscope slide. The apparatus may comprise a reagent conduit in the reaction module for enabling delivery of reagent from the reagent strip into the reaction compartment, a heating device disposed about the reagent conduit for heating the reagent delivered therethrough, a heating device for heating the reaction compartment, and a heating device in the reagent strip support device for heating the reagent strip or portions thereof.

The slide support element of the apparatus may have a cavity in a position below the microscope slide for containing a quantity of solution and the cavity may have a cavity heater for heating the solution within the cavity. The dispensing element may be operable independently of the reagent strip support device, and the dispensing element preferably functions to cause expulsion of reagent from a reagent container of the reagent strip and to dispense a reagent or solution from a reagent or solution source remote from the reagent strip. The slide support element may receive reagent from the reagent strip or reagent or solution from a remote source when the slide support element is disposed inside or outside of the reaction compartment. The dispensing element is preferably able to apply suction, or is able to apply liquid, air, or gas under pressure. The slide support element may be encloseable within the reaction compartment by moving the slide support element into the reaction compartment or by moving the reaction compartment about the slide support element. The slide support element may be tiltable to allow drainage of reagent or solution from the microscope slide. The plurality of reaction modules can be assembled into at least one chamber to form a reaction apparatus. Each slide support element, reagent strip support device, dispensing element, and reaction compartment of the apparatus is preferably separately replaceable or exchangeable, and the reaction module preferably has means for releasing pressure from or regulating pressure within the reaction compartment.

The present invention also contemplates a reconfigurable reagent dispensing strip, comprising a plurality of reagent modules, each reagent module comprising a tile and a reagent container secured thereto, each reagent module adapted to be attachable to and detachable from an adjacent reagent module such that once the plurality of reagent modules are attached together in a first sequence, one or more of the reagent modules can be detached and reattached to reconfigure the plurality of reagent modules in a second sequence different from the first sequence. The reconfigurable reagent dispensing strip may have a connecting link for connecting adjacent reagent modules, and an injector for enabling a reagent within the reagent container to be dispensed from the reagent container, and the reagent container may be removable from the tile. Further, at least one of the reagent containers contains a reagent selected from the group consisting of antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives.

Alternatively, the reconfigurable reagent dispensing strip may comprise a base, having a plurality of container platforms, and a plurality of reagent containers, with each container platform having a reagent container secured thereto, wherein each reagent container is adapted to be attachable to and detachable from the container platform such that once the plurality of reagent containers are attached together in a first sequence, one or more of the reagent containers can be detached and reattached to a different container platform to reconfigure the plurality of reagent containers in a second sequence different from the first sequence, thereby forming a reconfigured reagent dispensing strip. The reagent container may be positioned upon a tile which is detachable from the base. The reagent container or container platform may further comprise an injector for enabling a reagent within the reagent container to be dispensed from the reagent container. At least one of the reagent containers contains a reagent selected from the group consisting of antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives.

Alternatively, the reconfigurable reagent dispensing strip may comprise a plurality of reagent modules, each reagent module comprising a tile and a reagent container secured thereto, wherein the tiles are initially constructed in a unitary, integral configuration and each tile is adapted to be attachable to and detachable from an adjacent tile such that the reagent modules are connected in a first sequence, and wherein when one or more of the tiles is detached, the one or more tiles can be reattached to reconfigure the plurality of reagent modules in a second sequence different from the first sequence, and may further comprise a connecting link for re-connecting tiles of adjacent reagent modules. The reagent module may further comprise an injector for enabling a reagent within the reagent container to be dispensed from the reagent container, and the reagent container may be removable from the tile. Further, at least one of the reagent containers contains a reagent selected from the group consisting of antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives.

In another embodiment, the present invention contemplates a method of treating a microscope slide, comprising: providing a plurality of independently operable reaction modules, each reaction module comprising: a reaction compartment having an inner space, a slide support element able to support a microscope slide in a horizontal position, the slide support element positionable within or adjacent the inner space of the reaction compartment for sealing the microscope slide therein, and a dispensing element for dispensing a reagent into the reaction compartment, then disposing the microscope slide onto the slide support element, positioning the microscope slide within the reaction compartment, pressurizing the reaction compartment to maintain an internal pressure which exceeds atmospheric pressure, and actuating the dispensing element to cause the reagent to be delivered into the reaction compartment while the reaction compartment is pressurized and wherein the reagent is delivered at a pressure which exceeds the pressure within the reaction compartment, and optionally heating the microscope slide and reagent within the reaction compartment. The method may comprise providing a plurality of independently operable reaction modules, each reaction module comprising a reaction compartment having an inner space, a slide support element able to support a microscope slide in a horizontal position, the slide support element positionable within or adjacent the inner space of the reaction compartment for sealing the microscope slide therein, and a dispensing element for dispensing a reagent into the reaction compartment, then disposing the microscope slide onto the slide support element, positioning the microscope slide within the reaction compartment and enclosing the microscope slide therein, actuating the dispensing element to cause the reagent to be delivered into the reaction compartment, and pressurizing the reaction compartment to maintain an internal pressure which exceeds atmospheric pressure, or, optionally, depressurizing the reaction compartment below atmospheric pressure, and, optionally, heating the microscope slide and reagent within the reaction compartment.

The method of the invention may comprise providing a reaction module comprising: a reaction compartment having an inner space, and a slide support element able to support a microscope slide in a horizontal position, the slide support element positionable within or adjacent the inner space of the reaction compartment for sealing the microscope slide therein, then disposing the microscope slide onto the slide support element, positioning the slide support element and microscope slide thereon within the reaction compartment, pressurizing the reaction compartment to maintain an internal pressure which exceeds atmospheric pressure, and disposing a reagent onto the microscope slide while the reaction compartment is pressurized, and optionally heating the microscope slide and the reagent thereon.

The method may comprise providing a plurality of independently operable reaction modules, each reaction module comprising: a reaction compartment having an inner space, a slide support element able to support a microscope slide in a horizontal position, the slide support element positionable within or adjacent the inner space of the reaction compartment for sealing the microscope slide therein, and a dispensing element for dispensing a reagent into the reaction compartment, then disposing the microscope slide onto the slide support element, positioning the microscope slide within the reaction compartment, depressurizing the reaction compartment to maintain an internal pressure which is less than atmospheric pressure, and actuating the dispensing element to cause the reagent to be delivered into the reaction compartment while the reaction compartment is depressurized.

The method may comprise providing a plurality of independently operable reaction modules, each reaction module comprising: a reaction compartment having an inner space, a slide support element able to support a microscope slide in a horizontal position, the slide support element positionable within or adjacent the inner space of the reaction compartment for sealing the microscope slide therein, and a dispensing element for dispensing a reagent into the reaction compartment, then disposing the microscope slide onto the slide support element, positioning the microscope slide within the reaction compartment and enclosing the microscope slide therein, actuating the dispensing element to cause the reagent to be delivered into the reaction compartment, and depressurizing the reaction compartment to maintain an internal pressure which is less than atmospheric pressure.

Preferably the invention comprises a method of treating a microscope slide, comprising, providing a plurality of independently operable reaction modules, each reaction module comprising: a reaction compartment having an inner space, a slide support element able to support a microscope slide in a horizontal position, the slide support element positionable within or adjacent the inner space of the reaction compartment for sealing the microscope slide therein, a heating element for heating the microscope slide, a reagent strip support device for supporting a reagent strip having a plurality of reagent containers each of which contains or is able to contain a reagent therein, wherein the reagent strip support device supports the reagent strip in a position external to and adjacent the reaction compartment, and a dispensing element for engaging the reagent container thereby causing the reagent to be delivered from the reagent container into the inner space of the reaction compartment and onto the microscope slide, and wherein each of the reaction compartments of the plurality of reaction modules is individually and independently pressurizable (or, optionally, depressurizable) and wherein each of the heating elements of the slide support elements of the plurality of reaction modules is individually and independently heatable, then disposing the microscope slide onto the slide support element, positioning the slide support element and microscope slide thereon within the reaction compartment, placing the reagent strip onto the reagent strip support device, actuating the dispensing element to cause the reagent to be delivered onto the microscope slide, actuating the heating element to heat the slide, pressurizing the reaction compartment to maintain an internal pressure which exceeds atmospheric pressure, and removing the reagent from the microscope slide.

In the method, the step of pressurizing (or depressurizing) the reaction compartment may occur before, during, or after the heating of the microscope slide by the heating element. The reaction compartment may have a cylindrical, tubular shape for enhancing pressure distribution within the reaction compartment. The slide support element of each reaction module may be moved independently in relation to each other slide support element, the reagent strip of each reaction module may be moved independently in relation to each other reagent strip, and the dispensing element of each reaction module may be moved independently in relation to each other dispensing element. The reaction compartment may be pressurized to a pressure of above 0 to 350 psig (101.3-2514 kPa), to a pressure of 1 to 100 psig (108.2-790.6 kPa), to a pressure of 5 to 50 psig (135.8-446.0 kPa), or to a pressure of 10 to 40 psig (170.3-377.0 kPa). The reaction compartment may be depressurized to maintain a pressure below atmospheric pressure to a level as low as 100 kPa to 10 kPa to 1 kPa to 100 Pa to 10 Pa to 1 Pa to 0.1 Pa. The reagent disposed onto or about the microscope slide may be heated to a temperature of 25° C. to 37° C., 37° C. to 56° C., 56° C. to 85° C., 85° C. to 100° C., 100° C. to 125° C., 125° C. to 135° C., 135° C. to 150° C., 150° C. to 175° C., 175° C. to 200° C., 200° C. to 225° C., 225° C. to 250° C., 250° C. to 275° C., 275° C. to 300° C., 300° C. to 325° C., to 325° C. to 350° C. The step of positioning the slide support element may comprise moving the slide support element of the reaction module into the reaction compartment while the reaction compartment is stationary, or the step of positioning the slide support element may comprise moving the slide support element of the reaction module and moving the reaction compartment. The reagent strip may be positioned in a dispensing position by moving the reagent strip support device thereby moving the reagent strip to the dispensing position, or by moving the reagent strip while the reagent strip support device is stationary. The method may comprise moving the slide support element of the reaction module, moving the reaction compartment is movable, and moving the reagent strip support device, wherein the reaction compartment is movable independently of the reagent strip support device.

The step of positioning the slide support element may comprise maintaining the slide support element of the reaction module stationary, and moving the reaction compartment to enclose the slide support element. The reaction compartment may be movable independently of the reagent strip support device and wherein the reagent strip support device may be movable independently of the reaction compartment. The reagent strip support device may be moved in either a forward or reverse direction to carry the reagent strip in either a forward or reverse direction. The reagent strip support device may be maintained stationary and the reagent strip thereon may be moved in either a forward or reverse direction. The reaction module may comprise at least one of an air duct for pressurizing the reaction compartment or causing mixing of the reagent on the slide, a cooling duct for enhancing the rate of cooling of the heating element after heating, a supply port for delivering a liquid to the slide support element, and a drainage duct for removing reagents supplied to the microscope slide.

The method may comprise delivering reagent from the reagent strip into the reaction compartment via a reagent conduit in the reaction module, heating the reagent conduit for heating the reagent delivered therethrough, heating the reaction compartment, heating the reagent strip or portions thereof using a heating device in the reagent strip support device, dispensing a solution in a cavity in the slide support element below the microscope slide and heating the solution in the cavity. The dispensing element may be operable independently of the reagent strip support device. The method may comprise using the dispensing element to dispense a reagent or solution from a reagent or solution source remote from the reagent strip, applying reagent from the reagent strip or reagent or solution from a remote source when the slide support element is disposed inside or outside of the reaction compartment, and/or applying suction, or liquid, air, or gas under pressure to the microscope slide via the dispensing element to cause removal of a reagent or solution from the microscope slide. The step of positioning the slide support element within the reaction compartment may occur by moving the slide support element into the reaction compartment or by moving the reaction compartment about the slide support element thereby enclosing the slide support element within the reaction compartment, and may comprise the step of tilting the slide support element to allow drainage of reagent or solution from the microscope slide.

While the invention has been described herein in connection with certain embodiments so that aspects thereof may be more fully understood and appreciated, it is not intended that the invention be limited to these particular embodiments. On the contrary, it is intended that all alternatives, modifications and equivalents are included within the scope of the invention as defined by the appended claims. Thus the examples and embodiments described herein, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

Changes may be made in the construction and the operation of the various components, elements and assemblies described herein or in the steps or the sequence of steps of the methods described herein without departing from the spirit and scope of the invention as defined in the following claims.

What is claimed is:

1. A reconfigurable reagent dispensing strip, comprising:
a base comprising a plurality of tiles; and
a plurality of reagent containers; and wherein each tile of the plurality of tiles has one of the reagent containers of the plurality of reagent containers secured thereto or is adapted to have a reagent container secured thereto, wherein the plurality of reagent containers are arranged in a first sequence on the base, and wherein at least one of the tiles of the base can be detached from and reattached to the base to reconfigure the plurality of reagent containers in a second sequence which is different from the first sequence, and wherein each tile has an upper surface and a lower surface and has an aperture extending completely therethrough from the upper surface of the tile through the lower surface of the tile and which is adapted to receive an injector, and completely through which aperture a reagent in the reagent container can be passed via the injector.

2. The reconfigurable reagent dispensing strip of claim 1 wherein the reagent container is adapted to be detachable from the tile to which it is secured.

3. The reconfigurable reagent dispensing strip of claim 1 wherein each reagent container is adapted to be reattachable to one of the tiles of the plurality of tiles.

4. The reconfigurable reagent dispensing strip of claim 1 wherein each tile of the plurality of tiles has a container platform to which the reagent container is attached for securing the reagent container to the tile.

5. The reconfigurable reagent dispensing strip of claim 4 wherein the reagent container or container platform of each tile further comprises the injector for enabling a reagent within the reagent container to be dispensed from the reagent container.

6. The reconfigurable reagent dispensing strip of claim 1 wherein at least one of the plurality of reagent containers contains a reagent.

7. The reconfigurable reagent dispensing strip of claim 6 wherein the reagent contained within the reagent container is selected from the group consisting of antigen retrieval reagents, RNA and DNA probes, citrate buffer, EDTA, TRIS, PBS, with or without surfactants or ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives.

8. A reconfigurable reagent dispensing strip, comprising:
a base comprising a plurality of tiles; and
a plurality of reagent containers; and wherein each tile of the plurality of tiles has one of the reagent containers of the plurality of reagent containers secured thereto or is adapted to have a reagent container secured thereto, wherein the plurality of reagent containers are arranged in a first sequence on the base, and wherein at least one of the tiles of the base can be detached from and reattached to the base to reconfigure the plurality of reagent containers in a second sequence which is different from the first sequence, and wherein each reagent container is adapted to be detachable from the tile to which it is secured and wherein each reagent container is adapted to be reattachable to one of the tiles of the plurality of tiles, and wherein each tile has an upper surface and a lower surface and has an aperture extending completely therethrough from the upper surface of the tile through the lower surface of the tile and which is adapted to receive an injector, and completely through which aperture a reagent in the reagent container can be passed via the injector.

9. The reconfigurable reagent dispensing strip of claim 8 wherein each tile of the plurality of tiles has a container platform to which the reagent container is attached for securing the reagent container to the tile.

10. The reconfigurable reagent dispensing strip of claim 9 wherein the reagent container or container platform of each tile further comprises the injector for enabling a reagent within the reagent container to be dispensed from the reagent container.

11. The reconfigurable reagent dispensing strip of claim 8 wherein at least one of the plurality of reagent containers contains a reagent.

12. The reconfigurable reagent dispensing strip of claim 11 wherein the reagent contained within the reagent container is selected from the group consisting of antigen retrieval reagents, RNA and DNA probes, citrate buffer, EDTA, TRIS, PBS, with or without surfactants or ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives.

* * * * *